(12) United States Patent
Woo

(10) Patent No.: US 8,070,742 B2
(45) Date of Patent: Dec. 6, 2011

(54) METHOD FOR CONTROLLING BODY FLUID CONDITION USING DIURETICS, BASED ON WEIGHT MEASUREMENT

(76) Inventor: Sang Hoon Woo, Palo Alto, CA (US)

( * ) Notice: Subject to any disclaimer, the term of this patent is extended or adjusted under 35 U.S.C. 154(b) by 96 days.

(21) Appl. No.: 12/202,072

(22) Filed: Aug. 29, 2008

(65) Prior Publication Data

US 2009/0062727 A1 Mar. 5, 2009

Related U.S. Application Data

(60) Provisional application No. 61/048,113, filed on Apr. 25, 2008, provisional application No. 60/988,375, filed on Nov. 15, 2007, provisional application No. 60/986,974, filed on Nov. 9, 2007, provisional application No. 60/979,634, filed on Oct. 12, 2007, provisional application No. 60/967,025, filed on Sep. 1, 2007.

(51) Int. Cl.
*A61M 31/00* (2006.01)

(52) U.S. Cl. .............. 604/503; 604/66; 604/506
(58) Field of Classification Search ........... 604/65–67
See application file for complete search history.

(56) References Cited

U.S. PATENT DOCUMENTS

| | | | | |
|---|---|---|---|---|
| 5,395,340 | A | * | 3/1995 | Lee .................... 604/151 |
| 6,558,351 | B1 | * | 5/2003 | Steil et al. ............ 604/131 |
| 6,562,001 | B2 | * | 5/2003 | Lebel et al. ............ 604/65 |
| 2005/0137481 | A1 | * | 6/2005 | Sheard et al. .......... 600/508 |
| 2006/0052764 | A1 | * | 3/2006 | Gelfand et al. ........ 604/500 |

* cited by examiner

*Primary Examiner* — Nicholas Lucchesi
*Assistant Examiner* — Jenna Zhang
(74) *Attorney, Agent, or Firm* — Samantha S. Woo

(57) ABSTRACT

The system for controlling body fluids overcomes the limitations of the prior art by automatically infusing diuretic and/or other drugs into a human patient. In one approach, the rate of infusion of the diuretic is adjusted based on the measured weight of the patient. For example, this weight can be transmitted wirelessly to a portable diuretic infusion device attached to the patient.

20 Claims, 58 Drawing Sheets

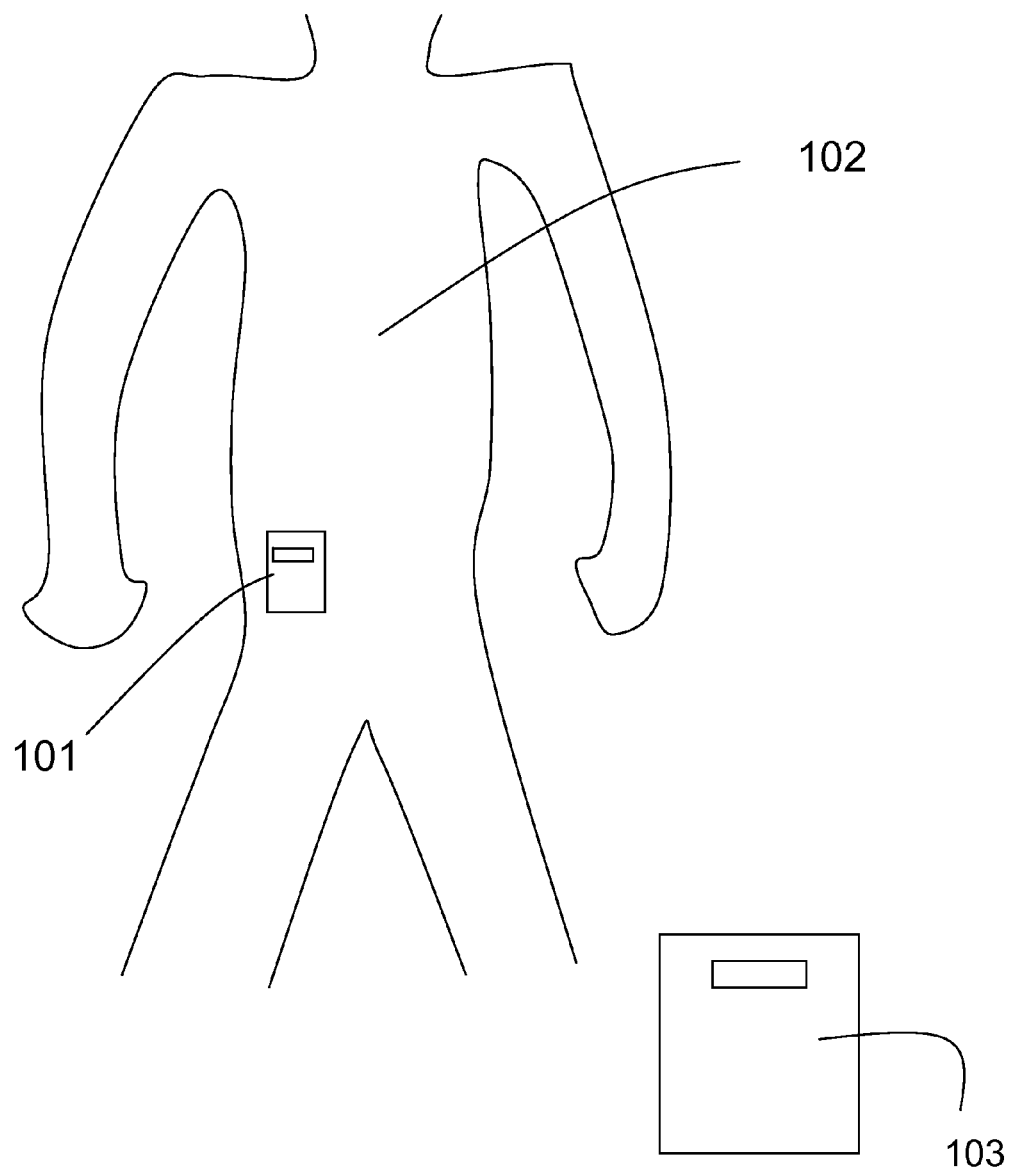
Figure 1-a

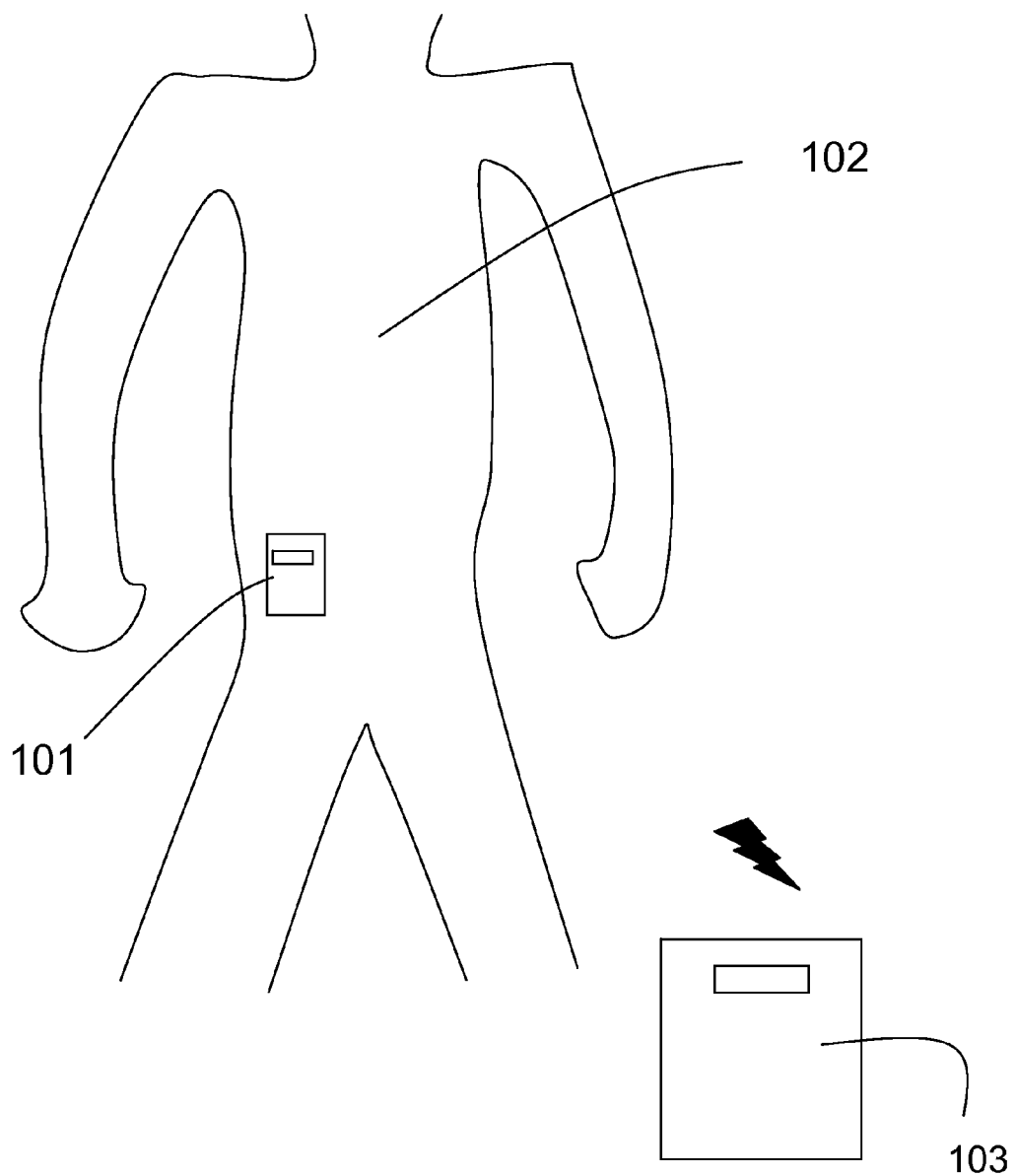
Figure 1-b

<Furosemide infusion rate protocol>

If body weight is more than 3kg above target weight -
  Increase basal rate by 100% from initial basal rate and
  provide bolus infusion of 40mg at 7AM and 4PM.
If body weight is 2-3kg above target weight -
  Increase basal rate by 75% from initial basal rate and
  provide bolus infusion of 30mg at 7AM and 4PM.
If body weight is 1-2kg above target weight -
  Increase basal rate by 50% from initial basal rate and
  provide bolus infusion of 20mg at 7AM and 4PM.
If body weight is 0-1kg above target weight -
  Increase basal rate by 25% from initial basal rate and
  provide bolus infusion of 10mg at 7AM and 4PM.
If body weight is 0-1kg below target weight -
  Decrease basal rate by 50% from initial basal rate and
  provide bolus infusion of 5mg at 7AM.
If body weight is 1-2kg below target weight -
  Decrease basal rate by 75% from initial basal rate and
  hold bolus infusion.
If body weight is more than 2kg below target weight -
  Stop basal rate and bolus infusion.

<Bumetanide infusion rate protocol>

If body weight is more than 3kg above target weight -
  Increase basal rate by 100% from initial basal rate,
  Infuse bolus of 2mg at 6AM and 4PM.
If body weight is 2-3kg above target weight -
  Increase basal rate by 75% from initial basal rate,.
  Infuse bolus of 1mg at 6AM and 4PM.
If body weight is 1-2kg above target weight -
  Increase basal rate by 50% from initial basal rate.
If body weight is 0-1kg above target weight -
  Increase basal rate by 25% from initial basal rate.
If body weight is 0-1kg below target weight -
  Decrease basal rate by 50% from initial basal rate.
If body weight is 1-2kg below target weight -
  Decrease basal rate by 75% from initial basal rate.
If body weight is more than 2kg below target weight -
  Stop infusion.

Figure 4

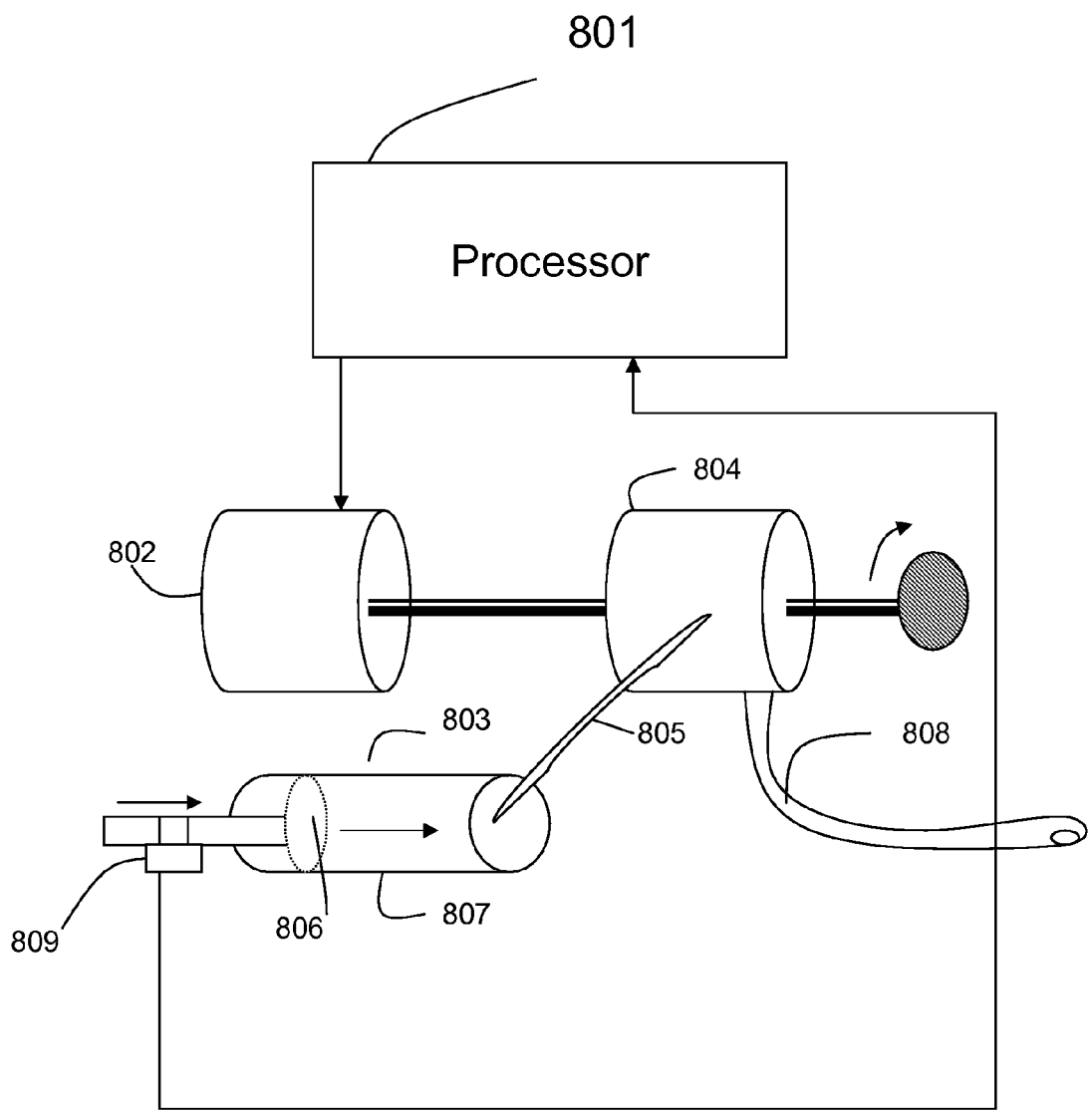
Figure 8-a

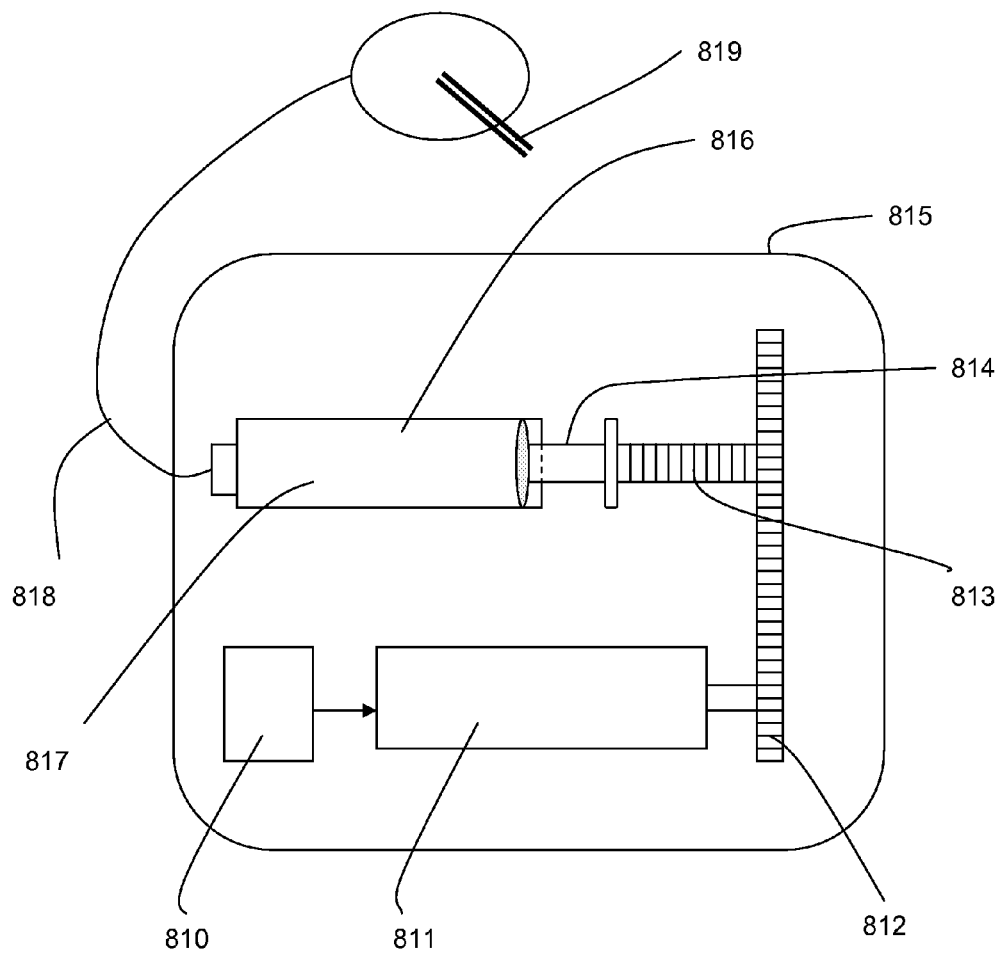
Figure 8-b

<Oral furosemide dose titration protocol>

Put in current dose.

If body weight is more than 3kg above target weight -
　Increase current dose by 200%.
　Display instruction "call your doctor".
If body weight is 1.5-3kg above target weight -
　Increase current dose by 100%.
If body weight is 0.5-1.5kg above target weight -
　Increase current dose by 50%.
If body weight is 0-0.5kg above target weight -
　Continue current dose.
If body weight is 0-1.5kg below target weight -
　Decrease current dose by 50%.
If body weight is more than 1.5kg below target weight -
　Stop furosemide
　Display instruction "call your doctor".

Figure 19

<Furosemide infusion rate protocol>

Enter initial basal rate.

If body weight is more than 3kg above target weight -
  Increase basal rate by 100% from initial basal rate,
  Provide 20mg bolus infusion.
If body weight is 2-3kg above target weight -
  Increase basal rate by 75% from initial basal rate,
  Provide 10mg bolus infusion
If body weight is 1-2kg above target weight -
  Increase basal rate by 50% from initial basal rate,
  Provide 5mg bolus infusion.
If body weight is 0-1kg above target weight -
  Increase basal rate by 25% from initial basal rate.
If body weight is 0-1kg below target weight -
  Decrease basal rate by 50% from initial basal rate.
If body weight is 1-2kg below target weight -
  Decrease basal rate by 75% from initial basal rate.
If body weight is more than 2kg below target weight -
  Stop infusion.

Figure 20

<Furosemide infusion rate protocol 1>

If body weight is more than 3kg above target weight -
  Increase basal rate by 75% from initial basal rate,
  Provide 10mg bolus infusion at 9am and 5pm.
If body weight is 2-3kg above target weight -
  Increase basal rate by 50% from initial basal rate,
  Provide 10mg bolus infusion at 9am and 5pm.
If body weight is 0-2kg above target weight -
  Continue current basal infusion rate,
  No bolus infusion.

<Furosemide infusion rate protocol 2>

If body weight is more than 3kg above target weight -
  Increase basal rate by 125% from initial basal rate,
  Provide 30mg bolus infusion at 9am and 5pm.
If body weight is 2-3kg above target weight –
  Increase basal rate by 100% from initial basal rate,
  Provide 20mg bolus infusion at 9am and 5pm.
If body weight is 1-2kg above target weight -
  Increase basal rate by 75% from initial basal rate
  Provide 10mg bolus infusion at 9am and 5pm.
If body weight is 0-1kg above target weight -
  Increase basal rate by 50% from initial basal rate
  Provide 10mg bolus infusion at 9am.

Figure 23

<Furosemide infusion rate protocol 3>

If body weight is more than 3kg above target weight -
  Increase basal rate by 125% from initial basal rate,
  Provide 30mg bolus infusion at 9am and 5pm,
  Display on screen "take 40mg furosemide pill now".
If body weight is 2-3kg above target weight -
  Increase basal rate by 100% from initial basal rate,
  Provide 20mg bolus infusion at 9am and 5pm,
  Display on screen "take 20mg furosemide pill now".
If body weight is 1-2kg above target weight -
  Increase basal rate by 75% from initial basal rate,
  Provide 10mg bolus infusion at 9am and 5pm,
  Display on screen "take 10mg furosemide pill now".
If body weight is 0-1kg above target weight -
  Increase basal rate by 50% from initial basal rate.

Figure 24

<Furosemide infusion rate protocol 4>

If body weight is more than 3kg above target weight -
  Increase basal rate by 150% from initial basal rate,
  Provide 40mg bolus infusion at 9am and 5pm.
If body weight is 2-3kg above target weight -
  Increase basal rate by 100% from initial basal rate,
  Provide 20mg bolus infusion at 9am and 5pm.
If body weight is 1-2kg above target weight -
  Increase basal rate by 75% from initial basal rate,
  Provide 10mg bolus infusion at 9am and 5pm.
If body weight is 0-1kg above target weight -
  Increase basal rate by 50% from initial basal rate.

Figure 25

<Furosemide infusion rate protocol 5>

If body weight is more than 3kg above target weight -
  Infuse furosemide 40mg bolus at 9am and 5pm.
If body weight is 2-3kg above target weight -
  Infuse furosemide 20mg bolus at 9am and 5pm.
If body weight is 1-2kg above target weight -
  Infuse furosemide 10mg bolus at 9am and 5pm.
If body weight is 0-1kg above target weight -
  Infuse furosemide 10mg at 9am.
If body weight is 0-1kg below target weight -
  Infuse furosemide 5mg at 9am.
If body weight is 1-2kg below target weight -
  Hold infusion.
If body weight is 2-3kg below target weight -
  Hold infuison.

Figure 26

<Furosemide infusion rate protocol 6>

If body weight is more than 3kg above target weight -
   Infuse basal rate at 3mg per hour for 8 hours starting at 9am,
   Infuse bolus rate of 30mg at 9am and 4pm.
If body weight is 2-3kg above target weight -
   Infuse basal rate at 2mg per hour for 8 hours starting at 9am,
   Infuse bolus rate of 20mg at 9am and 4pm.
If body weight is 1-2kg above target weight -
   Infuse basal rate at 1mg per hour for 6 hours starting at 9am,
   Infuse bolus rate of 10mg at 9am and 4pm.
If body weight is 0-1kg above target weight -
   Hold basal rate infusion,
   Infuse bolus rate of 10mg at 9am and 4pm.
If body weight is 0-1kg below target weight -
   Hold basal rate infusion,
   Infuse bolus rate of 10mg at 9am.
If body weight is more than 1kg below target weight -
   Hold basal rate,
   Hold bolus rate.

Figure 28

<Furosemide infusion rate protocol 7>

If body weight is more than 4kg above target weight -
  Infuse basal rate at 4mg per hour for 10 hours starting at 8am,
  Infuse bolus rate of 40mg at 8am, 2pm, 8pm.
If body weight is 3-4kg above target weight -
  Infuse basal rate at 3.5mg per hour for 10 hours starting at 9am,
  Infuse bolus rate of 35mg at 9am and 4pm.
If body weight is 2-3kg above target weight -
  Infuse basal rate at 2.5mg per hour for 10 hours starting at 9am,
  Infuse bolus rate of 30mg at 9am and 4pm.
If body weight is 1-2kg above target weight -
  Infuse basal rate at 1.5mg per hour for 8 hours starting at 9am,
  Infuse bolus rate of 20mg at 9am and 4pm.
If body weight is 0-1kg above target weight -
  Hold basal rate infusion,
  Infuse bolus rate of 15mg at 9am and 4pm.

Figure 29

<Low dose Furosemide infusion protocol >

If body weight is more than 2kg above target weight -
   Change the protocol to moderate dose furosemide infusion protocol
   Infuse the dose according to the moderate dose furosemide protocol.
If body weight is 1.5-2kg above target weight -
   Infuse basal rate at 1.5mg per hour for 10 hours starting at 6am,
   Infuse bolus rate of 40mg at 6am and 4pm.
If body weight is 1-1.5kg above target weight -
   Infuse basal rate at 0.5mg per hour for 10 hours starting at 6am,
   Infuse bolus rate of 30mg at 6am and 4pm.
If body weight is 0.5-1kg above target weight -
   Infuse bolus rate of 20mg at 6am and 4pm.
If body weight is 0-0.5kg above target weight -
   Hold basal rate infusion,
   Infuse bolus rate of 10mg at 6am and 4pm.

Figure 33

<Moderate dose furosemide infusion protocol>

If body weight is more than 2kg above target weight -
   Change the protocol to high dose furosemide infusion protocol
   Infuse the dose according to the high dose furosemide protocol.
If body weight is 1.5-2kg above target weight -
   Infuse basal rate at 2mg per hour for 10 hours starting at 6am,
   Infuse bolus rate of 50mg at 6am and 4pm.
If body weight is 1-1.5kg above target weight -
   Infuse basal rate at 0.7mg per hour for 10 hours starting at 6am,
   Infuse bolus rate of 40mg at 6am and 4pm.
If body weight is 0.5-1kg above target weight -
   Infuse bolus rate of 30mg at 6am and 4pm.
If body weight is 0-0.5kg above target weight -
   Hold basal rate infusion,
   Infuse bolus rate of 20mg at 6am and 4pm.

Figure 34

<High dose furosemide infusion protocol>

If body weight is more than 3kg above target weight -
　Infuse basal rate at 4mg per hour for 12 hours starting at 6am,
　Infuse bolus rate of 70mg at 7am, noon, 6pm,
　Instruct patient to take metolazone 7.5mg tablet at 6:30am,
　Instruct patient to contact a physician.
If body weight is 2-3kg above target weight -
　Infuse basal rate at 3mg per hour for 12hours starting at 6am,
　Infuse bolus rate of 65mg at 7am, noon, 6pm,
　Instruct a user to take metolazone 5mg tablet at 6:30am.
If body weight is 1.5-2kg above target weight -
　Infuse basal rate at 2mg per hour for 10 hours starting at 6am,
　Infuse bolus rate of 60mg at 6am and 4pm.
If body weight is 1-1.5kg above target weight -
　Infuse basal rate at 1mg per hour for 10 hours starting at 6am,
　Infuse bolus rate of 50mg at 6am and 4pm.
If body weight is 0.5-1kg above target weight -
　Infuse basal rate at 0.7mg per hour for 10 hours starting at 6am,
　Infuse bolus rate of 40mg at 6am and 4pm.
If body weight is 0-0.5kg above target weight -
　Infuse basal rate at 0.5mg per hour for 10 hours starting at 6am,
　Infuse bolus rate of 30mg at 6am and 4pm.

Figure 35

<furosemide infusion protocol>

If body weight is more than 2kg above target weight and blood pressure is
  above 100/70 -
  Change the protocol to high dose furosemide infusion protocol
  Infuse the dose according to the high dose furosemide protocol.
If body weight is 1.5-2kg above target weight and blood pressure is above
  100/70 -
  Infuse basal rate at 2mg per hour for 10 hours starting at 6am,
  Infuse bolus rate of 50mg at 6am and 4pm.
If body weight is 1-1.5kg above target weight and blood pressure above
  100/70 -
  Infuse basal rate at 0.7mg per hour for 10 hours starting at 6am,
  Infuse bolus rate of 40mg at 6am and 4pm.
If body weight is 0.5-1kg above target weight and blood pressure is above
  100/70 -
  Infuse bolus rate of 30mg at 6am and 4pm.
If body weight is 0-0.5kg above target weight and blood pressure is above
  100/70-
  Hold basal rate infusion,
  Infuse bolus rate of 20mg at 6am and 4pm.
If systolic blood pressure is less than 100, or
  diastolic blood pressure is less than 60,
  hold furosemide infusion and notify a physician

Figure 37

<furosemide and enalaprilat infusion protocol>

If body weight is more than 2kg above target weight and blood pressure is
  above 100/70 -
  Change the protocol to high dose furosemide infusion protocol
  Infuse the dose according to the high dose furosemide protocol.
If body weight is 1.5-2kg above target weight and blood pressure is above
  100/70 -
  Infuse basal rate at 2mg per hour for 10 hours starting at 6am,
  Infuse bolus rate of 50mg at 6am and 4pm.
If body weight is 1-1.5kg above target weight and blood pressure above
  100/70 -
  Infuse basal rate at 0.7mg per hour for 10 hours starting at 6am,
  Infuse bolus rate of 40mg at 6am and 4pm.
If body weight is 0.5-1kg above target weight and blood pressure is above
  100/70 -
  Infuse bolus rate of 30mg at 6am and 4pm.
If body weight is 0-0.5kg above target weight and blood pressure is above
  100/70-
  Hold basal rate infusion,
  Infuse bolus rate of 20mg at 6am and 4pm.
If blood pressure is less than 100/70, hold furosemide infusion and notify a physician If blood pressure is above 160/110, infuse enalaprilat 0.625mg every six hours
If blood pressure remains above 160/110 after enalaprilat 0.625mg infusion,
Increase enalaprilat to 1.25mg every six hours
If blood pressure is less than 100/70, stop enalaprilat
If blood pressure is above 180/120, notify a physician
Send blood pressure and drug dose information to physician's office
  computer system

Figure 38

<furosemide and enalaprilat infusion protocol 2>

If body weight is more than 2kg above target weight and blood pressure is
   above 100/70 -
   Change the protocol to high dose furosemide infusion protocol
   Infuse the dose according to the high dose furosemide protocol.
If body weight is 1.5-2kg above target weight and blood pressure is above
   100/70 -
   Infuse basal rate at 2mg per hour for 10 hours starting at 6am,
   Infuse bolus rate of 50mg at 6am and 4pm.
If body weight is 1-1.5kg above target weight and blood pressure above
   100/70 -
   Infuse basal rate at 0.7mg per hour for 10 hours starting at 6am,
   Infuse bolus rate of 40mg at 6am and 4pm.
If body weight is 0.5-1kg above target weight and blood pressure is above
   100/70 -
   Infuse bolus rate of 30mg at 6am and 4pm.
If body weight is 0-0.5kg above target weight and blood pressure is above
   100/70-
   Hold basal rate infusion,
   Infuse bolus rate of 20mg at 6am and 4pm.
If blood pressure is less than 100/70, hold furosemide infusion and notify a physician If blood pressure is above 180/120, notify a physician
If systolic blood pressure is above 160 or diastolic blood pressure is above 110,
   infuse enalaprilat 1.25mg every six hours
If systolic blood pressure is between 140-160 or
   diastolic blood pressure is between 90-110,
   infuse enalaprilat 0.625mg every six hours
If systolic blood pressure is less than 140 or
   diastolic blood pressure is less than 99,
   hold enalaprilat infusion
If systolic blood pressure is less than 90 or diastolic blood pressure is less than 60,
   notify a user to hold all the antihypertensive drugs and notify a physician Send blood pressure and drug dose information to physician's office
   computer system

Figure 39

```
<furosemide and metoprolol infusion protocol>

If body weight is more than 2kg above target weight and blood pressure is
  above 100/70 -
   Change the protocol to high dose furosemide infusion protocol
   Infuse the dose according to the high dose furosemide protocol.
If body weight is 1.5-2kg above target weight and blood pressure is above
  100/70 -
   Infuse basal rate at 2mg per hour for 10 hours starting at 6am,
   Infuse bolus rate of 50mg at 6am and 4pm.
If body weight is 1-1.5kg above target weight and blood pressure above
  100/70 -
   Infuse basal rate at 0.7mg per hour for 10 hours starting at 6am,
   Infuse bolus rate of 40mg at 6am and 4pm.
If body weight is 0.5-1kg above target weight and blood pressure is above
  100/70 -
   Infuse bolus rate of 30mg at 6am and 4pm.
If body weight is 0-0.5kg above target weight and blood pressure is above
  100/70-
   Hold basal rate infusion,
   Infuse bolus rate of 20mg at 6am and 4pm.
If blood pressure is less than 100/60, hold furosemide infusion and
  notify a physician If systolic blood pressure is above 160 or diastolic blood pressure is above 110
  and heart rate is above 65,
   infuse metoprolol 5mg over 5 minutes every six hours
If systolic blood pressure is less than 160 or diastolic blood pressure is less than 110,
  hold metoprolol
If heart rate is above 130 and systolic blood pressure is above 110,
  infuse metoprolol 5mg over 5 minutes and notify a physician
If systolic blood pressure is less than 100, stop metoprolol
If heart rate is less than 60, stop metoprolol.
If blood pressure is above 180/120, notify a physician
Ask a user if he has chest pain, shortness of breath. If user says yes, instruct a user
  to call 911
Send blood pressure and drug dose information to physician's office
  computer system
```

Figure 40

- <furosemide infusion protocol>

- If body weight is above the target weight, increase basal rate by 0.05mg multiplied by multiples of 100 gram of the difference between target weight and measured weight per hour for 8 hours.
- If body weight is below target weight, decrease basal rate by 0.05mg multiplied by multiples of 100 gram of the difference between target weight and measured weight per hour for 8 hours.
- If body weight is more than 1kg below target weight, hold furosemide infusion.

Figure 45-a

- <furosemide infusion protocol>

- If body weight is above target weight, increase each bolus dose by 1mg multiplied by multiples of 100 gram of the difference between target weight and measured weight.
- If body weight is below target weight, decrease each bolus dose by 1mg multiplied by multiples of 100 gram of the difference between target weight and measured weight.
- If body weight is more than 1kg below target weight, hold furosemide infusion.

Figure 45-b

METHOD FOR CONTROLLING BODY FLUID CONDITION USING DIURETICS, BASED ON WEIGHT MEASUREMENT

CROSS-REFERENCE TO RELATED APPLICATION

This application claims priority under 35 U.S.C. §119(e) to (a) U.S. Provisional Patent Application Ser. No. 60/967,025, "Apparatus and method to control body fluid balance," filed Sep. 1, 2007, (b) U.S. Provisional Patent Application Ser. No. 60/979,634, "Controlling body fluid condition using diuretics," filed Oct. 12, 2007, (c) U.S. Provisional Patent Application Ser. No. 60/986,974, "Controlling body fluid condition using diuretics," filed Nov. 9, 2007, and (d) U.S. Provisional Patent Application Ser. No. 60/988,375, "Controlling body fluid condition using diuretics," filed Nov. 15, 2007, and (e) U.S. Provisional Patent Application Ser. No. 61/048,113, "Controlling body fluid condition using diuretics," filed Apr. 25, 2008. The subject matter of all of the foregoing is incorporated herein by reference in its entirety, including any appendices or attachments, for all purposes.

BACKGROUND OF THE INVENTION

1. Field of the Invention

This invention relates to controlling body fluid condition using diuretics.

2. Description of the Related Art

Body fluid imbalance is associated with many diseases such as congestive heart failure, liver cirrhosis and kidney disease. Congestive heart failure in particular is a major cause of death and hospitalization. Despite currently available treatment, mortality and hospitalization from congestive heart failure remains high. Causes of heart failure include coronary artery disease, hypertension, valvular heart disease, myocardial infarction, etc. As pump function of the heart deteriorates, body fluid often increases and may lead to complications such as pulmonary edema.

When pumping capacity of the heart deteriorates, blood perfusion to the kidneys decreases. This results in retention and accumulation of body fluid because excessive body fluid is not delivered to the kidneys to be excreted. This excessive body fluid often manifests as swelling of the legs. If body fluid continues to expand, a weak heart may be no longer able to handle increased blood volume and finally fails to pump blood forward adequately. Symptoms of congestive heart failure include shortness of breath, fatigue, swelling of legs, orthopnea, paroxysmal nocturnal dyspnea (not being able to breathe suddenly at night). Many people come to the emergency room due to congestive heart failure exacerbation. People do not breathe well when fluid builds up in the lungs.

Diuretics such as hydrochlorothiazide, furosemide and bumetanide are often used to treat this fluid accumulation by increasing the excretion of body fluid and sodium through the kidneys. However, use of oral diuretics often fails to prevent heart failure exacerbation. This failure of diuretics to prevent heart failure can be explained by several mechanisms. First, the dosage of oral diuretics prescribed by the doctor is often fixed, but the ideal dosage often changes depending on changing body conditions. For example, when people with heart disease eat salty food high in sodium content, their body fluid may increase significantly. We often see people come to the emergency room after they eat excessive amount of salt at a party. In this situation, people will require a higher dose of diuretics in order to excrete excessive body fluid and salt. The required dose of diuretics is affected by the dietary intake of sodium, water and tendency to retain sodium. When body fluid builds up in the digestive system, it may cause intestinal edema (swelling). Bioavailability of diuretics may decrease with intestinal swelling. The body may not be able to absorb diuretics effectively. Patients may need to take higher dose of diuretics when poor bioavailability occurs.

Second, poor compliance plays a role. People sometimes forget to take medications. This poor compliance could result in heart failure. Third, treatment delay plays a role. When there is a sign of body fluid accumulation such as swelling of legs, many people ignore this early sign of heart failure and wait until their condition gets severe enough to require hospitalization. These explanations are associated with many cases of heart failure.

Sliding scale diuretic titration of oral diuretics has been attempted for the treatment of congestive heart failure by some heart failure management programs. In sliding scale diuretic titration, patients are instructed to measure body weights and adjust diuretics pill dose according to the instruction given by their physician or nurse. However, conventional diuretic sliding scale titration has several significant drawbacks. First, patients may not understand the sliding scale instruction or may not comply with it. Poor understanding of the instruction may also lead to inappropriate use of medication. Second, conventional instructions may be limited to instructions and sliding scale titration that are simpler than would be desired. In real clinical situations, a more complex diuretic titration may be required to maintain ideal body fluid condition. However, some patients may not be able to follow such complex instructions so instructions may be simplified at the cost of a less effective titration.

In addition, if the sliding scale diuretic titration changes frequently, some patients may not understand the change of sliding scale diuretic titration and may end up taking the wrong dose of medication. This may lead to serious complications. Taking too much medication may lead to complications such as dehydration, electrolyte imbalance, hypotension, and kidney failure. Conventional sliding scale diuretic titration is also limited to oral diuretics, which may not be as effective as, for example, continuous infusion of diuretics.

As a result of these possible complications, sliding scale diuretic titration, when attempted, is typically based on a straightforward and simple protocol. More complex protocols generally have not been attempted because there is not a reliable way to carefully monitor and control the dispensing of diuretic or to adjust the dose according to varying conditions. In addition, there are not reliable safety measures to safeguard against the possible inappropriate use of diuretics. Without such controls and safety measures, more complex protocols can have a higher risk of inappropriate use of diuretics and possible adverse effects such as dehydration, electrolytes abnormalities, hypotension, and kidney failure.

Thus, there is a need for better, and preferably automatic, approaches to control body fluid condition using diuretics.

SUMMARY OF THE INVENTION

One aspect of the present invention overcomes the limitations of the prior art by automatically infusing diuretic into a human patient. In one approach, the rate of infusion of the diuretic is adjusted based on the measured weight of the patient. This weight can be transmitted wirelessly to a portable diuretic infusion device attached to the patient, for example.

In one aspect of the invention, a portable diuretic infusion device includes a reservoir, a pump and a controller. The reservoir can hold a diuretic or an antihypertensive drug to be infused into the patient. The pump is connected to the reservoir and is also connectable to the patient, for example using an infusion set. The pump is operated to infuse diuretic or other drug from the reservoir into the patient. The controller controls the pump, thereby controlling the rate of infusion of the diuretic or other drug.

The controller adjusts the rate of infusion based (at least in part) on a measured weight of the patient. For example, the protocol may be designed to maintain a target weight for the patient, so that more diuretic is infused when the patient is over the target weight and less diuretic is infused when the patient is under the target weight. In another aspect, the patient's weight can be measured and then wirelessly transmitted to the diuretic infusion device. The controller on the diuretic infusion device receives the weight information and automatically adjusts the infusion rate.

In another aspect of the invention, the weight information is not used to automatically control a diuretic pump. Rather, it is used to automatically calculate the correct dose of diuretic and this is displayed to the patient. In one approach, a weight measurement apparatus (e.g., a scale) includes a weight sensor, a processor and a display. The weight sensor measures the body weight of the patient. The processor calculates the corresponding dose of diuretic based on the measured weight. The dose is shown to the patient on the display. It could also be shown on other devices, such as a computer, cell phone, PDA, etc.

In still a further aspect of the invention, the diuretic infusion system includes a biological parameter measurement apparatus with a biological parameter measurement sensor for measuring a (non-weight) biological parameter of a human patient. The diuretic is dispensed based on the weight measurement and the measurement of the additional biological parameter(s).

In other aspects of the invention, the portable diuretic infusion device is a metered dose diuretic infusion pump. This pump can include a reservoir for holding diuretic, and a pump connected to the reservoir and connectable to a human patient for infusing diuretic from the reservoir into the patient.

In further embodiments, the diuretic infusion system is remote control operated. The system can include a weight measurement apparatus having a weight sensor for measuring a body weight of a human patient and a wireless transmitter for wirelessly transmitting weight information based on the measured body weight. The system can further include a portable diuretic infusion device with a reservoir for holding diuretic, a pump connected to the reservoir and connectable to the patient, a controller for controlling the pump, and a wireless receiver for wirelessly receiving commands. The system can also include a remote control device with a wireless receiver for wirelessly receiving the weight information transmitted, a wireless transmitter for wirelessly transmitting one or more commands to the portable diuretic infusion device, and a controlled coupled to the receiver/transmitter for wirelessly controlling the pump and rate of infusion based on weight information. Other embodiments of the diuretic infusion system can include fewer or more components within the weight measurement apparatus, the portable diuretic infusion device, and the remote control device.

Different protocols can be implemented using these devices and systems. For example, the infusion rate can include both basal and bolus components. Diuretic infusion can be supplemented and/or replaced by other delivery mechanisms, such as oral diuretics. Fairly complex protocols can be implemented, since the protocol is more automated and depends much less on the patient implementing the protocol. For example, infusion rate can vary by time of day, thus reducing urination at nighttime. Prospective infusion can also be implemented, for example if heavy salt intake is expected. The infusion rate can also be adjusted based on feedback other than just weight.

These approaches allow the dose of diuretics to be controlled much more carefully than by patient instructions alone, resulting in many possible advantages. For example, early detection and early treatment of various body fluid related diseases may be possible. This can reduce hospitalizations and death from congestive heart failure, pulmonary edema and fluid overload. In addition, patients can now have continuous infusion of diuretics by using a portable, ambulatory infusion pump. Continuous infusion of diuretics may be more effective than bolus use of diuretics. These approaches may also be more effective in maintaining target weight and/or dry weight, compared with using oral diuretics. The automated approach is also easier for patients and allows the implementation of more complex protocols, while also reducing the risk of over- or under-treatment. The automated devices can also record diuretic use (and also body weight), thus providing a reliable medical history. This information can be sent over the internet to the healthcare providers or others, for analysis or remote monitoring of patients.

Other aspects of the invention include methods corresponding to the devices and systems described above, and protocols for use with same.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 1-*a* depicts a diuretic infusion system.

FIG. 1-*b* depicts a wireless diuretic infusion system.

FIG. 4 shows a protocol for use with a diuretic infusion system.

FIGS. 8-*a* and 8-*b* is a mechanical depiction of a diuretic pump.

FIGS. 19-29 show additional protocols for diuretic dispensing.

FIGS. 32-35 show additional protocols for diuretic dispensing.

FIGS. 37-40 show protocols for use with the diuretic infusion system of FIG. 36.

FIGS. 45-a and 45-b illustrate additional drug-infusion protocols

Figure 2:
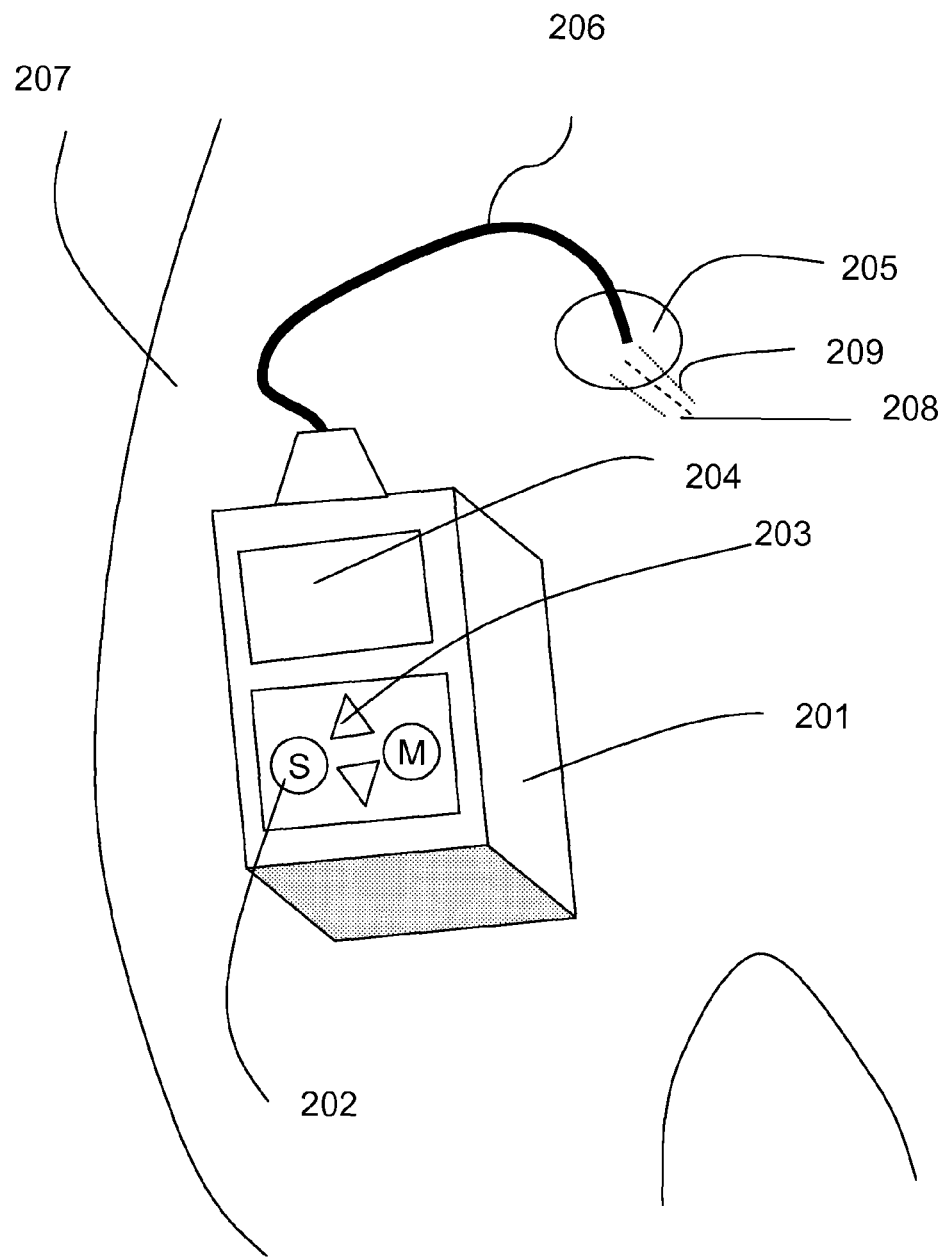
FIG. 2 depicts a more detailed view of a diuretic infusion device.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

FIG. 1-a depicts a diuretic infusion system according to the invention. Diuretic infusion device 101 is located on the patient's body 102. Weight sensor 103 measures the patient's body weight. In one embodiment, the weight sensor 103 is an electric scale. A user inputs measured body weight into the diuretic infusion device 101. The diuretic infusion device 101 delivers diuretic to the human body 102. The dose of the diuretic is determined based on the measured body weight. FIG. 1-b depicts another embodiment. The weight sensor 103 communicates with the diuretic infusion device 101, in this example using a wireless communications channel. Weight information, for example body weight, body weight change, past body weight measurements and/or body weight trends, is transferred from weight sensor 103 to the diuretic infusion device 101 via the wireless communication. The diuretic infusion device 101 uses this information to adjust the rate of diuretics infusion to the patient 102.

Various wireless technologies may be used. Examples include BLUETOOTH™, WiFi, Wimax, other RF (radio frequency) technologies, and infrared and optical technologies. Wireless transmitters and receivers may be built into the weight sensor 103 and diuretic infusion device 101. The sensor 103 and diuretic infusion device 101 may communicate directly with each other, or through intermediary devices such as a remote control device, a separate computer system (for example, accessible by the patient and/or his healthcare professional). The computer system may save information from weight sensor 103 and/or diuretic infusion device 101 to allow further analysis.

In one implementation, the weight sensor 103 is activated by the patient (e.g., by stepping onto a scale), and patients who tend to accumulate body fluid due to heart disease, kidney disease or liver disease are instructed to measure body weight frequently using the weight sensor 103. In an alternate embodiment, the weight sensor may be located so that it is automatically activated. For example, the weight sensor may be located in the patient's bed or as part of a chair that the patient uses regularly. The weight sensor 103 and/or diuretic infusion device 101 may also obtain other types of relevant information, such as the time of day of the weight measurement. In this way, weight measurements can be time stamped and the time stamp may be used to account for cyclical variations in body weight.

Body weight measurements may also be tagged with the patient's identification so that multiple patients can conveniently use the same weight sensor 103. In one approach, the diuretic infusion device 101 or other device 101 identifies the patient to the weight sensor 103, which then tags the weight information with the patient's identification. Alternately, the weight sensor 103 may broadcast the weight information, and the diuretic infusion device 101 has the responsibility to associate the weight information with the correct patient.

Various diuretics may be used with the diuretics infusion device. Examples include hydrochlorothiazide, chlorothiazide, chlorthalidone, metolazone, furosemide, bumetanide, ethacrynic acid, torsemide, spironolactone, indapamide and eplerenone. Vasopressin receptor antagonist may also be used. Examples include conivaptan, tolvaptan. Brain natriuretic peptide may also be used. One example is nesiritide.

FIG. 2 is a close-up of the diuretic infusion device 101 of FIG. 1. In this example, the diuretic infusion device 101 is a diuretic pump 201 that is attached to the body 207. A preferred location is around the body waist and abdomen. The size of the diuretic infusion pump can vary. In one implementation, the diuretic pump is 2.2×3.7×1 inches. This diuretic infusion pump 201 includes a wireless communications chip, processing module, batteries and processor (see FIG. 7 for further detail). The diuretic infusion pump 201 may not include the wireless communications chip in alternative embodiments.

An external keypad to allow the user to program an onboard processor. The onboard processor controls the rate of diuretic infusion. Various buttons 202, 203 are used for various functions, such as programming the diuretics pump and adjusting the diuretic infusion rate. Information such as rate of diuretic infusion, name of diuretics in use, weight information, and optimal or target weight, can be displayed on the screen 204. This screen also shows signals that indicate malfunction of the device and other signals such as time to change a diuretics cartridge or time to change a battery.

This diuretic infusion pump 201 includes a disposable reservoir or a disposable cartridge for the diuretic. The pre-filled cartridge containing diuretics is replaced when empty. In alternative embodiments, the reservoir and/or cartridge may not be disposable. Instead, the reservoir may be refilled when empty.

A disposable infusion set for the diuretic infusion pump may include a cannula 209, an adhesive pad 205, a needle 208 and tubing system 206 (that delivers the diuretic reservoir to a user). The user inserts the needle 208 together with the cannula 209 under the skin. The needle 208 may be removed, leaving the cannula 209 under the skin. Preferably, the tip of the cannula 209 is located at the subcutaneous tissue. Alternatively, the tip of cannula 209 may be located in the abdominal cavity, intramuscular space, intravascular space or peritoneal cavity. The cannula 209 may be made with biocompatible materials such as polyethylene.

Figure 3:
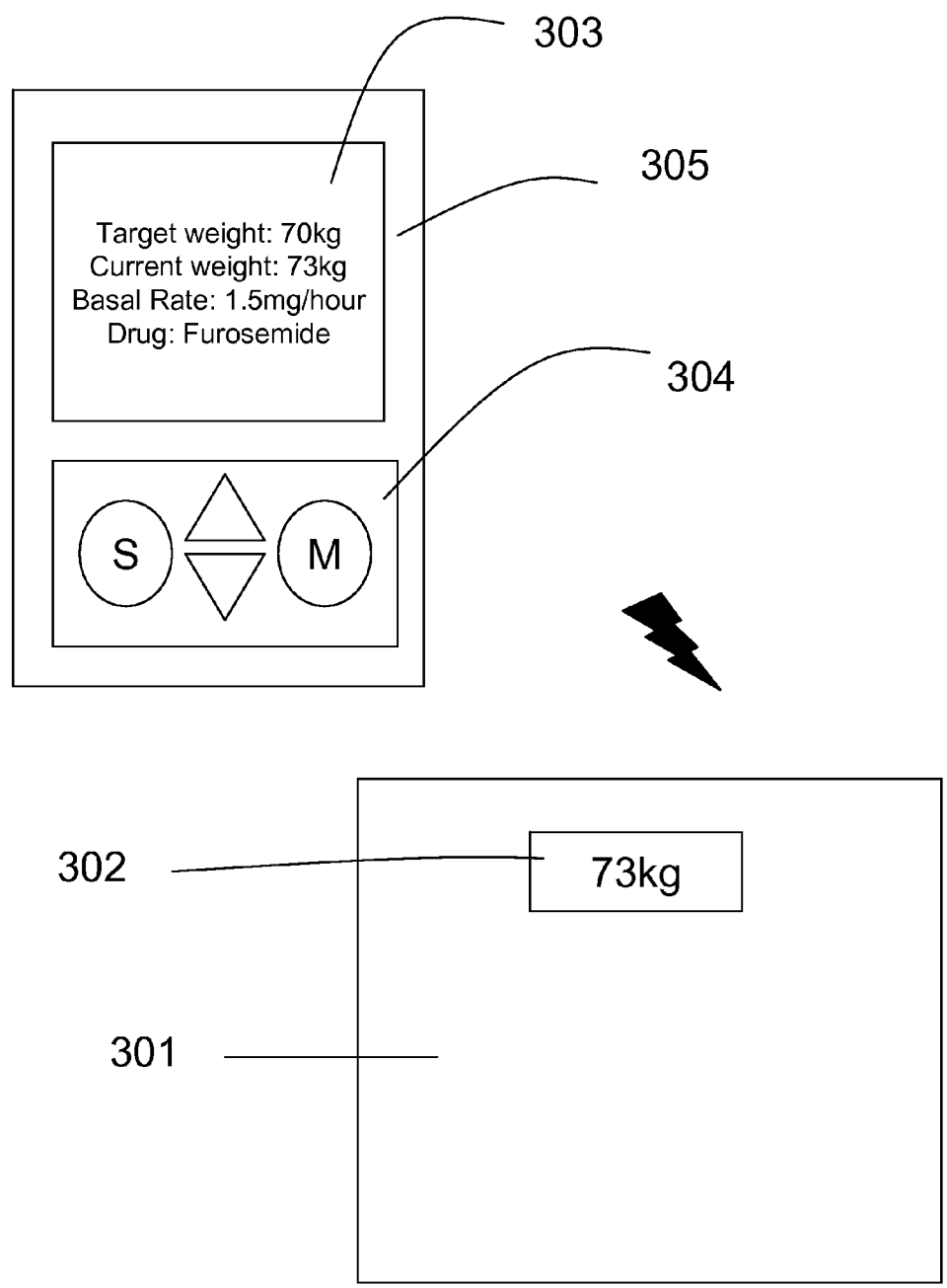
FIG. 3 illustrates operation of a diuretic infusion system.

FIG. 3 illustrates operation of a diuretic infusion system. Screen 303 on the diuretic infusion pump 305 displays information related to use of the diuretic infusion pump. Dry weight or target weight is an important parameter which is often used in clinical settings. At dry weight or target weight, patients likely do not have signs of volume overload such as swelling of legs or shortness of breath. When weight is above dry weight or target weight, this may indicate there is excessive fluid inside the body. When weight is below dry weight or target weight, this may indicate a patient is dehydrated. Maintaining body weight near dry weight or target weight may be effective in preventing heart failure exacerbation due to body fluid overload.

This figure illustrates a patient whose weight is 73 kg, 3 kg above the target weight of 70 kg. Weight measurement apparatus 301 also displays the weight of the user on the screen 302. This body weight is transmitted from the weight measurement apparatus 301 to diuretic infusion pump 305 via wireless communications. Once the diuretic infusion pump 305 receives a signal from the weight measurement apparatus 301, the weight information is decoded. Software coupled with the processor controls at least in part, the operation of the diuretic infusion pump. More than one processor may be used to control the diuretic infusion system. A pumping system controls the transfer of diuretics from a reservoir or a diuretic cartridge to the tubing system and a cannula.

The pumping system is controlled by a processor. In FIG. 3, diuretic infusion pump 305 displays that target weight is 70 kg and current weight is 73 kg. Software is programmed to calculate a corresponding diuretics continuous infusion rate and bolus rate. In this example, the diuretic infusion pump is programmed to increase the diuretics infusion rate in order to increase excretion of body fluid and urine output. The previous basal rate was set at 1 mg per hour. FIG. 3 shows that the basal infusion rate is increased from 1 mg per hour to 1.5 mg per hour.

The user preferably is instructed to measure weight frequently and on a regular basis. At a later weighing, if the body weight is still above target weight but less than weight on the previous measurement, the same infusion rate of diuretics may be programmed to continue. If the body weight returns to the target weight, the infusion rate of the diuretic infusion pump may be programmed to decrease to prevent dehydration.

Various protocols on diuretics infusion can be programmed and/or stored in the processor onboard the diuretic pump, as will be described in more detail below. This is advantageous compared to a conventional approach where a doctor gives instructions to the patient, because patients often do not follow these instructions and more complex protocols can be carried out by the diuretic pump than by most patients.

Buttons on the keypad 304 of the diuretic infusion pump can be used to program an onboard processor and adjust settings on a diuretic infusion pump. The diuretic infusion pump may also be programmed by using a computer system such as a desktop computer, a portable computer, a portable phone or a remote control.

FIG. 4 shows a protocol for use with a diuretic infusion system. In order to maintain body weight at the previously set target weight or dry weight, the diuretic infusion pump adjusts the diuretics infusion rate, which likely changes urine output. Examples for two commonly prescribed diuretics—furosemide and bumetanide—are illustrated. Referring to FIG. 4, the weight measurement sensor measures body weight. This information is transmitted wirelessly to the diuretic infusion pump.

The onboard program of the diuretic infusion pump calculates the difference between target weight and current weight. If the measured body weight is more than 3 kg above target weight (which may suggest there are approximately 3 kg of extra water inside a body), the diuretic infusion pump is programmed to increase the basal rate of diuretics infusion by 100% from the initial basal rate to increase urine output and excrete excess water and salt. If the measured body weight is 2-3 kg above target weight, the diuretic infusion pump is programmed to increase the basal rate of diuretics infusion by 75% from the initial basal rate to increase urine output. If the measured body weight is 1-2 kg below target weight, this may suggest dehydration. The diuretic infusion pump is programmed to decrease the basal rate of diuretics infusion by 75% from the initial basal rate. The basal rate is the continuous infusion rate of a diuretic medication that may be set by a doctor or a user. Bolus is rapid infusion of a diuretics medication to expedite the effect to increase urine output rapidly by increasing drug concentration level in the blood. The diuretic infusion pump may be programmed to use both basal rate and bolus, or to use only one infusion method, either basal rate or bolus.

Conventional methods and technologies for basal infusion and bolus infusion may be used. If the patient does not want to carry the diuretic infusion pump constantly, this patient may choose bolus infusion method only. This user may remove the diuretic infusion pump after bolus infusion and reinsert it when diuretic needs to be infused. An alarm may sound to notify a user when it is time to infuse drug. A user may want to use basal infusion until a certain time of day (like in the evening) for lifestyle purpose. If basal infusion of furosemide stops at 7 pm for example, the effect of furosemide may stop around 10-12 pm. This method may help patients to avoid urinating in the middle of the night, which is a common problem for people who take oral diuretic pills at night. The diuretic infusion pump may be programmed by using software built in the diuretic infusion pump and/or by using software in a separate computer that communicates with the diuretic pump via a wireless communication or non-wireless communication (using a cradle, port, cable, etc).

One example of a case is as follows. A doctor may program a diuretic infusion pump as follows:
Diuretics—furosemide (10 mg/ml)
Initial basal rate—1 mg per hour
Duration of basal rate—start at 7 AM and end at 7 PM
Maximum basal rate—5 mg per hour
Bolus infusion—10 mg over 10 minutes at 7 AM and 4 PM
Maximum bolus infusion per each infusion—60 mg
Maximum daily dose combining basal rate and bolus—200 mg
Target weight—70 kg.
If body weight is more than 3 kg above target weight, increase basal rate by 100% from initial basal rate and provide bolus infusion of 40 mg at 7 AM and 4 PM.
If body weight is 2-3 kg above target weight, increase basal rate by 75% from initial basal rate and provide bolus infusion of 30 mg at 7 AM and 4 PM.
If body weight is 1-2 kg above target weight, increase basal rate by 50% from initial basal rate and provide bolus infusion of 20 mg at 7 AM and 4 PM.

If body weight is 0-1 kg above target weight, increase basal rate by 25% from initial basal rate and provide bolus infusion of 10 mg at 7 AM and 4 PM.

If body weight is 0-1 kg below target weight, decrease the basal rate by 50% from initial basal rate and provide bolus infusion of 5 mg at 7 AM.

If body weight is 1-2 kg below target weight, decrease the basal rate by 75% from initial basal rate and hold bolus infusion.

If body weight is more than 2 kg below target weight, stop basal rate and bolus infusion and instruct a user to contact his/her doctor.

Let's say a patient measures his weight on a weight measurement apparatus and finds out that his weight is 3.1 kg above the previously set target weight of 70 kg. Following the programmed furosemide protocol shown on FIG. 4, the diuretic infusion pump increases its basal rate from 1 mg per hour to 2 mg per hour and provides 40 mg furosemide at 7 AM and 4 PM as a bolus infusion. Bolus infusion is programmed to be infused over 10 minutes. The duration of bolus infusion may be adjusted using the keypad. Maximum basal and bolus rate may be set and may be adjusted by a user. This maximum rate may be set as upper limit of daily diuretics dose, upper limit of bolus diuretics dose per each infusion, upper limit of basal rate, and/or upper limit of weekly diuretics dose. Setting these limits of diuretics infusion dose may help to minimize side effects of diuretics such as dehydration, electrolytes imbalance like hypokalemia, hypotension and kidney failure.

In certain embodiments, the diuretic infusion device has the capacity to deliver 0-10 ml/hour in basal rate and up to 40 ml per bolus of furosemide (10 mg/ml). Alternatively, the diuretics infusion device may use other diuretics such as bumetanide, torsemide, ethacrynic acid, chorothiazide, other concentrations, other diuretics and other classes of medications as previously mentioned. In an alternate embodiment, the diuretic infusion device has the capacity to deliver 0-10 ml/hour in basal rate and up to 10 ml per bolus of bumetanide (1 mg/ml). In another embodiment, the diuretic infusion pump may have a capacity to deliver 0-20 ml/hour in basal rate and up to 40 ml per bolus of furosemide (10 mg/ml). In alternative embodiments, different basal rate ranges and different bolus rate ranges may be used.

Figure 5:
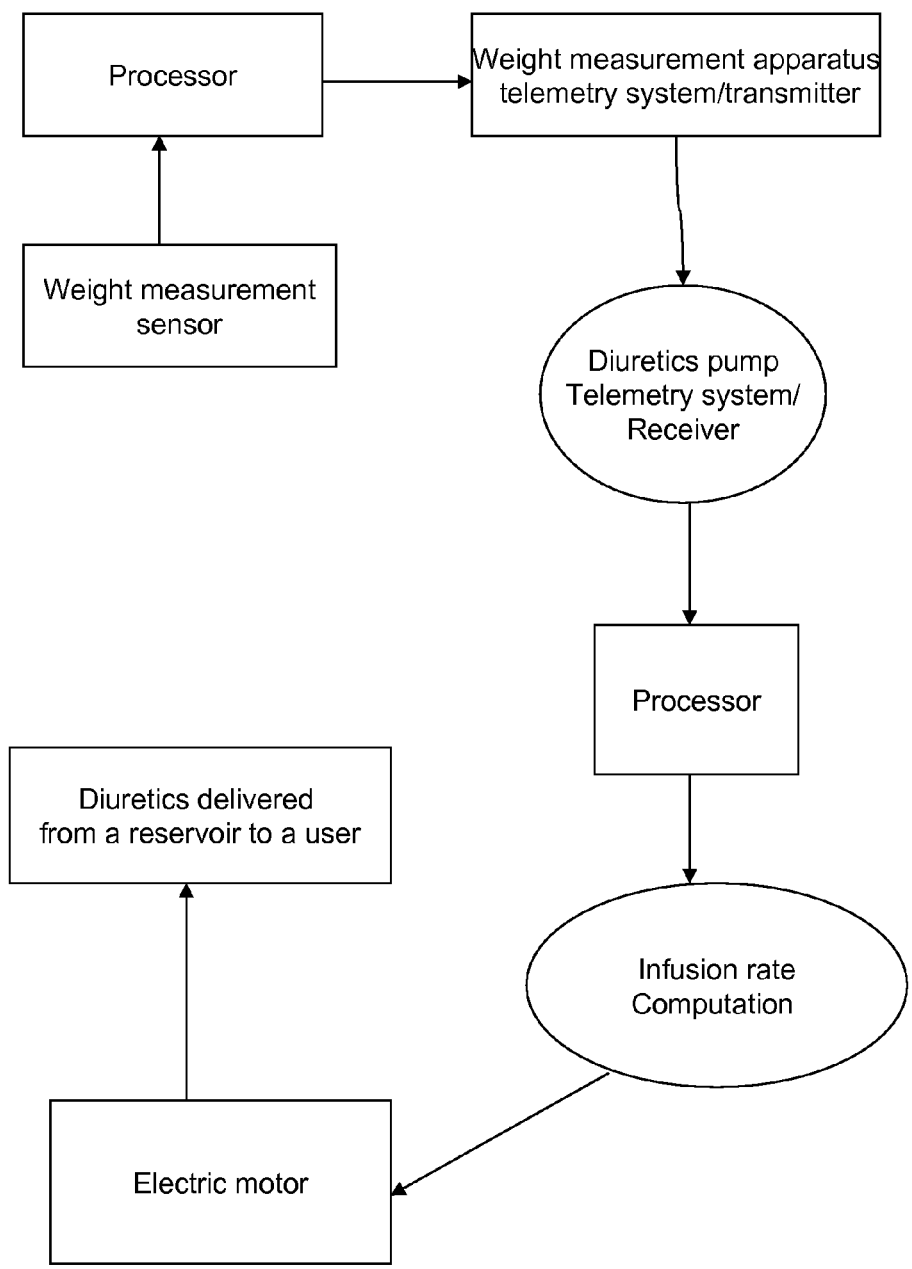
FIGS. 5 and 6 illustrate operation of a diuretic infusion system.
Figure 6:
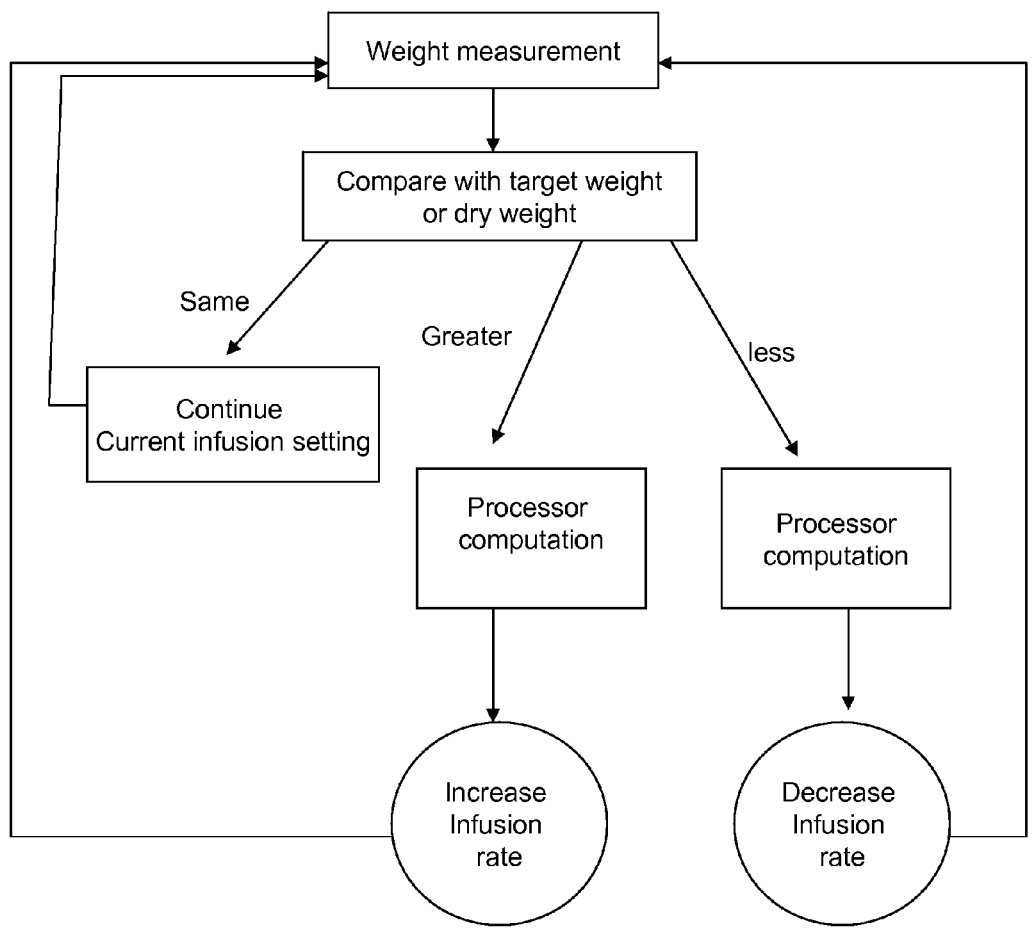

FIGS. 5 and 6 illustrate operation of a diuretic infusion system. In FIG. 5, the weight measurement sensor and processor are onboard within a housing of a weight measurement apparatus. The weight measurement sensor is electrically connected to the processor and sends the measured weight to the processor. The processor is connected to a telemetry system and a signal transmitter. The weight information is sent from the telemetry system of the weight measurement apparatus via the transmitter.

The weight signal is received by a receiver of the diuretic infusion pump. The receiver of the diuretic infusion pump is electrically connected to a processor which is housed in the diuretic infusion pump. The processor receives the weight information and performs computations to determine diuretic infusion rate such as basal rate and bolus rate according to programmed parameters, protocols and algorithms. The processor controls an electric motor to deliver diuretic from a reservoir to a user through an outlet, a tube and an infusion set of the diuretic infusion pump. In an alternative embodiment, a user manually inputs measured weight into a diuretic infusion device. This weight information enters a processor which is housed in the diuretic infusion pump. The processor performs computations to determine diuretic infusion rate in a manner similar to that described above.

In FIG. 6, if the measured weight is same as the target weight, the processor controls the electric pump to continue the current diuretic infusion rate. If the measured weight is different from the target weight, the program determines if the measured weight is greater or less than the target weight. If the measured weight is greater than the target weight, the processor computes the diuretic infusion rate according to its program and increases the rate of diuretic infusion. If the measured weight is less than the target weight, the processor computes the diuretic infusion rate according to its program and decreases the rate of diuretic infusion. The target weight may be the same as dry weight or different from dry weight, depending on the user.

Figure 7:
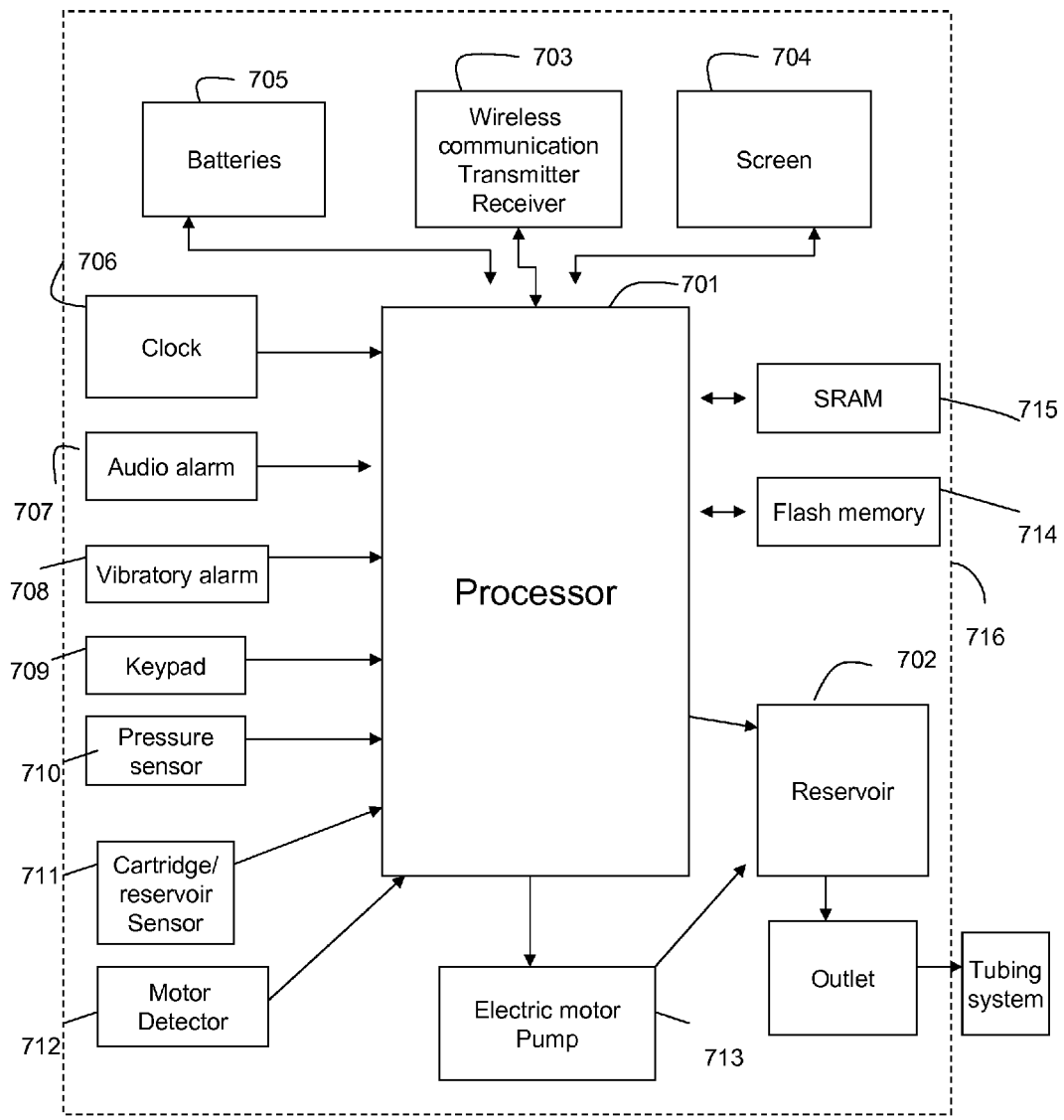
FIG. 7 is a block diagram of a diuretic pump.

FIG. 7 is a block diagram of a diuretic pump. Processor 701 (the controller) is contained in the interior of the housing 716 of the diuretic infusion pump. The housing 716 may be made of plastic or steel, for example. Processor 701 runs software programs and controls components of the diuretics infusion pump. The FREESCALE™ DRAGONBALL™ microprocessor is one example of a processor that may be used. The MOTOROLA™ 6805 is another example. The FREESCALE™ MC9S08RX32A is another example. The MC9S08RX32A includes an RF integrated circuit and microcontrollers (MCU). Other processors that are used in insulin pumps may also be used.

The processor 701 is in electrical communication with an electric motor and pump 713. The processor controls the electric motor 713 according to its program. The processor also controls a screen 704, an audible alarm 707, vibratory alarm 708 and telemetry system. Weight information that is transmitted from the weight measurement apparatus is received by the telemetry system of the diuretic infusion pump. It then enters the processor 701. Alternately, weight information may be input into the diuretic infusion pump manually by a user, for example from a keypad or a remote controller.

In this example, flash memory 714 and SRAM 715 are used for memory storage. This memory may store information such as pump settings, a historical log of weight, malfunctions of the pump, infusion rate, a historical log of infusion rate, medication, etc. In one design, the RAM has 100 kilobytes, ROM has 4 megabytes and flash memory has 4 megabytes memory. Alternate memory media include RAM, ROM, EPROM, DRAM, hard-drives and other types of flash memory.

The user may program the processor 701 using a keypad (or other user interface) on the diuretic infusion pump. In alternative embodiments, a user may use a remote controller or a computer station to program the processor 701.

Information and commands from other computers, portables devices such as PDAs (personal digital assistant), handheld computers, portable phones, remote controllers and the internet may be received through receiver 703. Examples of wireless technologies include radio frequency (RF), infrared (IR) and optical. Specific technologies include BLUETOOTH™, DECT, ZigBee, NFC, GSM, UWB, UMTS, DAB, CDMA, WiFi and WIMAX. Wired communications ports can include Universal Serial Bus (USB) ports and/or RS-232 ports, as well as other technologies.

The diuretic infusion pump displays on its screen whether new weight information, command, or alerts are received. The diuretic infusion pump, weight measurement apparatus, corresponding computer systems and/or remote controller may be assigned a unique identifier and/or password to provide privacy for its users.

In FIG. 7, a keypad 709 is located on the housing 716. A touch screen input device may also be used. The keypad 709 shown in FIG. 2 includes buttons 203, 202 to provide input to the processor 701.

Various other inputs, such as various types of sensors, may also be included in the diuretic infusion pump (or communicate to the diuretic pump from other parts of the system). For example, motion detection sensor 712 may be used to detect the motion of a gear in the drive mechanism for the pump. Cartridge sensor or reservoir sensor 711 may be used to detect the amount of diuretic left within a cartridge or reservoir, and to notify a user when a new cartridge is required or a reservoir requires refilling.

In one embodiment, LCD is used as a screen. Feedback from the weight measurement apparatus, a computer, a remote control device as well as diuretic infusion pump status and programming changes may be displayed on a LCD screen. Time, name of drug, dose of drug used during a particular period of time, reservoir or cartridge usage and history may also be displayed.

A speaker can be used to send audio feedback. A user may choose to use a vibratory alarm instead of audible alarm. For example, if measured body weight is too low or too high, an audible or vibratory alarm may warn a user. If measured body weight is lower than a set value, a certain instruction such as "Drink more water and eat more because you may be dehydrated" may be shown on the screen or played through the speaker. When measured body weight is higher than a set value, certain instructions may be expressed, such as "Calibrate your weight measurement scale" or "Call your doctor if you feel shortness of breath." Alarms may also be activated for pump malfunction, low battery, dead battery, occlusion of infusion set, near-empty cartridge (or reservoir), pump delivery error, if bolus is changed, if mode is changed, if pump is not primed, if infusion exceeds maximum limits, etc.

The diuretic infusion pump preferably uses a AAA alkaline battery. More than one AAA alkaline batteries may be used. Alternatively, different types of batteries may be used such as nickel cadmium battery, nickel metal hydride battery, lithium ion battery, carbon battery, lithium battery and 3.6V lithium battery. The battery may be included inside the housing 716 of the diuretic infusion pump.

Not all embodiments require all of the components described above.

FIGS. 8-a and 8-b are mechanical depictions of a diuretic pump. The diuretic infusion pump contains a processor 801. The processor is electrically connected or otherwise communicatively coupled to an electric motor 802, for example a DC motor with gear-reducer. The processor 801 controls the electric motor 802 according to its programming. The electric motor 802 is connected to a peristaltic pump 804. The peristaltic pump 804 has a rotor inside. A flexible tube inside the peristaltic pump 804 is connected with a tube 805 and 808. The flexible tube is in contact with the rollers. When the rotor turns, one or more rollers squeeze and release the flexible tube to deliver drug from a reservoir 803 to a user via the infusion tube 808. In order to detect if the diuretics solution is depleted and needs to be replaced or refilled, a sensor 809 can be used. FIG. 8-b is a simplified mechanical depiction of a syringe pump system. The pump housing 815 contains a syringe 816. The syringe 816 contains diuretics. The processor 810 is electrically connected or otherwise communicatively coupled to an electric motor 811. The processor 810 controls the electric motor 811 according to its programming. The motor 811 rotates a motor gear which moves a screw 813 axially. A screw 813 is configured to move axially to push a plunger 814 inside a syringe and push diuretics out of a syringe 816 or a reservoir through an infusion tube 818 and a cannula 819. The plunger mechanism transfers the diuretics solution from a diuretics cartridge or reservoir through an outlet of the housing to the patient via tubing system 805, 808 and the infusion set. Technologies used in insulin pumps may be used also for diuretic pumps.

In alternative embodiments, more than one type of drug may be used in the diuretic infusion pump. A processor may be coupled with more than one program, software, protocols and/or parameters that are tailored according to the specific drug that is used. The diuretic infusion pump may automatically recognize the inserted drug. Drug reservoir or cartridge may have a unique identification code. One example of a drug name recognition method is to decode the bar code of the drug name, which is attached on the reservoir or cartridge. Alternatively, the name of the inserted drug may be manually put into the diuretic infusion pump using the keypad which can select alphabets on the screen.

Examples of medications that may be contained in the reservoir 807 or cartridge include hydrochlorothiazide, chlorothiazide, chlorthalidone, metolazone, furosemide, bumetanide, ethacrynic acid, torsemide, spironolactone, eplerenone, vasopressin receptor antagonists, conivaptan, tolvaptan, brain natriuretic peptide, and nesiritide.

Figure 9:
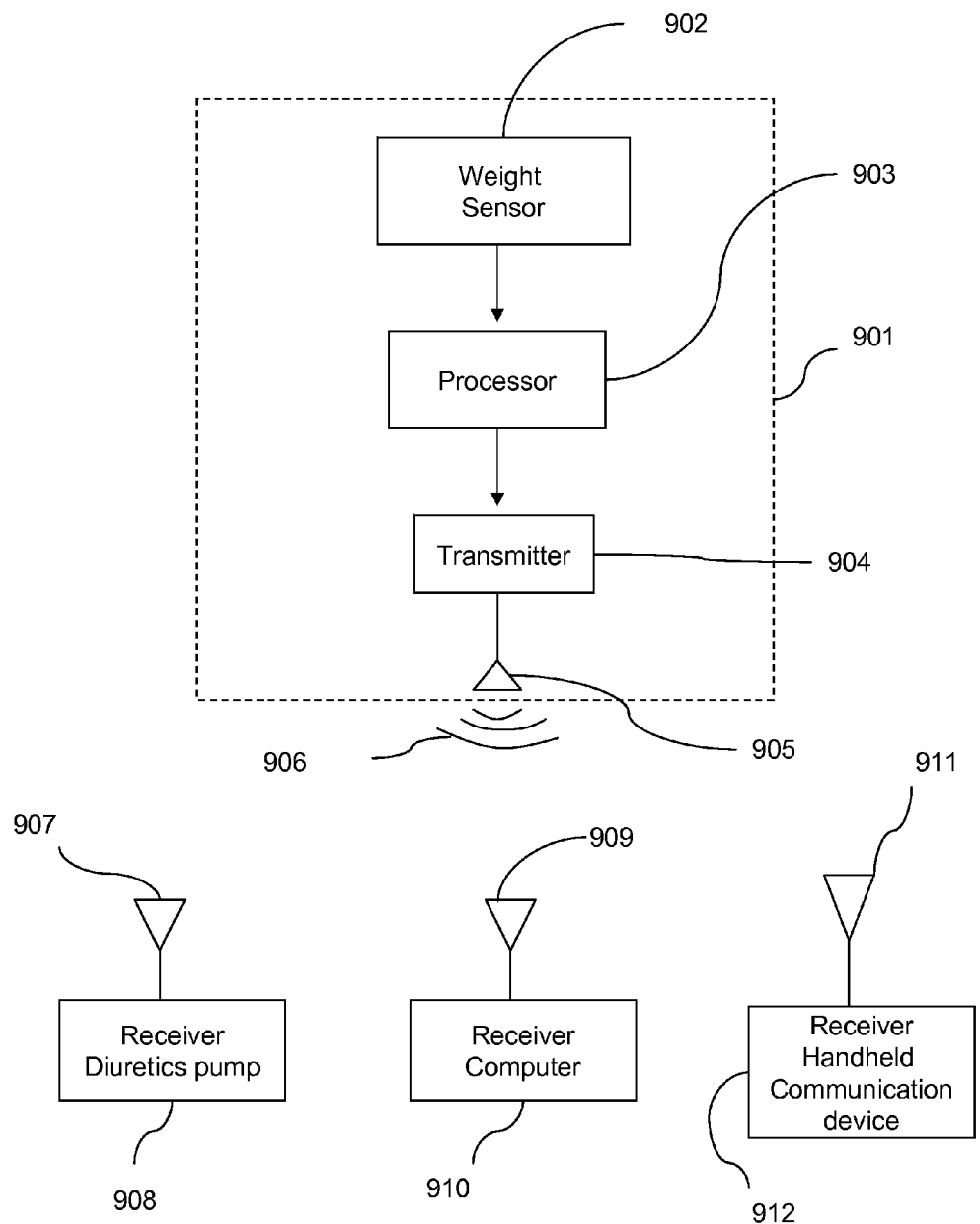
FIG. 9 illustrates wireless operation of a diuretic infusion system.

FIG. 9 illustrates wireless operation of a diuretic infusion system. The weight sensing apparatus 901 includes a weight sensor 902, a processor 903, and a wireless transmitter 904 (or wireless receiver) and antenna 905. The transmitter 904 sends signals 906 that contain weight information.

The weight signal may be sent to different receivers. Diuretic infusion pump receives the signal 906 through an onboard receiver 908 via an antenna 907. A computer such as a home (or physician office) desktop computer or portable computer may receive the signal 906 through an onboard receiver 910 via antenna 909. A handheld communication device such as an iPod, MP3 player, handheld computer, remote control device, or portable phone may receive the signal 906 through onboard receiver 912 via an antenna 911. A user may choose to send information to a computer or handheld communication device for the purpose of saving weight information into the computer or connecting with the internet to send weight information to healthcare providers.

Figure 10:
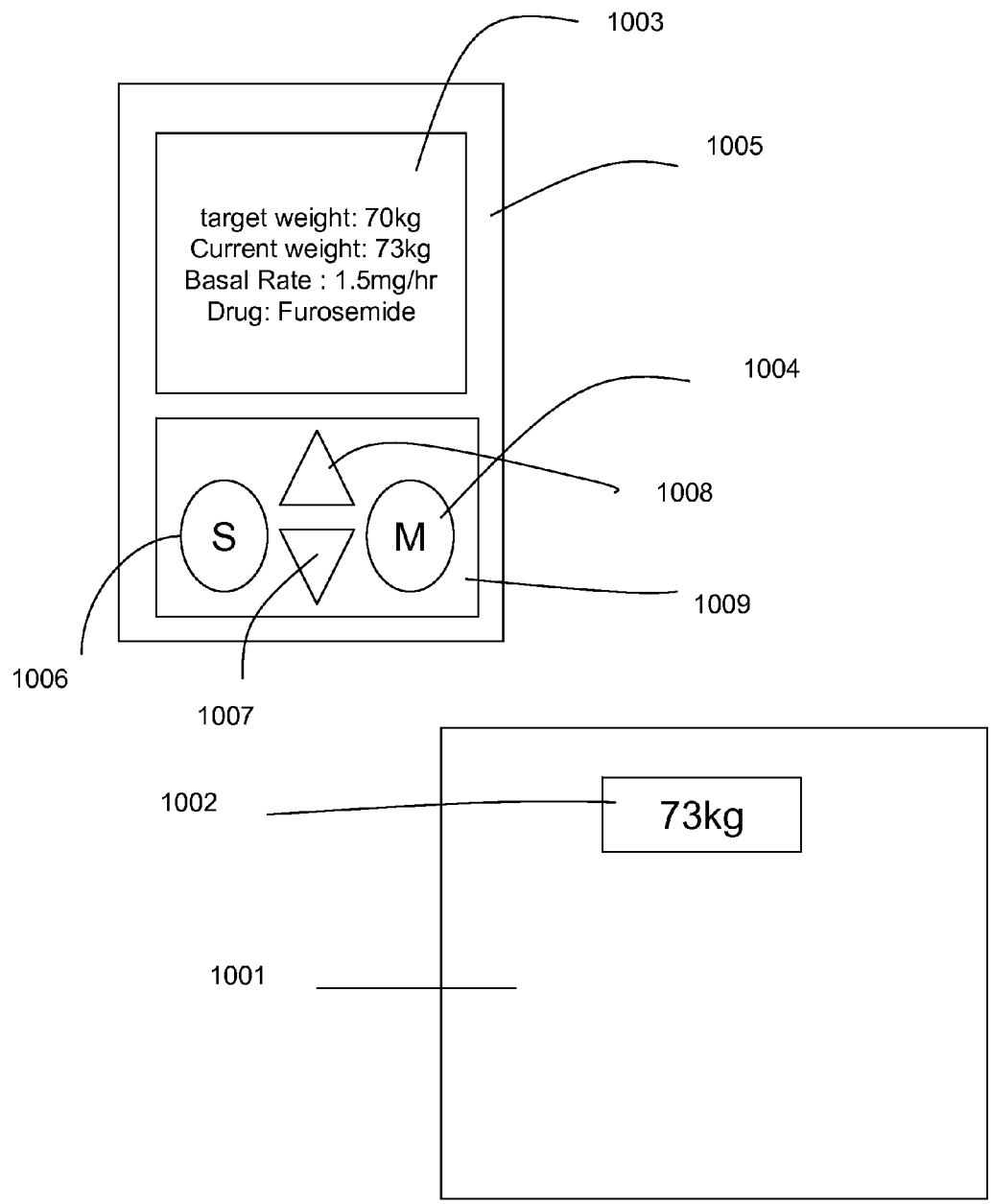
FIG. 10 illustrates operation of a non-wireless diuretic infusion system.

FIG. 10 illustrates operation of a non-wireless diuretic infusion system. In this embodiment, there is no wireless communication between diuretic infusion pump 1005 and a scale 1001. Instead, a user weighs his weight using the scale 1001. The user manually inputs the measured weight into the diuretic infusion pump using a keypad on the diuretic infusion pump (or other input device). In this example, the measured weight (73 kg) on the scale 1001 is shown on the display 1002. The user inputs 73 kg into the diuretic infusion pump weight using the keypad.

The keypad 1009 may have various buttons which are used for particular functions and programming. For example, button 1006 has "S" sign on it and it is used to select a particular menu, number, letter, protocol, medication etc. Button 1004 has "M" sign on it and it is used to show menus, protocols, numbers, letters, medications, etc on the screen 1003 that can be selected using the "S" button. Buttons 1007 and 1008 are used to scroll menus, protocols, numbers, letters and medications up 1008 or down 1007.

In addition to processor control of the infusion rate, the user may be able to adjust the infusion rate manually using the keypad. If the user wants to increases infusion rate more than what is recommended or programmed by the program, or if the user wants to decrease infusion rate less than what is recommended or programmed by the program, the user manually adjusts the rate using the M button 1004, scroll buttons 1007, 1008 and/or S button 1006.

Figure 11:
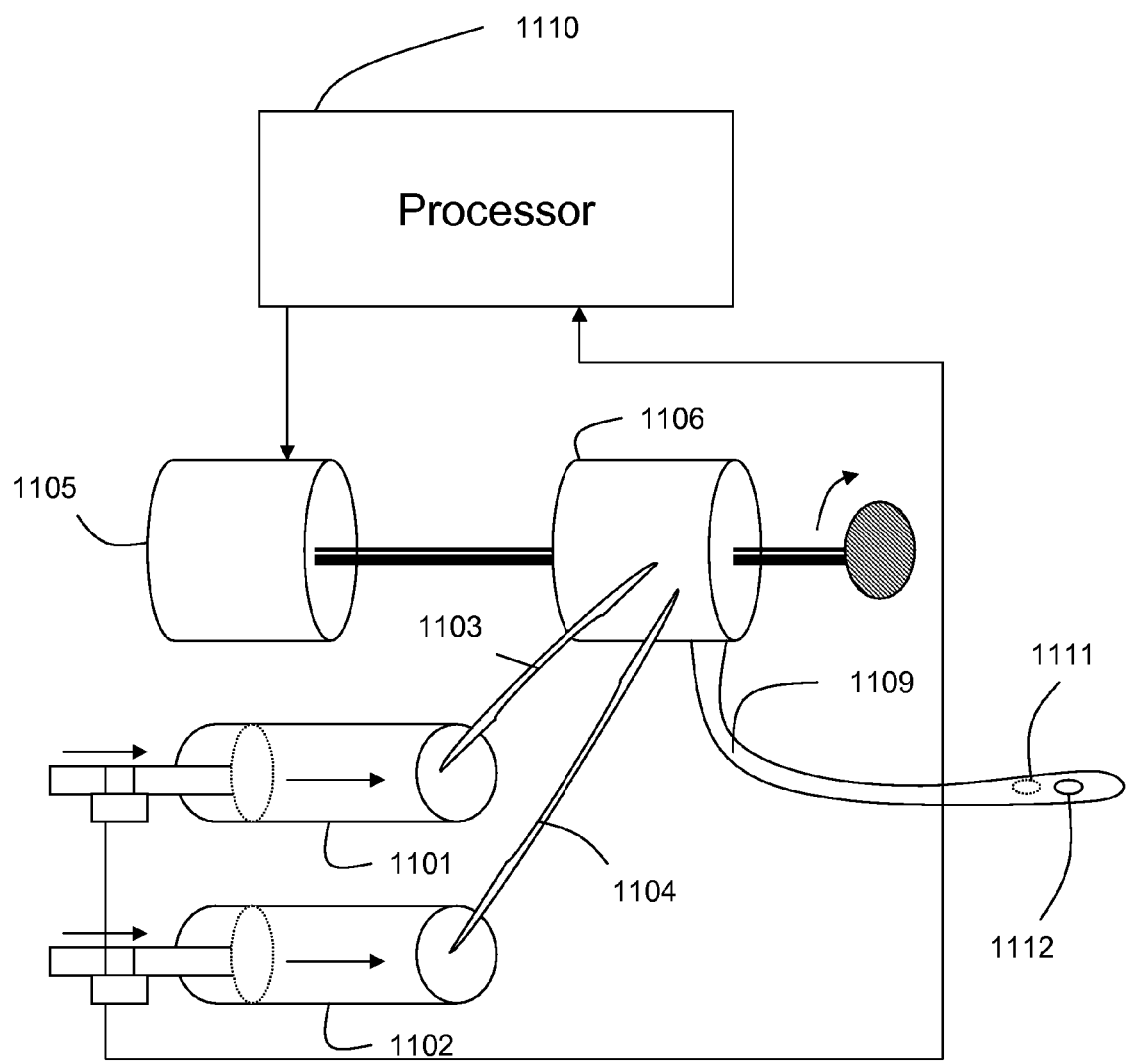
FIG. 11 is a mechanical depiction of a diuretic pump with two reservoirs.

FIG. 11 is a mechanical depiction of a diuretic pump with two reservoirs: in this case a diuretics reservoir 1101 and an insulin reservoir 1102. Patients with diabetes may also have congestive heart failure. This device delivers both diuretics and insulin using one ambulatory infusion pump. In embodiments that use two reservoirs, each medication is delivered via tubes 1103, 1104 inside an ambulatory infusion pump and leaves the housing of the pump via a tube 1109 outside the ambulatory infusion pump. There may be two separate channels within the tube 1109 through which each medication is delivered separately. Each medication is delivered to a user through different holes 1111, 1112. In alternative embodiments, a syringe pump system can be used instead of a peristaltic pump 1106. Two syringes can have separate electric motors that control the movement of the plunger of the respective syringes and release of each medication.

Some medications may not be compatible each other so these medications may need to be delivered through separate channels. More than two medications, channels and holes may be used in alternative embodiments. A processor 1110 controls an electric motor 1105 and a pump 1106 according to its program. More than two electric motors and pumps may be used in alternative embodiments. A separate electric motor and pump may be used to deliver different medications in alternative embodiments.

Figure 12:
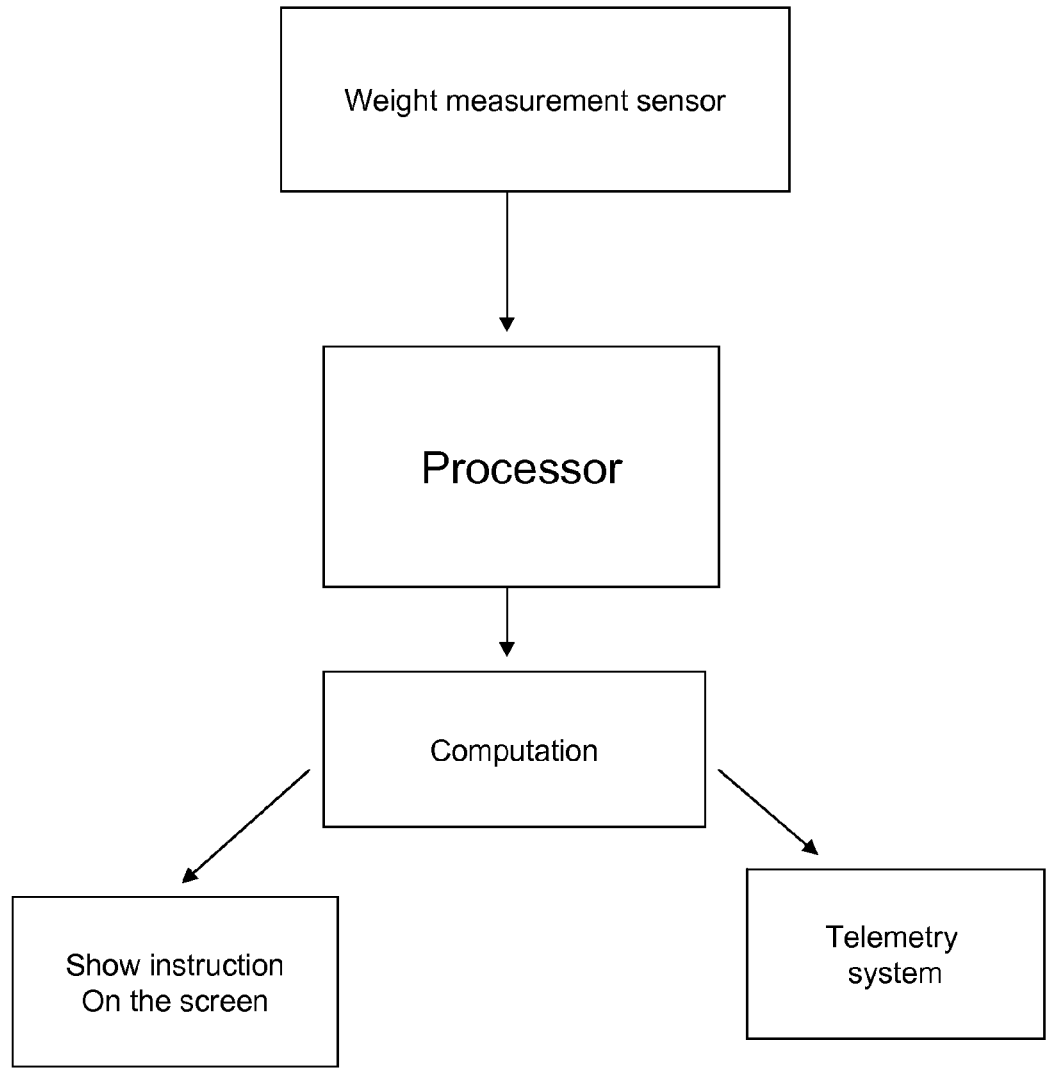
FIGS. 12 and 13 illustrate diuretic dispensing without a diuretic infusion device.
Figure 13:
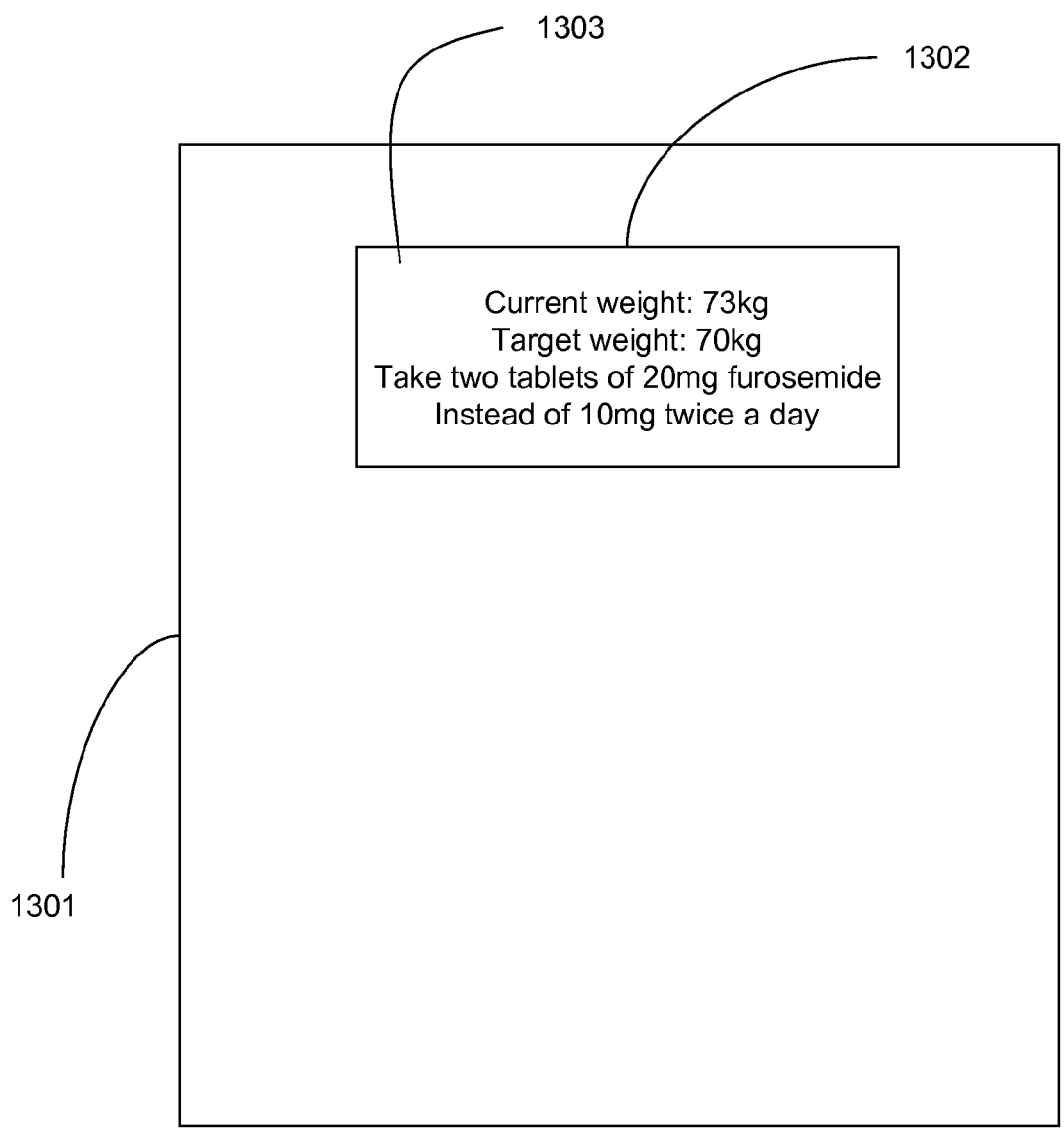

FIGS. 12 and 13 illustrate diuretic dispensing without a diuretic infusion device. Here, a user takes diuretic pills according to displayed instructions on the screen of the scale or separate display device. A weight measurement sensor detects the weight of the user. This weight measurement sensor is electrically connected to a processor. The processor computes a diuretic pill dosage according to its program. Instructions 1303 are displayed on a screen 1302 of the electric scale 1301, as shown in FIG. 13. A separate display device may contain a wireless communication chip, a transmitter/receiver, and a processor, and may perform the computation of drug dosage when weight information enters the processor.

In this example, the measured weight is 3 kg above the target weight of 70 kg. The processor computes the diuretics pill dosage and displays instructions on the screen to increase the dose of furosemide from 10 mg twice a day to 20 mg twice a day. An example protocol is the following:
  If body weight is more than 2 kg above target weight, increase the dosage of diuretics by 100%.
  If body weight is 1-2 kg above target weight, increase the dosage of diuretics by 50%.
  If body weight is 0.5-1 kg above target weight, increase the dosage of diuretics by 25%.
  If body weight is 0-0.5 kg above target weight, hold diuretics.
Another example of oral furosemide dose titration protocol is shown in FIG. 19.

Figure 14:
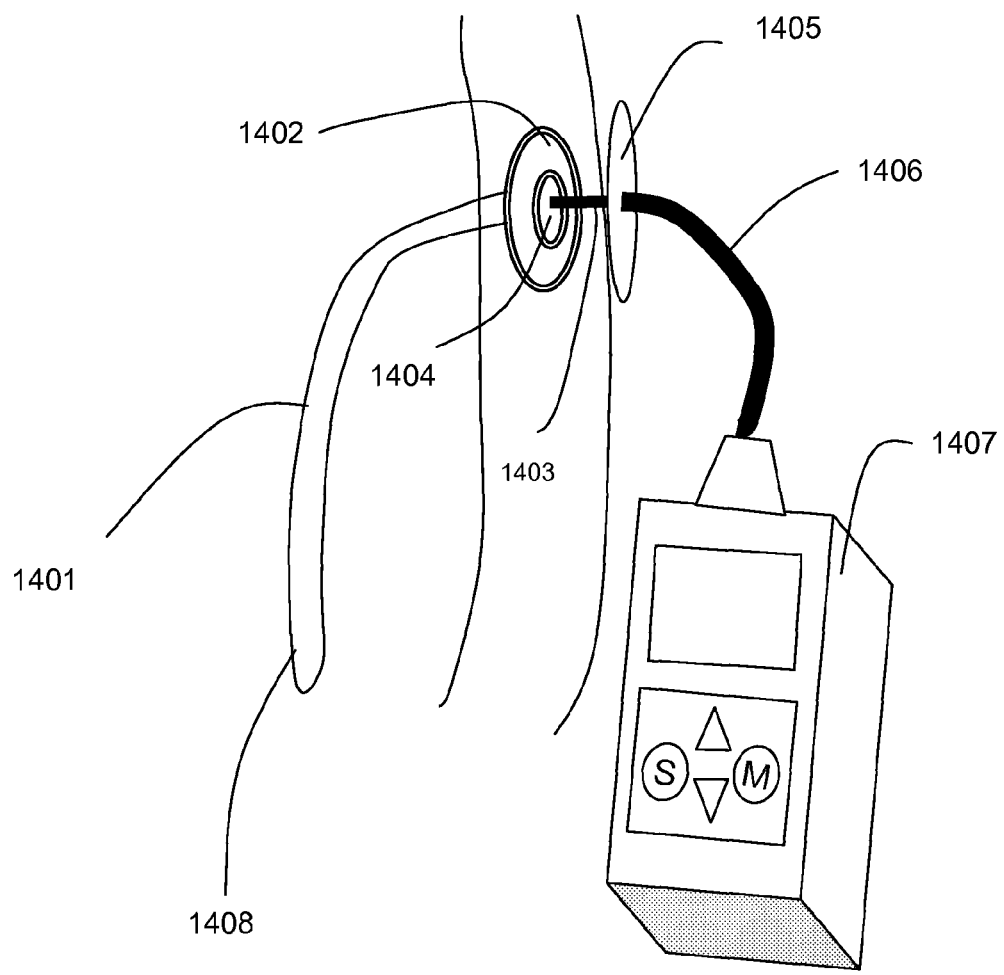
FIG. 14 illustrates infusion of diuretic into the body.

FIG. 14 illustrates infusion of diuretic into the body. In FIG. 2, diuretic medication is infused into subcutaneous tissue. In alternative embodiments shown in FIG. 14, diuretic medication may be infused into a peritoneal cavity, an intravascular space (e.g., into a vein) or intramuscularly. The diuretic infusion pump 1407 attaches to a tubing system 1406, an adhesive 1405 and a needle 1403.

A plastic tube 1401 (a catheter) is attached to a silicone bubble 1404 (septum). Tip 1408 of the plastic tube may be located into a peritoneal space or a vein (or an artery). A needle 1403 is inserted into the silicone bubble. Medication is delivered from the infusion pump 1407 through a tubing system 1408, a needle 1403 and a plastic tube 1401 into a target space of a user. Examples of a target space include a peritoneal space, a vein, an artery and a muscle. A port 1402 and silicone bubble 1404 may be located in subcutaneous tissue or may be located outside the skin.

Figure 15:
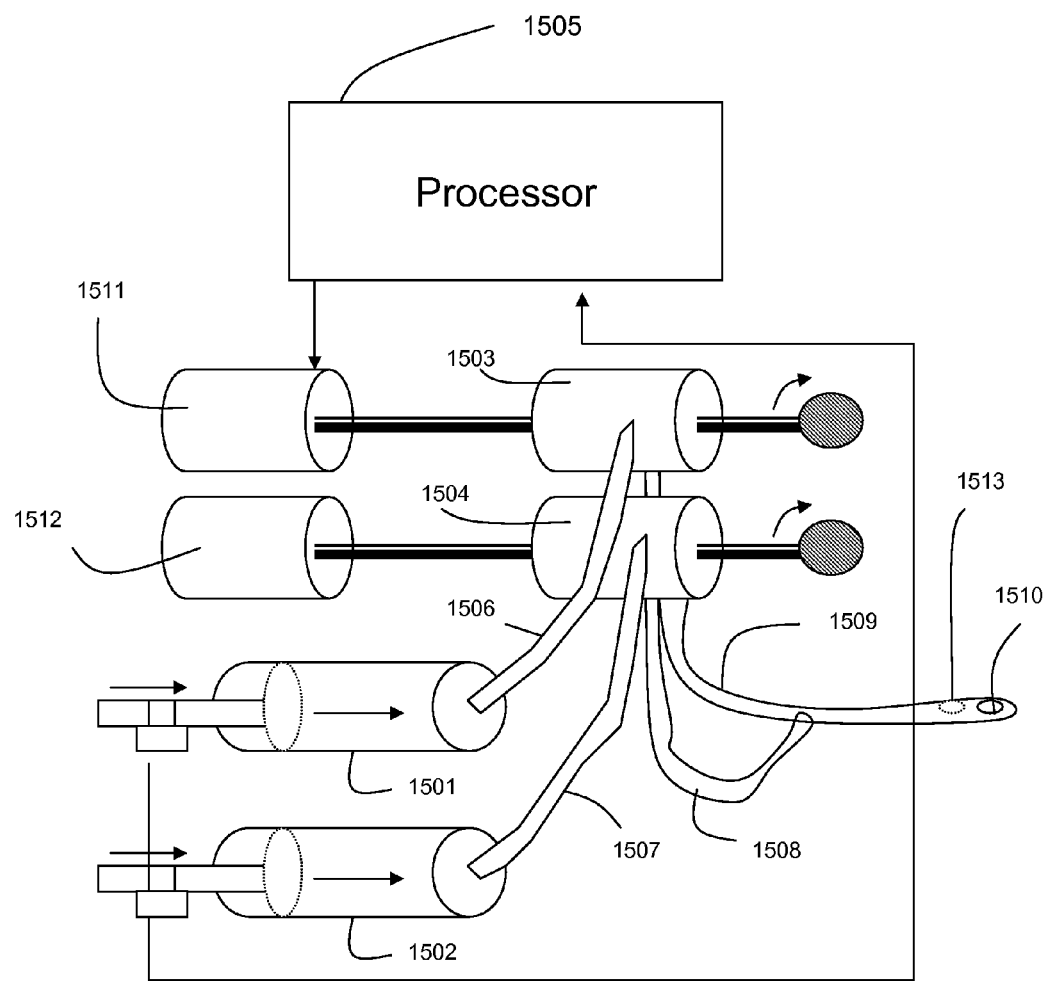
FIG. 15 is a mechanical depiction of another diuretic pump.

FIG. 15 is a mechanical depiction of yet another diuretic pump. More than two drugs may be infused in alternative embodiments. Two drugs are contained in the separate drug reservoir or cartridge. One example of two drugs that may be used includes diuretics and insulin. Another example of two drugs that may be infused includes loop diuretics and thiazide diuretics. Other examples of two drugs that may be used includes "loop diuretics and vasopressin receptor antagonist", "thiazide diuretics and vasopressin receptor antagonist", "loop diuretics and potassium sparing diuretics", "thiazide diuretics and potassium sparing diuretics" and "loop diuretics and carbonic anhydrase inhibitor." Using the combination of diuretics with a different site of action may be more effective than using only one type of diuretic. Loop diuretics act on the ascending loop of Henle in the kidney. Thiazide diuretics act on distal convoluted tubule in the kidney. Examples of vasopressin receptor antagonists include conivaptan and tolvaptan.

FIG. 11 shows an infusion pump with two drug reservoirs 1101, 1102 that share one pump 1106. FIG. 15 shows two peristaltic pumps 1503, 1504 connecting with two different reservoirs 1501, 1502. A processor 1505 is electrically connected with electric motors 1511, 1512. The processor 1505 controls these electric motors 1511, 1512 and pumps 1503, 1604 to deliver medication from each medication reservoir 1501, 1502. The pump 1503 is connected with a reservoir 1501 and delivers a medication from a reservoir 1501 through a tubing system 1506, 1508 to a user. The pump 1504 is connected with the reservoir 1502 and delivers medication from the reservoir 1502 through a tubing system 1507, 1509 to a user.

In this example, the tube 1508 merges with tube 1509. However, there are different channels within the tube to deliver each medication through different channels to prevent mixture of non-compatible medications. These two medications are delivered through separate openings 1510, 1513. Two medications may be delivered according to two separate programs, protocols, parameters.

In alternative embodiments, a diuretic inhaler may be used. Examples include a furosemide inhaler, a bumetanide inhaler, and so forth. If measured body weight is above a previously set target weight, the display on the weight measurement apparatus, the diuretic inhaler or a separate device may show instructions on the dose of drug to be inhaled. For example, if measured body weight is one kilogram above the target weight, a user may be instructed to have one extra-inhalation of furosemide. Other diuretic inhalers, including (but not limited to) furosemide, bumetanide, and torsemide, may be used in alternative embodiments.

Figure 16:
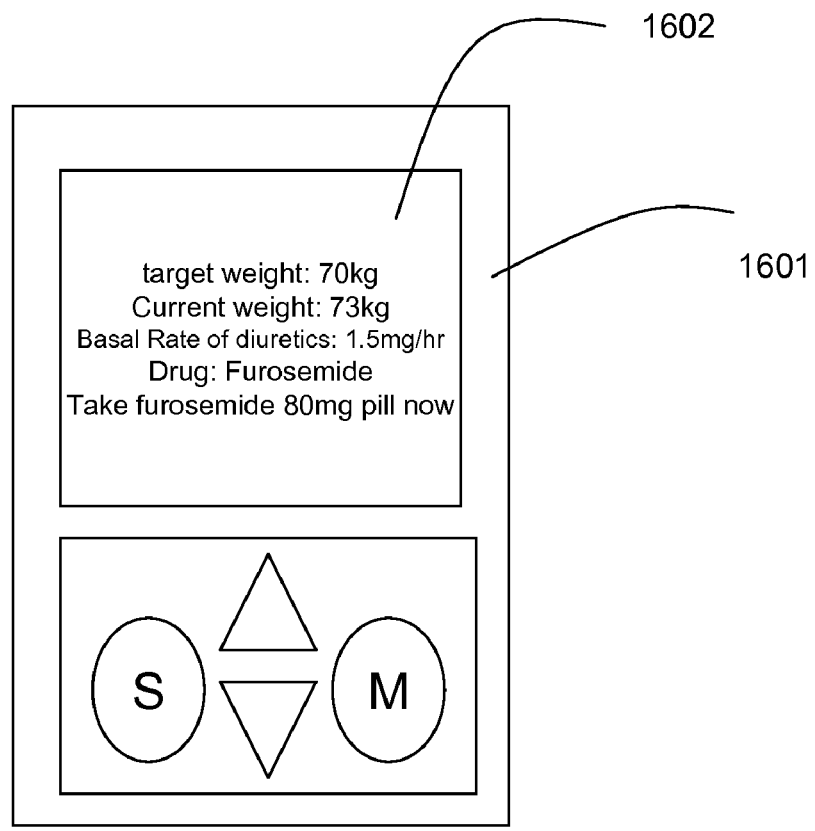
FIGS. 16-18 further illustrate operation of further embodiments for diuretic dispensing.
Figure 17:
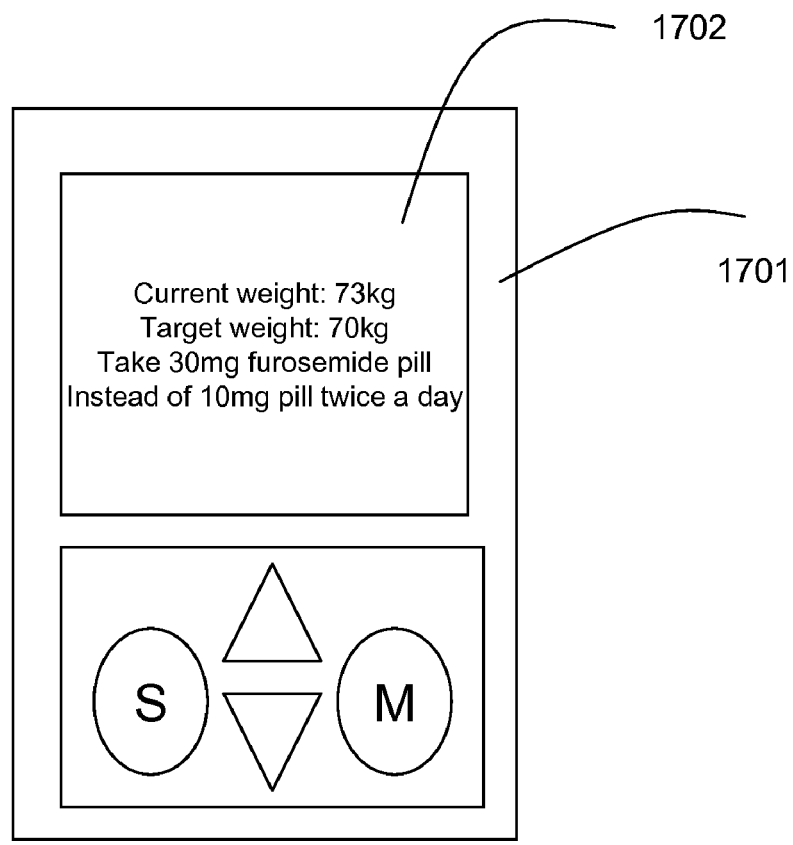
Figure 18:
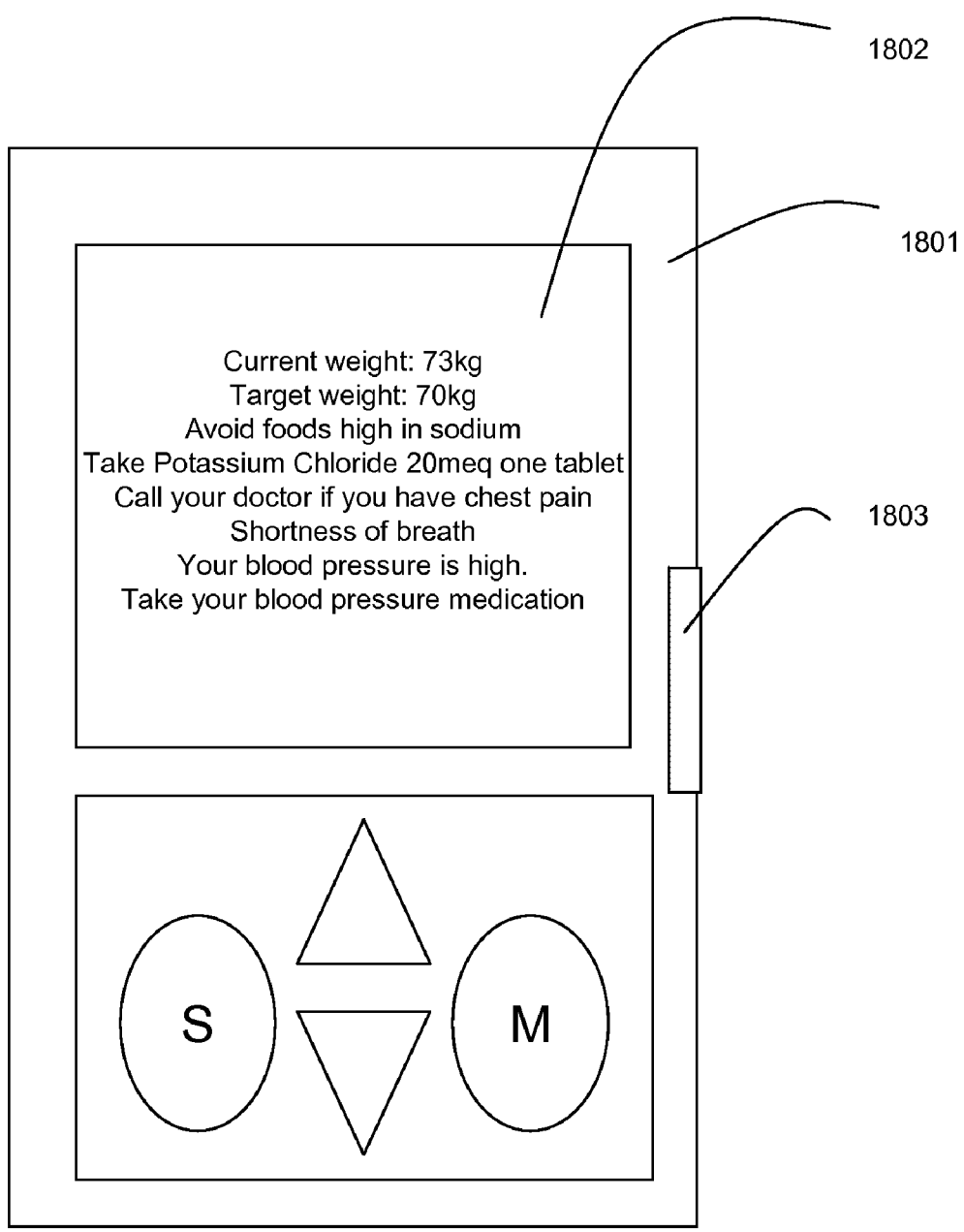

FIGS. 16-18 further illustrate operation of other embodiments. In FIG. 16, oral diuretic medication is used in combination with a diuretic infusion pump. Some patients may need to take doses of diuretics that are higher than what is available from a portable diuretic infusion pump. In some cases, a larger diuretic infusion pump may be used. However, some people may not like the larger size. In an alternate approach, the diuretics infusion pump may instruct the user to take oral diuretics to supplement the diuretic infusion. This can keep the size of the pump smaller. In FIG. 16, the display 1602 of a diuretic infusion pump 1601 shows instruction to take furosemide 80 mg pill in addition to diuretic infusion through the diuretic infusion pump. FIG. 24 shows a protocol that uses oral furosemide pills in addition to furosemide infusion.

In FIG. 17, the device provides instructions on diuretic titration based on a patient's body weight or other conditions or variables. In this example, the device does not have infusion capacity. Examples include portable phones and PDAs (personal digital assistant). Here, the device 1701 has a display 1702 which shows instructions to increase the dose of furosemide according to the weight.

In FIG. 18, the diuretic infusion device has various other functions that may improve the health of patients. For example, if body weight increases due to increased body fluid, it helps to remind patients to control the amount of salt (sodium) that they take daily. The display 1802 shows instructions to avoid food high in sodium. This device may also provide a list of foods high in sodium content, low in sodium content, high in potassium, magnesium, calcium, and/or low in potassium, magnesium, calcium. Diet information may be provided for educational purposes. In alternative embodiments, the device may have a scanner to scan food to notify users whether scanned foods are appropriate for users to take or not. The data (e.g. images) obtained from food scanning may be compared with data saved in the database within the diuretic infusion device to retrieve information on the scanned food. If the scanned food is high in sodium content, instruction to avoid this food may be shown on the display of the diuretic infusion pump. The food scanning can be performed by a separate device such as PDA, a handheld computer, a remote control device, a portable phone, an iPHONE™, an iPOD™, and so forth.

The diuretic infusion device may also be connected with a blood pressure cuff, either wirelessly or in a wired manner. Blood pressure information measured by the blood pressure cuff is transmitted to the diuretic infusion pump. Certain instructions may be provided on the display 1802. See FIG. 36. A database of references on health topics, drug information, emergency instruction, BLS (basic life support) may be saved in the memory within diuretic infusion device or diuretic dose instruction device and can be viewed on the display of the device. Examples of instructions include reminding a user to take antihypertensive medications as scheduled, instructing a user to adjust the dose of antihypertensive medications if blood pressure is low or high. If a user develops chest pain, shortness of breath or other urgent medical conditions, the user may be instructed to call his doctor or go to the nearby emergency room or call 911. A user may press an emergency button 1803 to notify family, help agent, 911 or hospital for help during emergent situations. These various functions may be programmed by a healthcare provider.

Instructions to take potassium supplement, magnesium supplement and other electrolyte supplement may be displayed on the screen. These electrolytes may be lost by the kidneys as diuretics dose increases. In FIG. 18, a user is instructed to take potassium chloride (KCL) 20 meq. See also FIG. 54.

FIGS. 19-35 show additional protocols for diuretic dispensing. FIG. 19 illustrates an example of oral furosemide dose titration protocol that may be programmed for the diuretic infusion pump, weight measurement apparatus or other devices.

FIG. 20 illustrates an example of a furosemide infusion algorithm that may be programmed in the diuretic infusion pump or a remote control device. Bolus infusion is added to the basal rate infusion when the measured weight exceeds the target or dry weight by a certain value.

Figure 21:
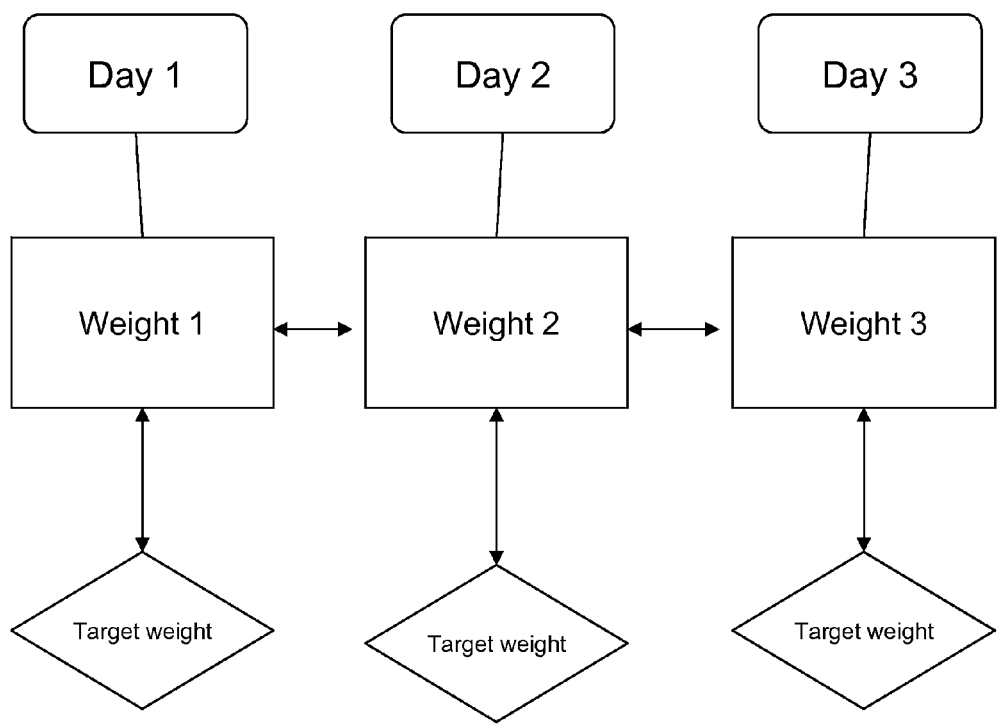

In FIG. 21, body weight is measured on different days. Body weight 1 on day 1 is compared with a previously set target weight (or dry weight). Body weight 2 on day 2 is compared with a set target weight and weight 1 to determine if weight is decreasing or increasing. Body weight 3 on day 3 is compared with a set target weight and weight 2, weight 1 to determine if weight is decreasing or increasing. Assume that weight 1 is greater than the target or dry weight. If weight 2 is greater than the target weight, but less than weight 1, this may indicate that the diuretic infusion based on weight 1 and the target weight is lowering the body weight. If weight 2 is greater than both the target weight and weight 1, this may indicate that the diuretic infusion based on weight 1 may not be working appropriately and require an increase of diuretic infusion.

Figure 22:
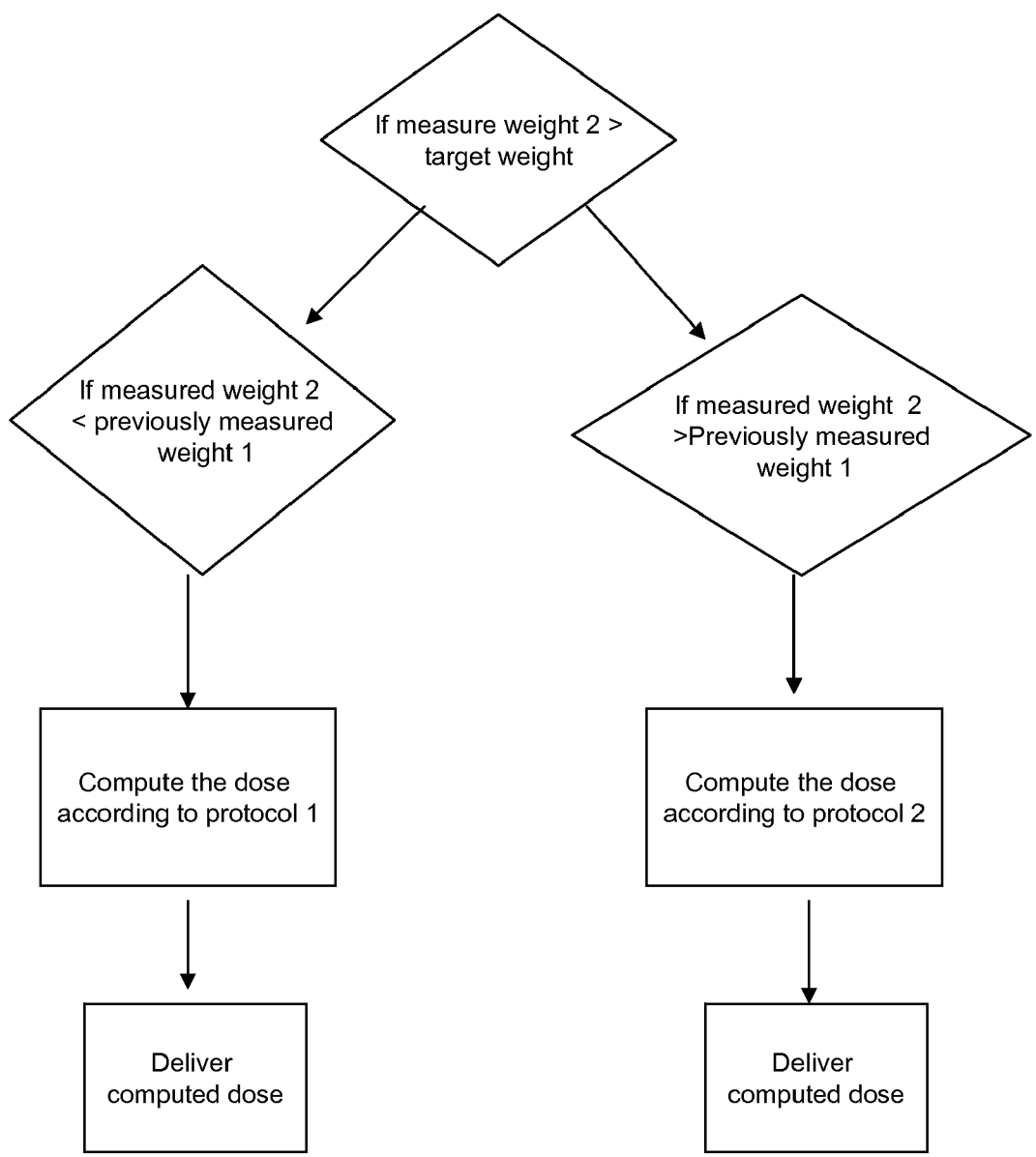

FIG. 22 illustrates an algorithm that may be programmed in the diuretic infusion pump. Even if measured body weight is greater than the previously set target weight or dry weight, different dose of diuretic infusion may be required depending on whether weight is increasing or decreasing. If weight 2 is greater than the target weight, but less than weight 1, dose computation is performed according to protocol 1 of FIG. 23. However, if weight 2 is greater than target weight and weight 1, diuretic dose computation is performed according to protocol 2 of FIG. 23.

FIG. 24 illustrates another example of diuretic protocol. If weight 3 measured on day 3 is still greater than weight 2 on day 2 despite increase of furosemide bolus and basal rate infusion, a higher dose of furosemide may be needed. To avoid rapid consumption of furosemide in the reservoir or cartridge, a user may be asked to take a furosemide pill in addition to furosemide infusion. A user has an option to choose this furosemide protocol 3 or not. If a user does not want to use this protocol 3, he can choose not to use this protocol using the menu and keypad on the diuretic pump. If this protocol 3 is not chosen, furosemide infusion may be adjusted according to a protocol 1, protocol 2 or protocol 4 to increase the infusion rate. Protocol 4 is shown in FIG. 25.

FIG. 26 illustrates another example of a furosemide infusion protocol. This protocol 5 does not use basal rate infusion of furosemide. This protocol 5 provides only bolus infusion of furosemide. This protocol may be useful for people who want to remove the diuretic infusion pump after bolus infusion.

Figure 27:
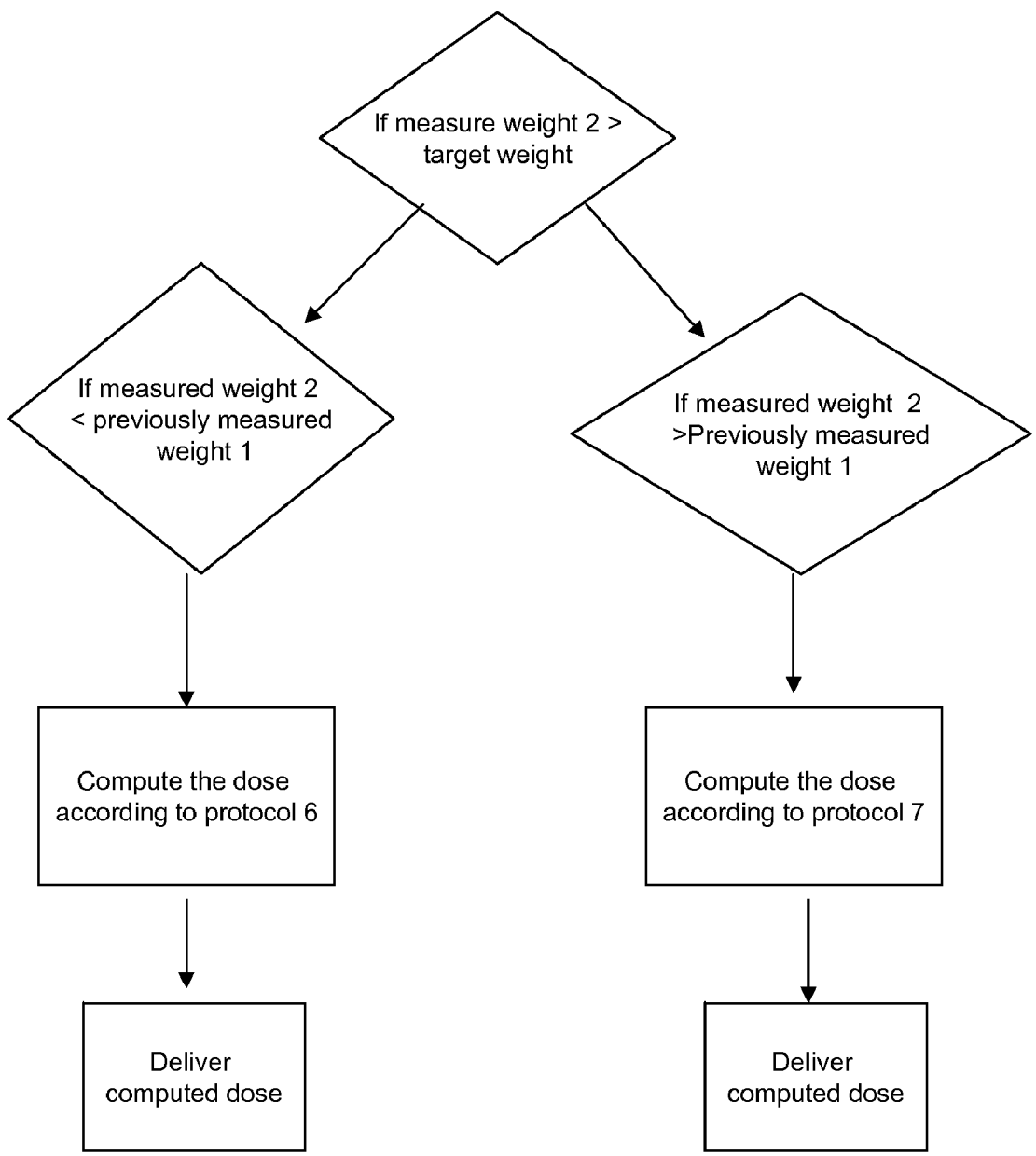

FIG. 27 illustrates an example of a block diagram of an algorithm that may be programmed in the diuretic infusion pump. FIG. 27 is different from FIG. 22 in that it utilizes different protocols. Protocols 6 and 7 are shown in FIGS. 28 and 29.

Figure 30:
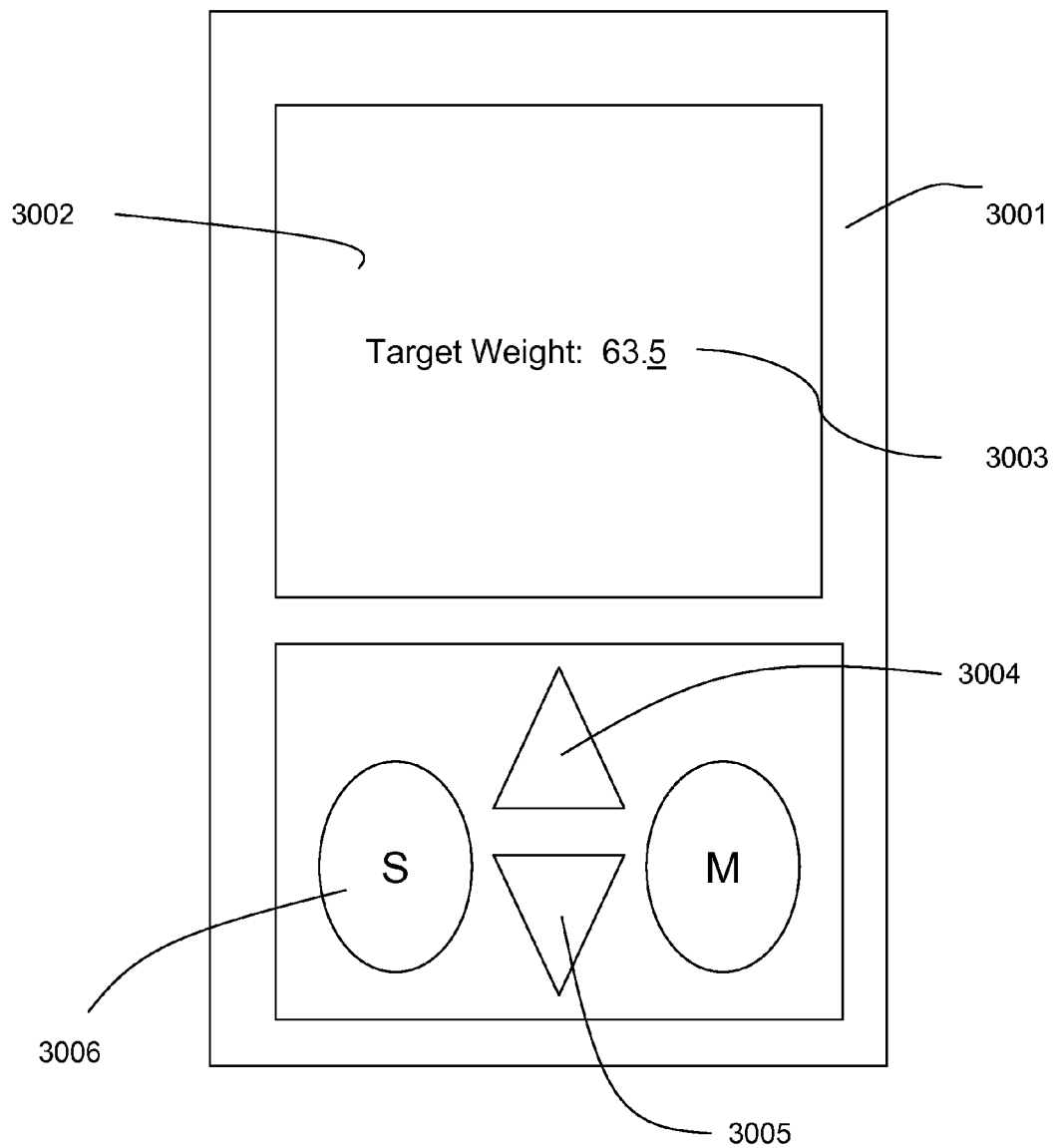
FIGS. 30 and 31 illustrate further embodiments for a diuretic infusion system.

FIG. 30 illustrates another example. Diuretic infusion pump 3001 has a screen 3002. A user uses a keypad to edit weight information. The target weight is displayed on the screen. A cursor is located on the number to the right of the decimal point. In this FIG. 31, it is located on the digit 5 3003. A user can choose different number using scrolls 3004, 3005. S button 3006 is pressed to select a number. The current weight can be manually put into the diuretic infusion pump in a similar manner.

Figure 31:
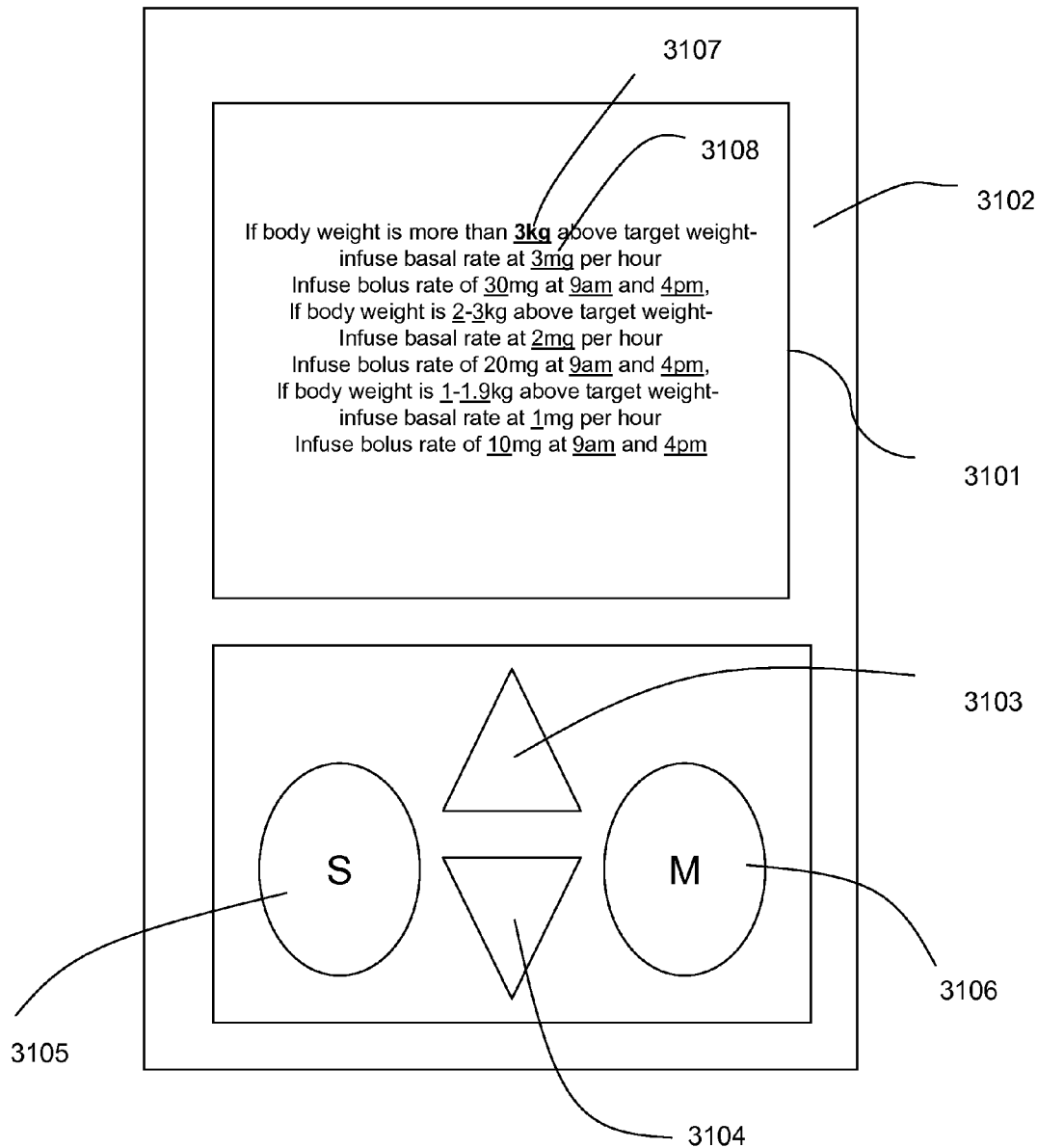

In FIG. 31, a furosemide infusion protocol is shown on the screen 3101 of the diuretic infusion pump 3102. The underlined numbers can be changed using scroll buttons 3103, 3104. If scroll button 3103 is pressed, the number increases. If scroll button 3104 is pressed, the number decreases. The cursor is located on underlined thick number 3107, which is a 3. If scroll button 3103 is pressed once, the 3 changes to 4. If scroll button 3104 is pressed once, the 3 changes to 2. If button S 3105 is pressed, the number is selected. If button S is pressed when number 3107 is 3, the 3 is selected and cursor moves on to next underlined number 3108. If all numbers are selected, button M is pressed to move on to another menu.

Figure 32:
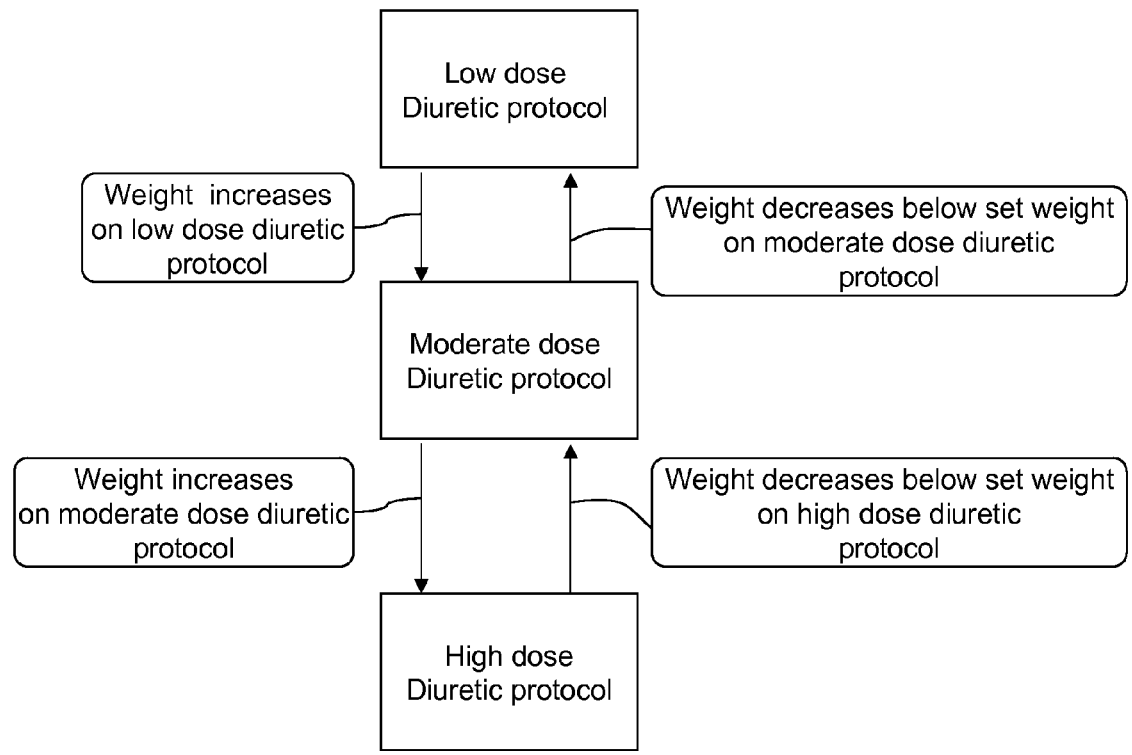

FIG. 32 shows another algorithm that may be programmed in the diuretic infusion pump. In this embodiment, there are three different diuretic dose protocols: a low dose diuretic protocol (FIG. 33), a moderate dose diuretic protocol (FIG. 34) and a high dose diuretic protocol (FIG. 35). The low dose protocol may be used when a low dose diuretic is adequate to maintain the target body weight. If the body weight continues to increase on the low dose diuretic protocol, the diuretic infusion pump is programmed to automatically change the protocol to the moderate dose diuretic protocol. If the body weight continues to increase on the moderate dose diuretic protocol, the diuretic infusion pump is programmed to automatically change the protocol to the high dose diuretic protocol.

In the reverse direction, if the body weight decreases below a target weight on high dose diuretic protocol, the diuretic infusion pump is programmed to automatically change the protocol to the moderate dose diuretic protocol. If the body weight decreases below a target weight on the moderate dose diuretic protocol, the diuretic infusion pump is programmed to automatically change the protocol to the low dose diuretic protocol.

Another protocol is to automatically change the diuretic dose protocol to a higher dose protocol if the body weight remains above a target weight for more than a set period of time. For example, if the body weight remains above a target weight for more than three days in a row on the low dose diuretic protocol, the diuretic pump changes the protocol to the moderate dose diuretic protocol to decrease body weight. Yet another protocol is to automatically change the diuretic dose protocol to a lower dose protocol if the body weight remains below a target weight for more than a set period of time. In another example, if the body weight remains below a target weight for more than two days in a row on the high dose diuretic protocol, the diuretic pump is programmed to automatically change the protocol to the moderate dose diuretic protocol. In alternative embodiments, there may be more or less than three different dose diuretic protocols and/or the triggers of when to switch protocols may also vary. In alternative embodiments, the diuretic infusion pump may change the drug infusion protocol only after a user and/or a healthcare provider, such as a physician or a nurse, approves the change of the drug infusion protocol.

A healthcare provider may review the data transmitted by the diuretic infusion pump system over the internet, wireless communication, a phone, and/or fax. Data including (not limited to) current weight, previous weight, blood pressure, the dosage of a drug, the name of the drug in use, condition of the user, the presence of other symptoms such as chest pain may be delivered to a healthcare provider. A healthcare provider may be able to program the diuretic infusion pump remotely via an internet in alternative embodiment.

Figure 36:
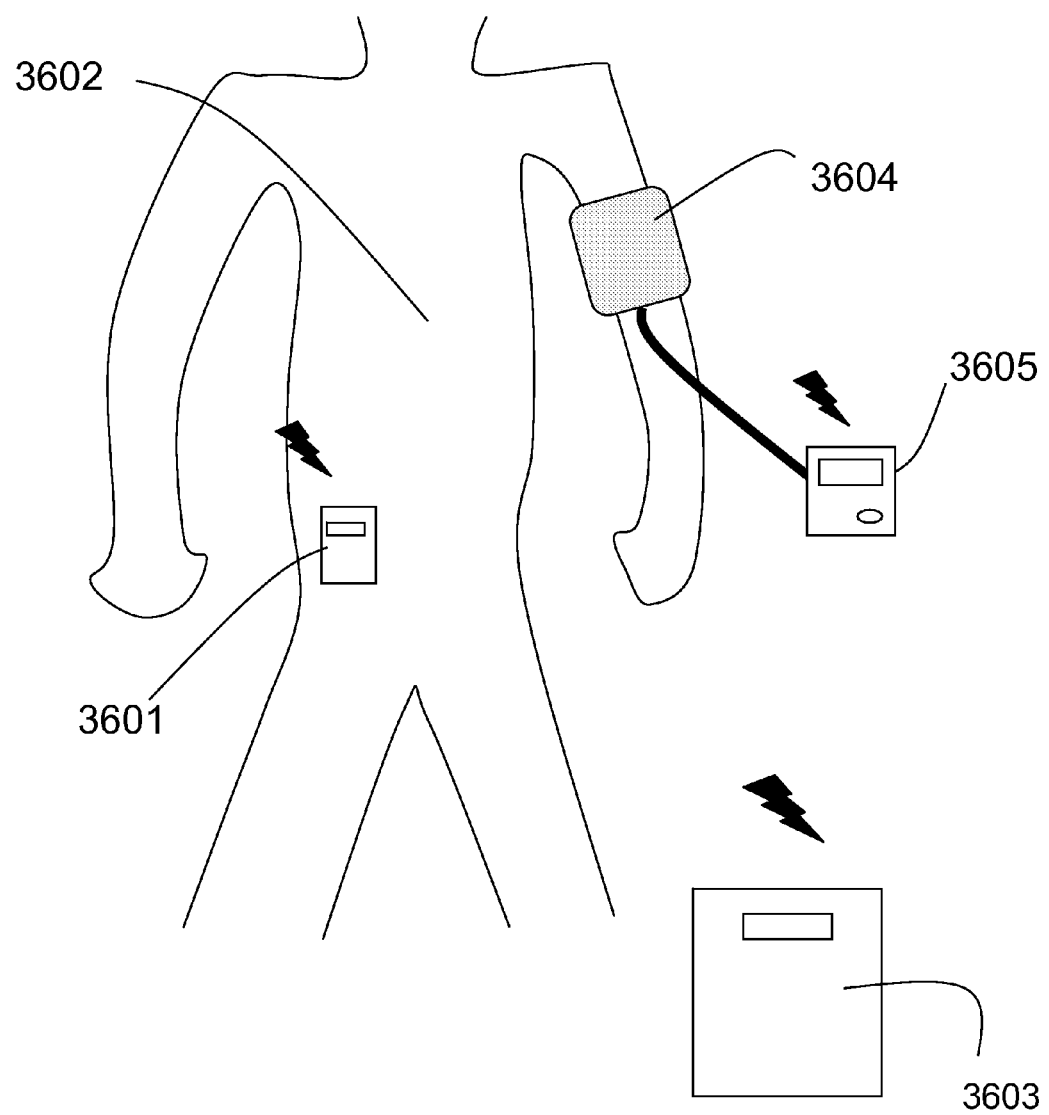
FIG. 36 illustrates another diuretic infusion system including an electric scale.

FIG. 36 depicts another embodiment of the present invention that uses both weight and blood pressure measurements. A blood pressure cuff 3604 is attached to an arm of a human body 3602. The blood pressure cuff 3604 can be connected to a blood pressure measuring device 3605. The blood pressure measuring device 3605 can be coupled to a processor, wireless communication module, a controller and a software program, though it may not be coupled to all of these in some embodiments. The diuretic infusion pump 3601 can communicate wirelessly or via other means with the blood pressure measuring device 3605. In alternative embodiments, the blood pressure measuring device 3605 can communicate wirelessly or via other means with an electric scale 3603. In alternative embodiments, a user manually inputs measured blood pressure into a diuretic infusion device or a remote control device.

FIG. 37 illustrates another example of a furosemide infusion protocol. As shown in FIG. 36, the diuretic infusion pump receives the measured blood pressure wirelessly from the blood pressure measurement device. If the measured blood pressure is below a set blood pressure, the diuretic infusion pump can be programmed to stop furosemide infusion automatically to prevent hypotension, dehydration.

FIG. 38 illustrates an example of a furosemide and enalaprilat infusion protocol. As shown in other figures, the diuretic infusion pump can contain more than one drug reservoir. In this example, the diuretic infusion pump has one reservoir containing furosemide and another reservoir containing enalaprilat. Enalaprilat is an angiotensin converting enzyme (ACE) inhibitor which is an antihypertensive drug. The protocol in FIG. 38 shows the diuretic infusion pump infusing enalaprilat as well as furosemide according to measured blood pressure to maintain target blood pressure.

FIG. 39 illustrates another example of a furosemide and enalaprilat infusion protocol. The diuretic infusion pump adjusts the infusion rate and a dose of enalaprilat and furosemide according to the measured blood pressure to maintain target blood pressure.

FIG. 40 illustrates an example of furosemide and metoprolol infusion protocol. Metoprolol is a beta blocker which lowers blood pressure and heart rate. The diuretic infusion pump may contain one reservoir containing furosemide and one reservoir containing metoprolol. The diuretic infusion pump adjusts the infusion rate and dose of metoprolol and furosemide according to the measured blood pressure to maintain target blood pressure. The diuretic infusion pump may adjust the infusion rate and dose of metoprolol to maintain target heart rate. A patient with heart disease may develop arrhythmia, such as supraventricular tachycardia (rapid heart rate), atrial fibrillation, or ventricular tachycardia. The diuretic infusion pump can infuse metoprolol to lower heart rate. In alternative embodiments, the diuretic infusion pump can communicate wirelessly with an implantable cardioverter defibrillator (ICD), a pacemaker. If an ICD or a pacemaker detects arrhythmia, the ICD or pacemaker can send this arrhythmia information wirelessly or via other means to the diuretic infusion pump. The diuretic infusion pump may infuse an anti-arrhythmic drug to treat the arrhythmia. Examples of anti-arrhythmic drugs include, but are not limited to, amiodarone, metoprolol, sotalol, esmolol, lidocaine, disopyramide, propafenone, dofetilide, flecainide, procainamide and atropine. The diuretic infusion pump may contain and infuse only anti-arrhythmic drug communicating with an ICD or a pacemaker in alternative embodiments.

In another embodiment, a user can use one reservoir that contains diuretics and a second reservoir that contains an inotropic drug that increases blood pressure. Examples of inotropic drugs include (but are not limited to) dopamine, dobutamine, phosphodiesterase inhibitor, amrinone, milrinone, enoximone, pimobendan, levosimendan, calcium sensitizing agent, venarinone, and ibopamine. In alternative embodiments, the diuretic infusion pump contains a combination of antihypertensive drugs, inotropic agents, diuretics, and it adjusts the infusion rate according to blood pressure measured by non-invasive blood pressure measurement device and/or measured body weight.

Figure 41:
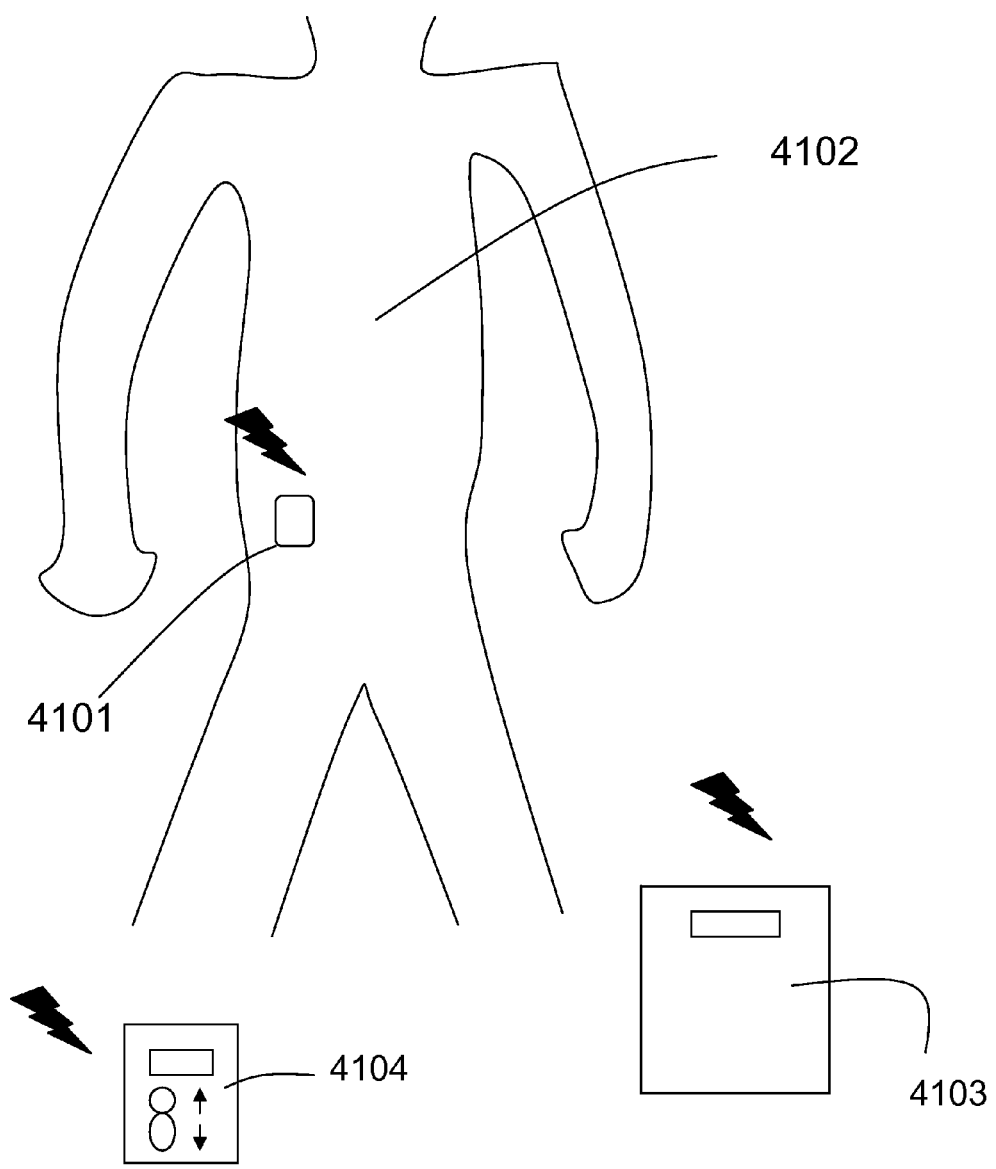
FIG. 41 illustrates another diuretic infusion system including a remote control device.

FIG. 41 illustrates another embodiment. A diuretic infusion device 4101 is attached to a human body 4102. This portable diuretic infusion device 4101 delivers diuretics from a reservoir to the human body 4102. The diuretic infusion device 4101 may be smaller in size compared to other embodiments shown in other figures. This diuretic infusion device 4101 can be disposable. The diuretic infusion device 4101 contains a reservoir, a programmable processor, an exit port, a cannula and a motor, though some embodiments may contain fewer components or additional components. The diuretic infusion device 4101 can communicate wirelessly or via other means with a remote control device 4104. The remote control device 4104 can communicate wirelessly with a weight measurement device 4103 and a diuretic infusion device 4101 in one embodiment. The remote control device 4104 may communicate wirelessly with only the diuretic infusion device 4101, and not with the weight measurement device 4103 in alternative embodiments.

Figure 42:
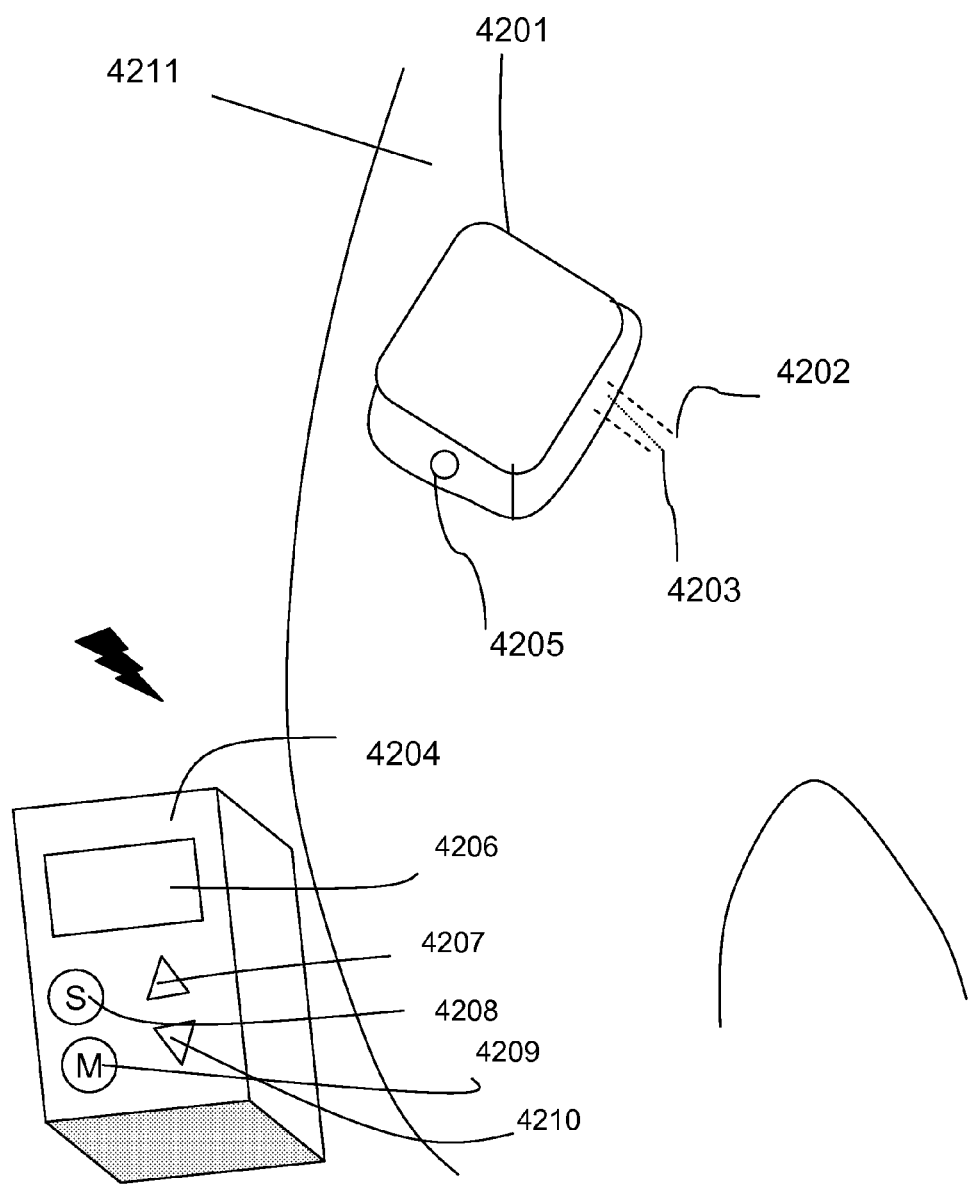
FIG. 42 illustrates a more detailed view of the diuretic infusion device and the remote control device.

FIG. 42 further illustrates the diuretic infusion device 4201. The diuretic infusion device 4201 has a needle 4203 and cannula 4202. The diuretic infusion device 4201 is connected to a human body 4211 subcutaneously via a cannula 4202. The diuretic infusion device 4201 is disposable in some embodiments, but the reservoir of the diuretic infusion device can alternatively be refilled via a hole 4205. The remote control device 4204 programs and controls the diuretic infusion device 4201. The remote control device 4204 contains a programmable processor, a controller, a wireless transmitter/receiver, a keypad with order entry buttons 4207, 4208, 4209, 4210 and a display screen 4206, though some embodiments may contain fewer components or additional components. Measured body weight can be transmitted wirelessly from a weight measurement device 4203 to the remote control device 4204, 4204 in this embodiment. In alternative embodiments, a user manually inputs measured body weight into the remote control device 4204. A controller of the remote control device 4204 may be coupled to a processor and a wireless receiver/transmitter. When weight information enters the processor of the remote control device 4204, the processor can compute the dosage of diuretic based on body weight. The remote control device 4204 wirelessly transmits commands to the diuretic infusion device 4201. The remote control device 4204 can control the infusion rate of the diuretic infusion device 4201 wirelessly or by other means (e.g., wired). A user can choose and program particular diuretic infusion protocol(s) using button(s) 4207, 4208, 4209, 4210 on the keypad of the remote control device 4204. Various drug infusion protocols and methods shown in other figures (see FIGS. 4, 19-35, 37, 38, 45 and other figures) may be embedded in the processor of the remote control device 4204.

Figure 54:
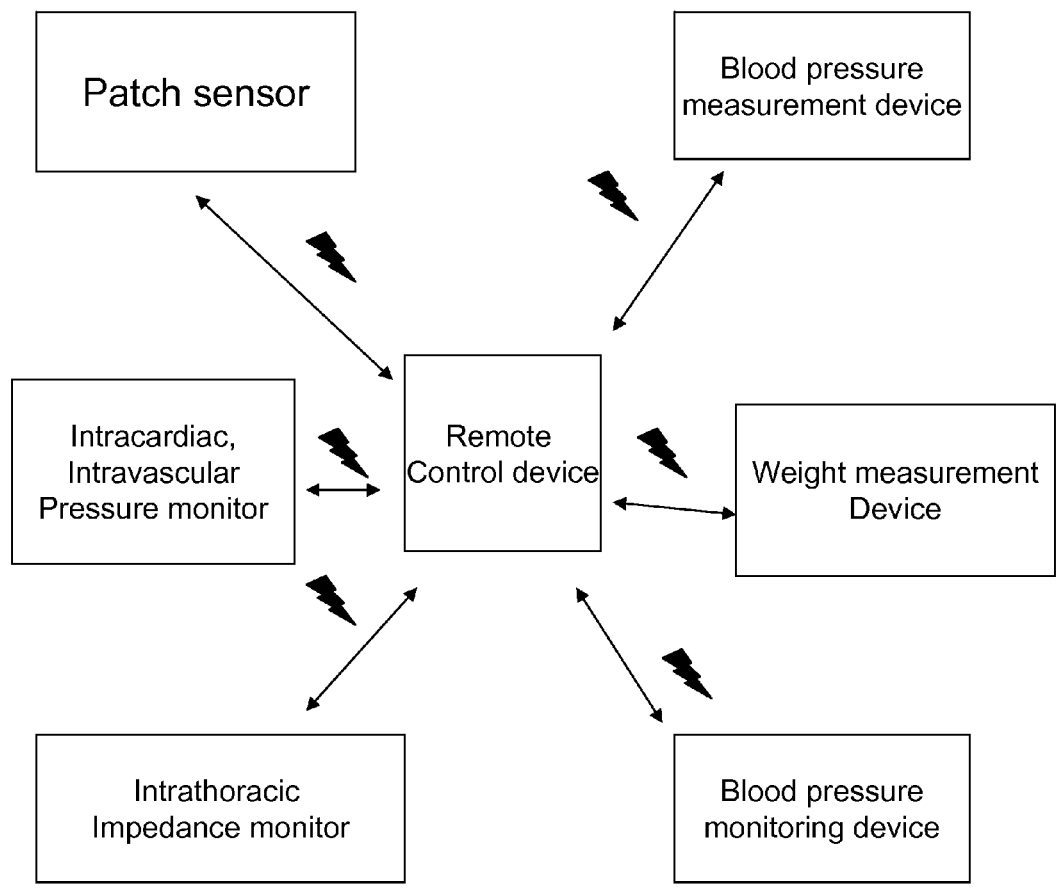
FIGS. 54 and 55 show various biological parameters and factors that may be used with various embodiments, such as that of FIG. 42.
Figure 55:
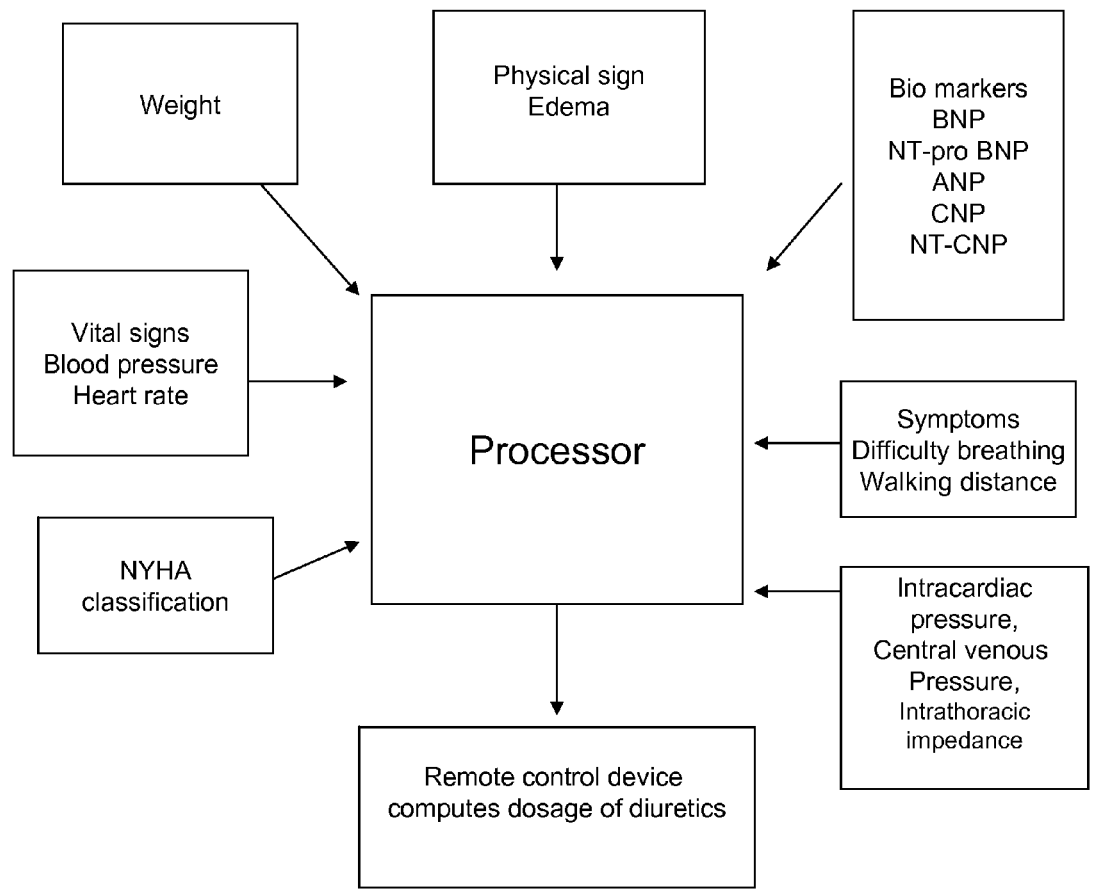

The processor within the remote control device 4204 may be able to compute the dosage of a diuretic based on the amount of salt, sodium and/or water of food. A user may infuse a diuretic before or when the user eats food that contains salt and/or water to excrete extra salt and water to maintain optimal body fluid condition. In other embodiments, the processor within the remote control device 4204 computes the dosage of diuretic based on various biological parameters using protocols shown in other figures. For example, FIGS. 54 and 55 show various biological parameters and factors that may be used in these embodiments in combination with weight. The biological parameter measurement sensors can be coupled with an implantable device(s) like a pacemaker, an implantable cardioverter defibrillator, a cardiac resynchronization therapy, etc. The remote control device 4204 can communicate wirelessly with the biological parameter measurement sensor(s). An intracardiac/intravascular pressure monitoring sensor, an intrathoracic impedance monitor sensor, or a patch sensor can communicate wirelessly with the remote control device 4204 in alternative embodiments.

Figure 43:
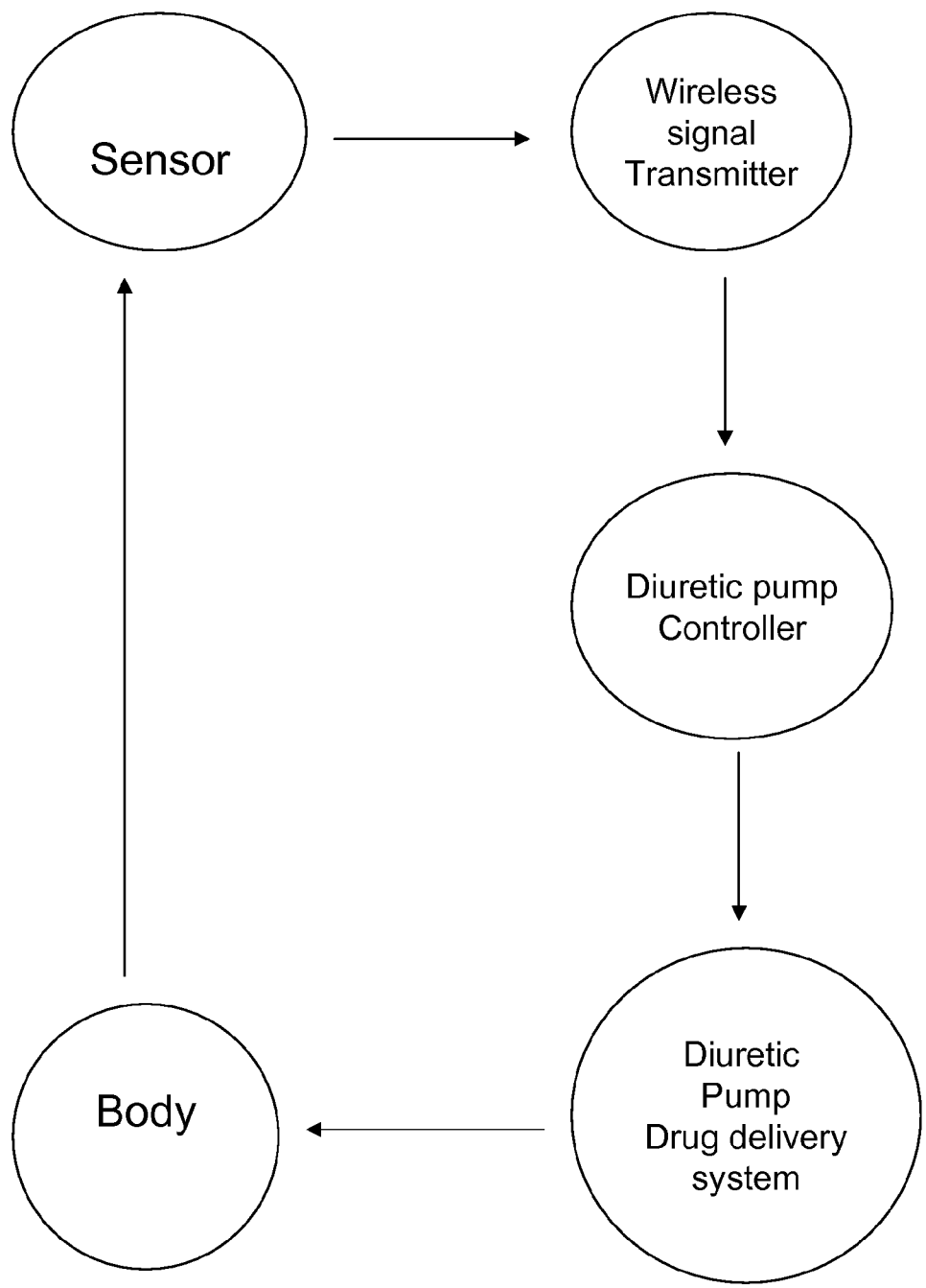
FIG. 43 illustrates the operation of a closed loop drug infusion system for a diuretic infusion pump system.

FIG. 43 illustrates another embodiment of the present invention. In this embodiment, the diuretic infusion pump system can be a closed loop drug infusion system. The closed loop drug infusion system includes a biological parameter measurement sensor and/or a biological parameter measurement device, a controller, drug infusion pump, a drug delivery system, wireless communication module, though not all of these may be included in alternative embodiments or additional modules or devices may be included. In the closed loop drug infusion system, measured biological parameter signal enters the controller of the diuretic infusion system wirelessly or via other means. The controller of the diuretic infusion pump automatically adjusts and controls the drug infusion according to the algorithms programmed in the diuretic infusion pump in the closed loop drug infusion system. The controller of the diuretic infusion pump adjusts the drug infusion to achieve or maintain a target biological parameter which is programmed into the diuretic infusion pump.

Figure 44:
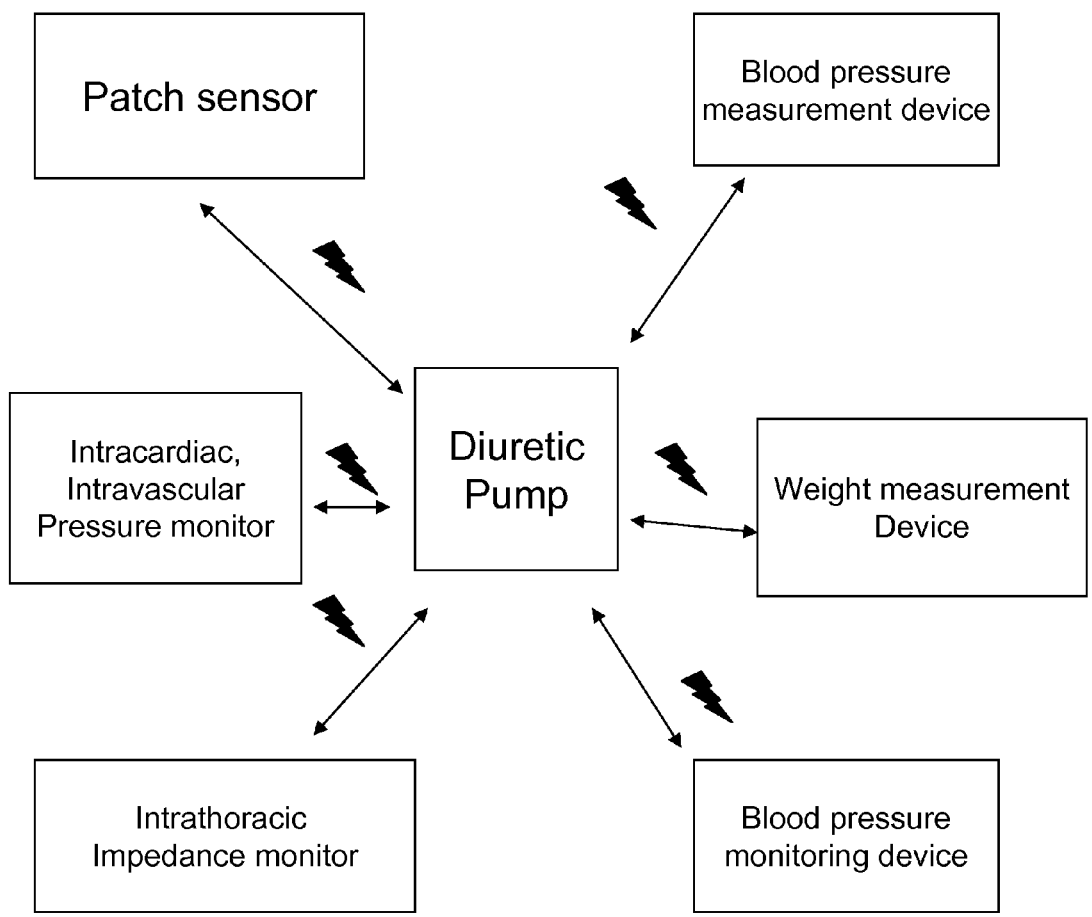
FIG. 44 illustrates wireless communication of a diuretic infusion pump system with biological parameter measurement apparatuses.

Many different biological parameter measurement sensors and/or biological parameter measurement devices can be used for the present invention. Examples of these biological parameter measurement sensors/devices include, but are not limited to, a patch sensor system, an intracardiac pressure sensor system, an intravascular pressure sensor system, an intrathoracic impedance monitor sensor system, a non-invasive blood pressure measurement sensor system, a weight measurement sensor and/or device, a blood pressure measurement cuff and device, a heart rate measurement sensor system, an electrocardiogram monitoring sensor and/or device, an arrhythmia monitoring sensor system and other vital sign measurement devices. These biological sensors can be coupled with other implantable medical devices, such as a pacemaker, an ICD, or a cardiac resynchronization therapy. The biological parameter measurement sensor/device and the diuretic infusion pump can preferably communicate wirelessly. One example is illustrated in FIG. 44. The sensor/device and the diuretic infusion pump may communicate via other means in alternative embodiments. Other means may include, but are not limited to, wired communication, manual data input and other methods described in the present invention. More than one biological parameter sensor and/or device may be used in combination with a diuretic infusion pump. For example, a weight measurement device and intravascular blood pressure measurement sensor system may be used in combination with a diuretic infusion pump. A weight measurement device and a patch sensor may be used in combination with a diuretic infusion pump. These different sensors and devices may communicate wirelessly or via other means. Different types of patch sensors may be included in the closed and/or open loop drug infusion system. The drug infusion system may adjust the infusion of drug(s) according to an average (e.g., a mean or median) value of biological parameters in alternative embodiments. For example, the drug infusion system can adjust the infusion of diuretics according to the average of the measured weight over three days. If the daily measured body weight is 70 kg, 72 kg, 71 kg over the past three days, the diuretic infusion pump can be programmed to adjust the rate of diuretic infusion according to 71 kg which is median value of three measured weights. The drug infusion system can adjust the infusion of diuretics according to the average value of measured intrathoracic electrical impedance over a period of time. In some embodiments, the diuretic infusion pump is programmed to adjust the rate of diuretic infusion according to an average value of biomarkers, blood pressure, intracardiac pressure or other biological parameters mentioned previously over a certain period of time.

In alternative embodiments, the diuretic infusion pump system is an open loop drug infusion system. The diuretic infusion pump can receive measured weight or other biological parameters from sensor(s) wirelessly or manually, however the diuretic infusion pump may or may not automatically adjust the rate of infusion in an open loop system. A user, a doctor, a nurse and/or other people that are involved in the use of the diuretic infusion pump system may need to approve or choose particular protocol(s) and methods. These people can also control the controller of the diuretic infusion pump. Healthcare provider(s) can transmit a new order or new drug infusion protocols to the diuretic infusion pump system via the Internet, a phone, or other methods. In an open loop drug infusion system, wireless communication among the devices may or may not be used.

In some embodiments, a user chooses an open loop system, a closed loop system, or mixed loop system (e.g., a closed loop system when a certain conditions are met and open loop system when a certain conditions are not met). The diuretic infusion pump system can be programmed to be a closed loop system when measured blood pressure is within a certain parameter, when a user does not have symptoms, such as chest pain, and/or when the dosage of an infused drug is within a certain range. The diuretic infusion pump can be programmed to be an open loop system when these conditions are not met in a mixed loop system.

FIG. 45 illustrates another example of a drug infusion protocol. In one example, the measured weight of a user is 74 kg and the target weight is set at 70 kg. There is 4 kg difference between the target weight and measured weight, and the measured weight is above the target weight. Following the protocol seen in FIG. 45-*a*, the basal rate of furosemide infusion increases by 0.05 mg multiplied by 40 (4 kilograms equals 40 times 100 grams), and 0.05 mg multiplied by 40 is equal to 2 mg. The basal rate of furosemide infusion increases by 2 mg per hour for 8 hours following the protocol. If the previously set basal rate of furosemide was 1 mg per hour for 8 hours daily, the new basal rate of the furosemide is 3 mg per hour for 8 hours daily. If the protocol seen in FIG. 45-*b* is to be used, the bolus rate of the furosemide increases by 1 mg multiplied by 40 (4 kilograms equals 40 times 100 grams) which is 40 mg. If the previously set bolus dose of furosemide was 20 mg twice a day, the new bolus dose of furosemide is 60 mg twice a day following the protocol of 45-*b*. A user or a healthcare provider can change the underlined numbers according to a person's sensitivity to diuretics. The change of the protocol could occur automatically or occur upon the approval of a user and/or healthcare provider(s).

Figure 46:
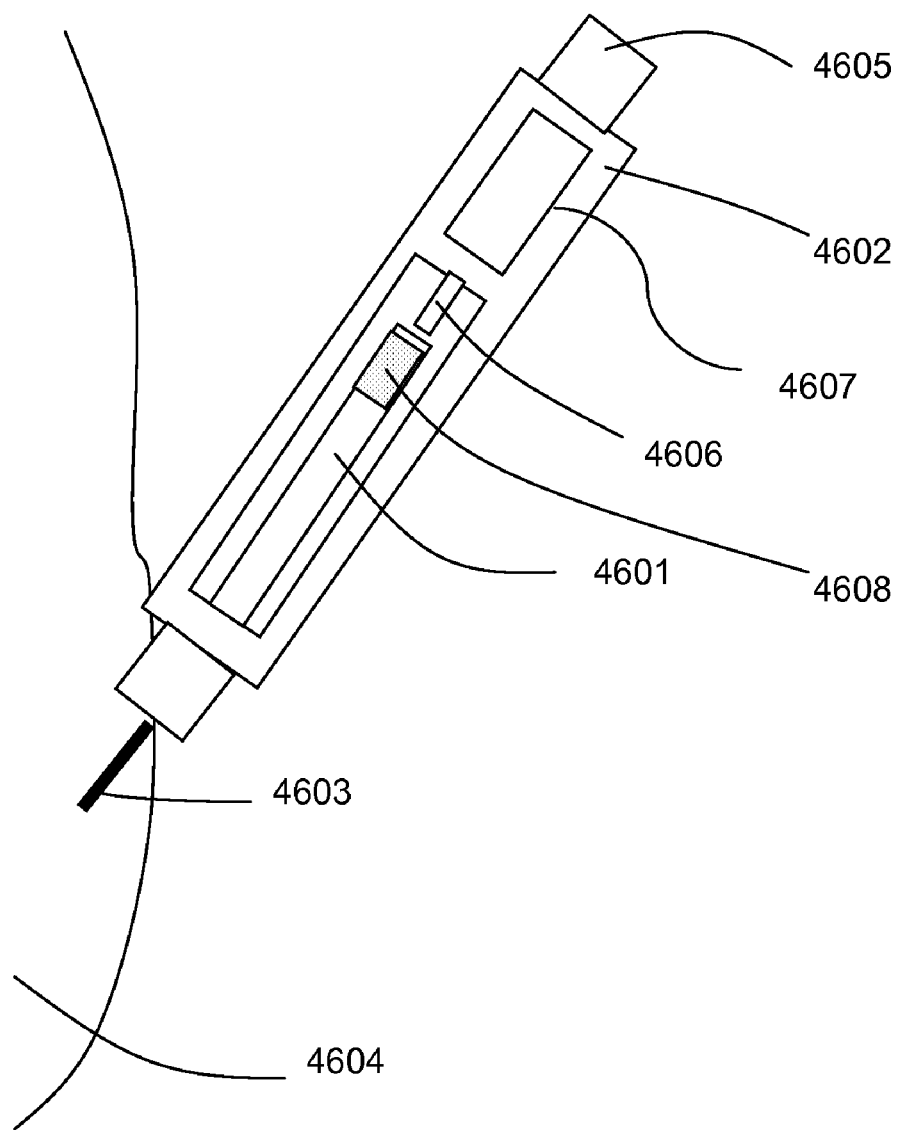
FIG. 46 illustrates a diuretic injecting pen-type device.

FIG. 46 illustrates an embodiment of a diuretic injecting apparatus. A preferred diuretic injecting apparatus is a pen-type injecting apparatus. A diuretic pen is a diuretic delivery system. The diuretic pen 4602 in FIG. 46 contains a diuretic cartridge 4601. The diuretic drug contained in the cartridge 4601 is delivered to a user 4604 subcutaneously or intramuscularly via an injection needle 4603. In one embodiment, a replaceable diuretic cartridge is used. Alternatively, a diuretic pen with a prefilled diuretic cartridge can be thrown away when the diuretic runs out. The body of a diuretic pen is generally a cylindrical tube, but can also take on other shapes. The diuretic pen can also be designed without the needle. The diuretic cartridge 4601 contains a plunger 4608 which is moved by an injection screw 4606 axially toward the injection needle 4603 by pressing a knob 4605 or a button 4605. The diuretic pen has a display 4607, which can show information such as time, dose of diuretics, battery use, date, previously used drug dosage, etc. The diuretic pen may contain a memory storage device. One example of a memory storage device is flash memory. The knob of the diuretic pen 4605 may be used to inject dose, change time or date, go to dose memory, adjust dose by pressing or turning the knob 4605, and so forth. In some embodiments, the dosage of diuretic can be determined based on the amount of salt and/or water intake. In alternative embodiments, the diuretic pen is a metered dose diuretic infusion system. When the knob 4605 is pressed, a predetermined amount of diuretic is delivered to the user. For example, if the user presses the knob 4605 once, a diuretic injection pen releases 2 mg of furosemide. The user can be instructed to press the knob 4605 once when the user eats food with low salt and/or water content, to press the knob twice for food with moderate salt and/or water content, or to press the knob three times for food with high salt and/or water content.

Figure 47:
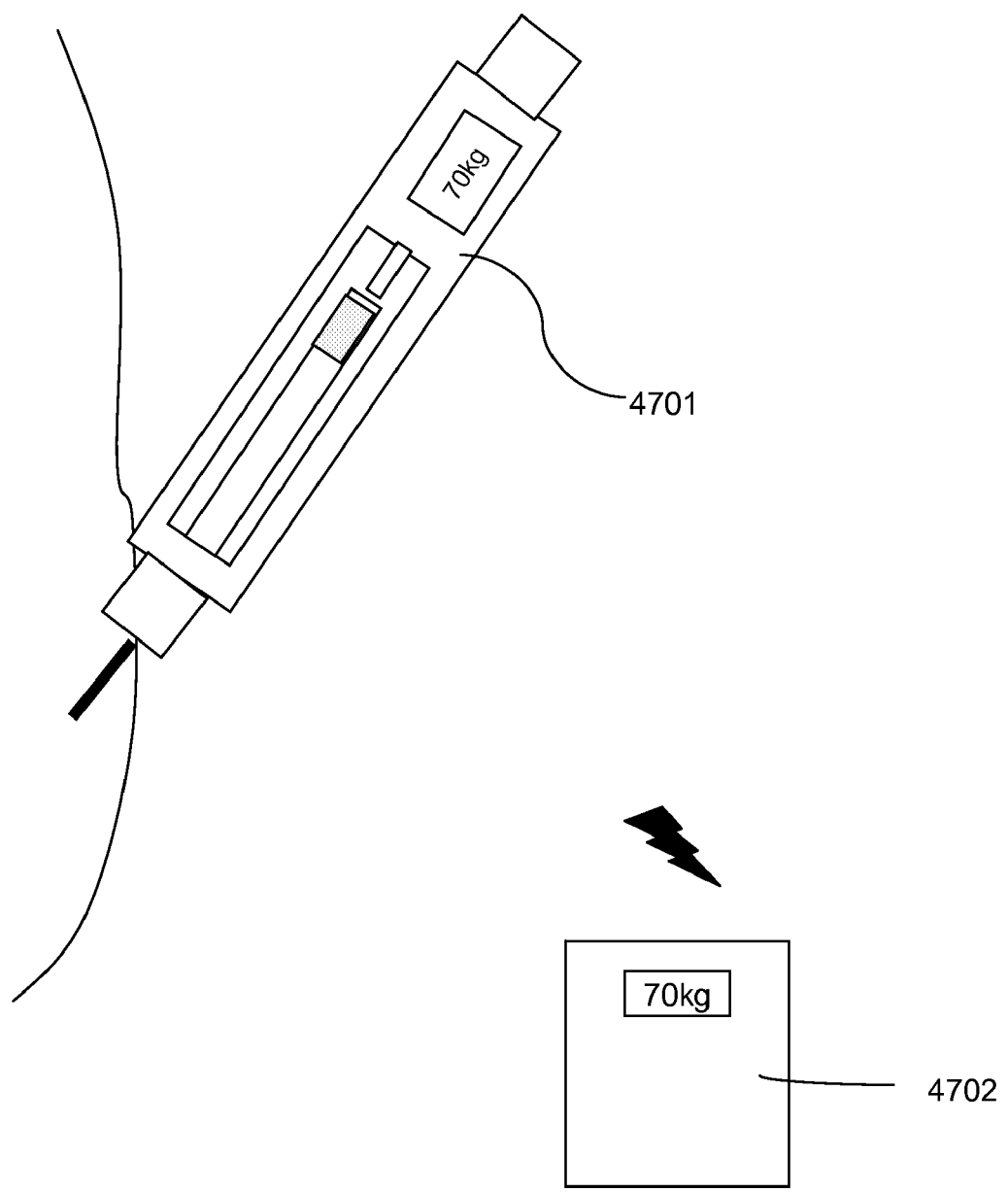
FIG. 47 illustrates a wirelessly-operated diuretic injecting pen-type device.
Figure 48:
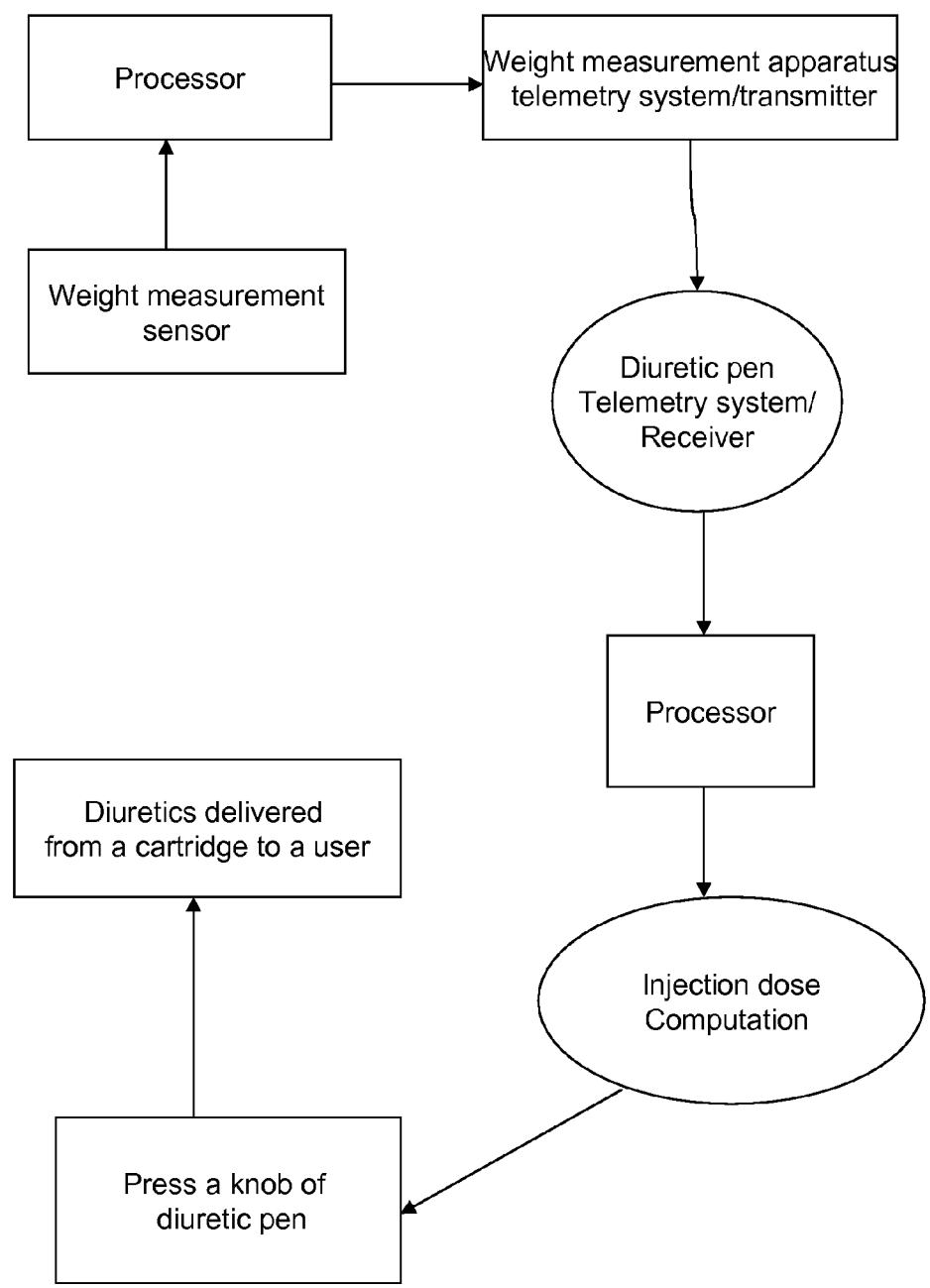
FIG. 48 illustrates the components of the diuretic injecting pen-type device.

FIG. 47 illustrates wireless communication between a diuretic pen 4701 and a weight measurement device 4702. Measured weight may be input into the diuretic pen wirelessly or manually. A user may input weight manually by using button(s), a knob, etc. As shown in FIG. 48, the diuretic pen 4701 can contain a processor, software, and telemetry system, though the diuretic pen may not have all of these components or may have additional components. The processor within the diuretic pen can compute the dose of diuretic drug based on the weight.

Figure 49:
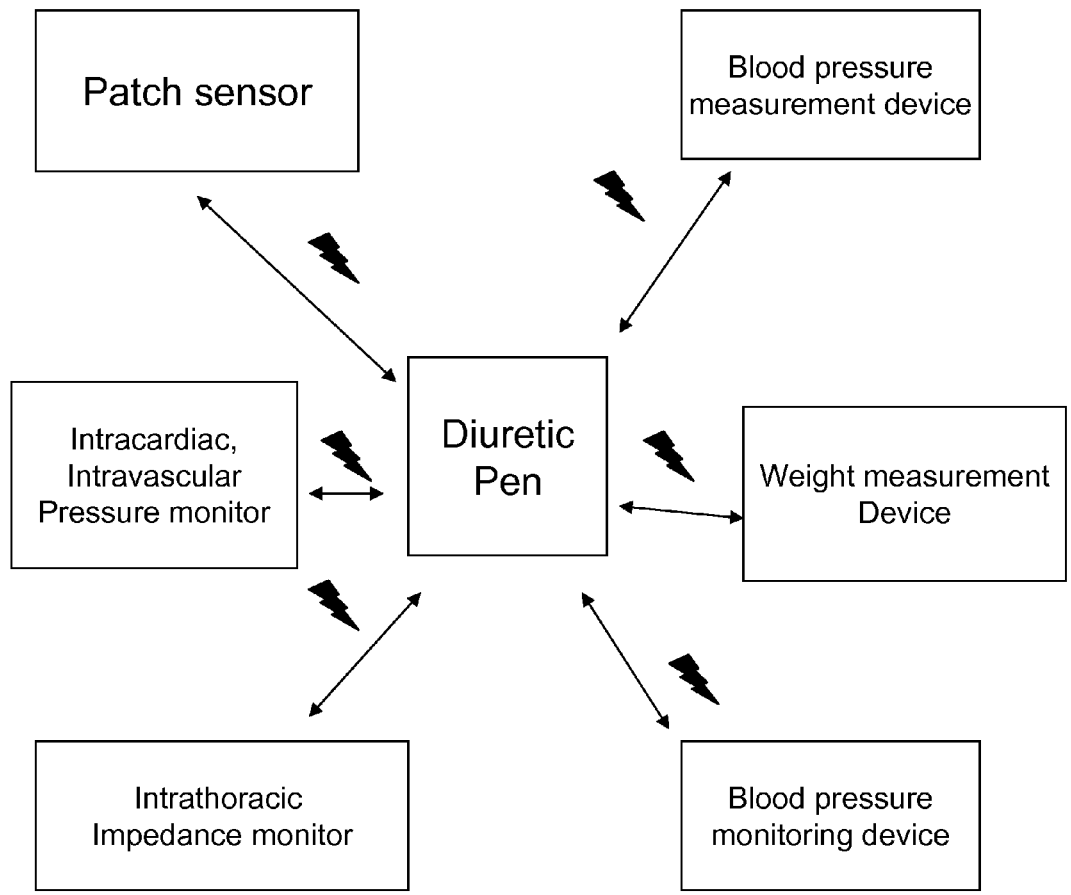
FIG. 49 illustrates examples of the biological parameters measured by devices or sensor communicatively coupled to the diuretic injecting pen-type device.

FIG. 49 illustrates examples of biological parameters that are measured by various devices and/or sensors. These devices and/or sensors are connected to a diuretic pen wirelessly in some embodiments. The diuretic pen can compute the dose of diuretic injection based on these biological parameters.

Figure 50:
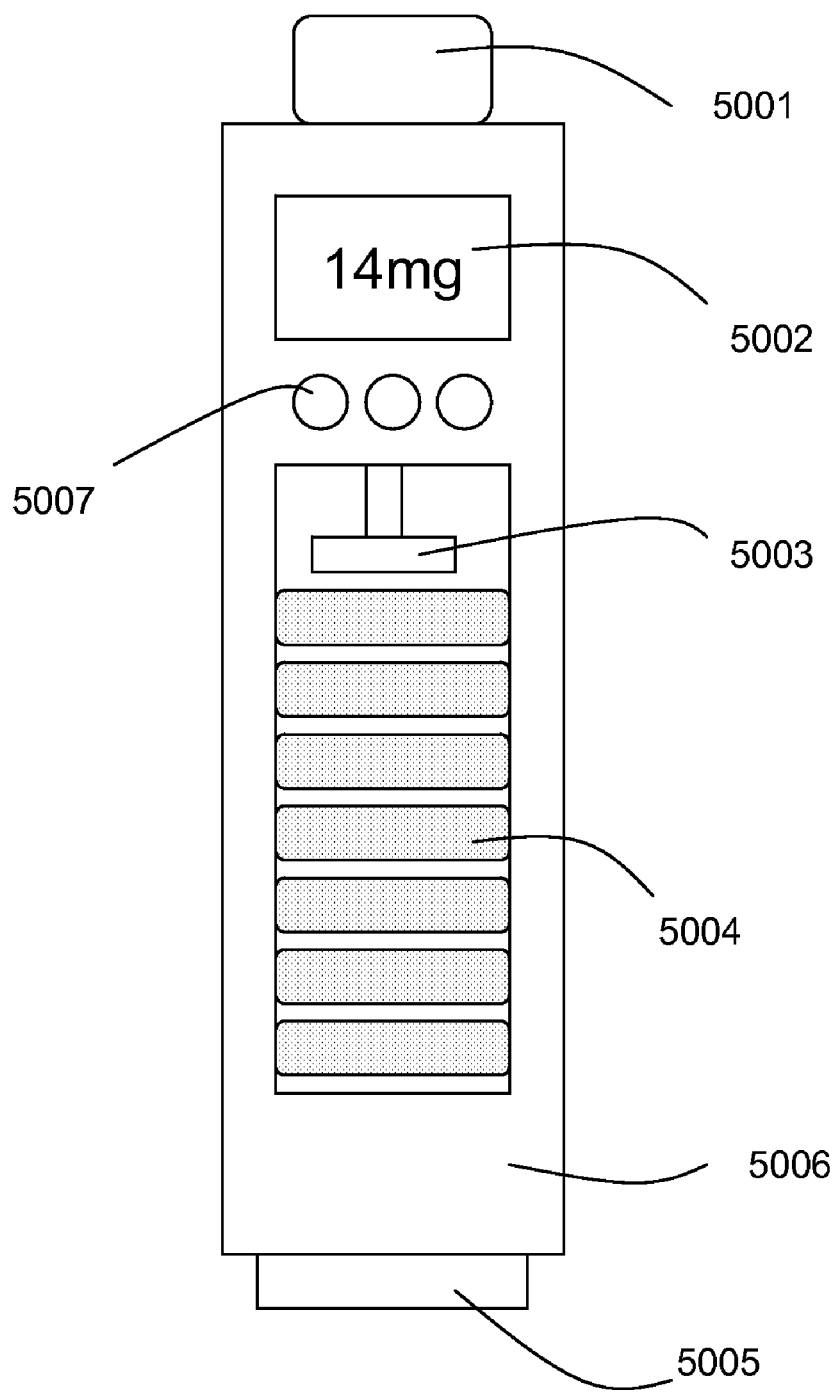
FIG. 50 illustrates another type of drug-dispensing pen-type apparatus for dispensing pills.

FIG. 50 illustrates another embodiment of the present invention. This figure shows another type of a drug dispensing apparatus. One embodiment of this drug dispensing apparatus is a pen-type apparatus 5006 which contains medication pills 5004. Some embodiments of this pen-type apparatus contain drug suspension. For example, a user may use this pen-type drug dispensing apparatus 5006 based on "sodium counting." "Sodium counting" is utilized when a user or a processor of a device calculates the dosage of diuretic based on the amount of sodium intake. For example, a user may be instructed by a physician to use 2 mg of furosemide per 50 mg of sodium intake. The pen-type apparatus might contain multiple 2 mg or 1 mg furosemide pills, though various doses of furosemide can be contained in the apparatus. If a user plans to eat 350 mg of sodium, the user can take 14 mg of furosemide according to the "sodium counting." Thus, 14 mg can be input into the pen-type apparatus using a button 5007 and a knob 5001. When knob 5001 is pushed, screw 5003 is moved to push the pills out of the drug container. Screw 5003 movement is controlled by a processor in some embodiments, though screw 5003 movement is controlled manually in other embodiments. The dosage of 14 mg furosemide is not readily available at a pharmacy because 14 mg is not a commonly used dose of furosemide pill. If the pen-type apparatus contains 2 mg furosemide pills, 7 furosemide tablets are taken out of the dispenser. This pen-type drug dispensing apparatus makes it easy to dispense various doses of diuretics and other medications. In one embodiment, this pen-type diuretic dispensing apparatus contains a processor which can compute the dose of diuretics when a user inputs the amount of sodium or salt into the pen-type diuretic dispensing apparatus. A user can input the amount of sodium or salt using knob 5001 and/or buttons on the apparatus. In alternative embodiments, when knob 5001 is pressed, a predetermined number of pills are released out of the container 5006. For example, two tablets of 1 mg furosemide pill can be released out of the container when knob 5001 is pressed. The user may be instructed to press the knob 5001 one time when the user plans to eat food with low salt and/or water content, to press the knob 5001 twice when a user plans to eat food with moderate salt and/or water content, or press the knob 5001 three times when he plans to eat food with high salt and/water content.

Figure 51:
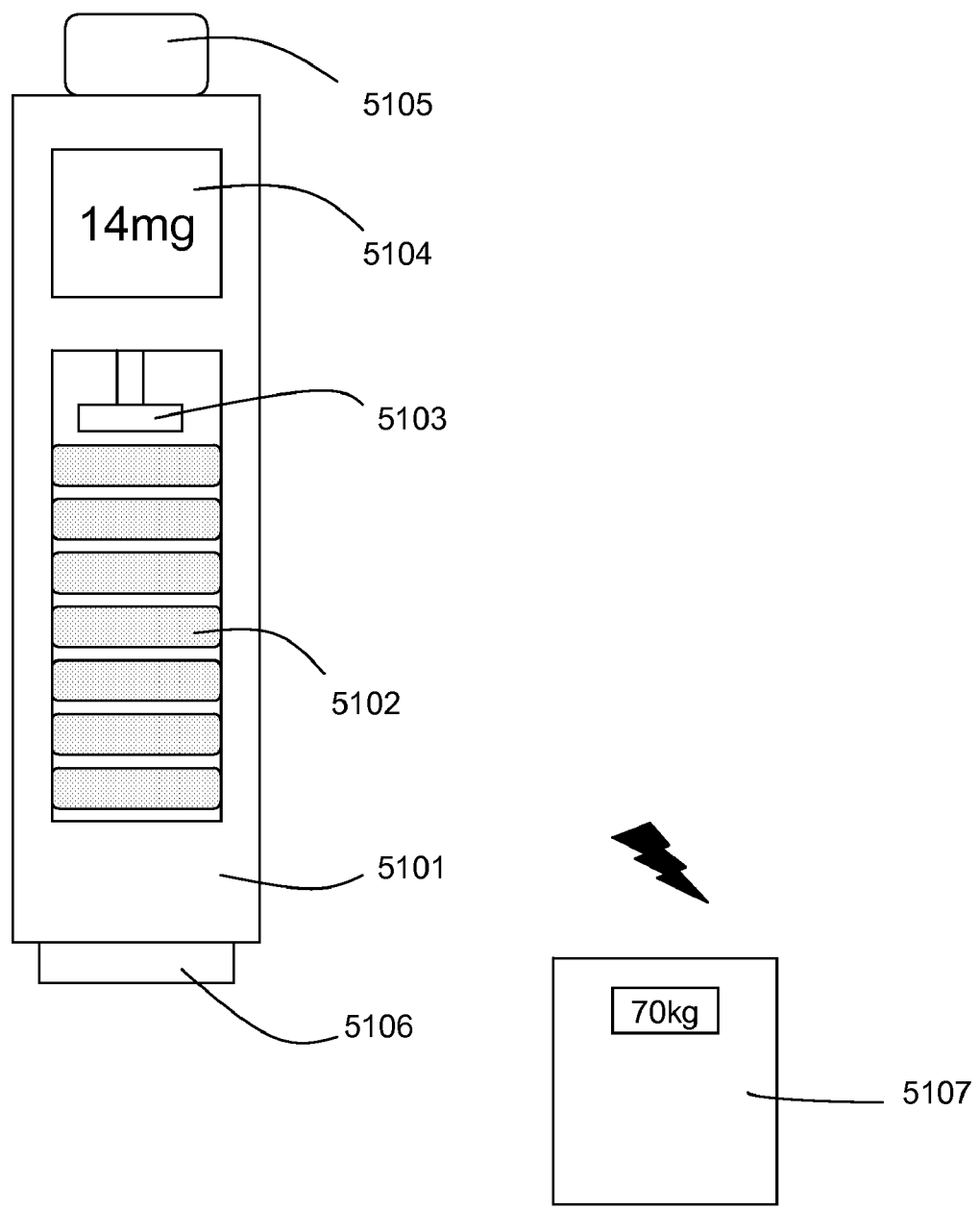
FIG. 51 illustrates the drug-dispensing pen-type apparatus in wireless communication with a weight measurement apparatus.

FIG. 51 illustrates another embodiment of the present invention. The pen-type apparatus 5101 is wirelessly connected with a weight measurement apparatus 5107. The weight measured by the weight measurement apparatus 5107 is wirelessly transmitted to the pen-type apparatus 5101. The transmitted weight information enters the processor in the pen-type apparatus 5101, and the processor computes the dosage of the diuretics based on the weight. The dosage of the diuretics is displayed on screen 5104. When knob 5105 is pushed, screw 5103 is moved to push the pills out of the drug container 5106. Screw 5103 movement can be controlled by a processor or controlled manually.

Figure 52:
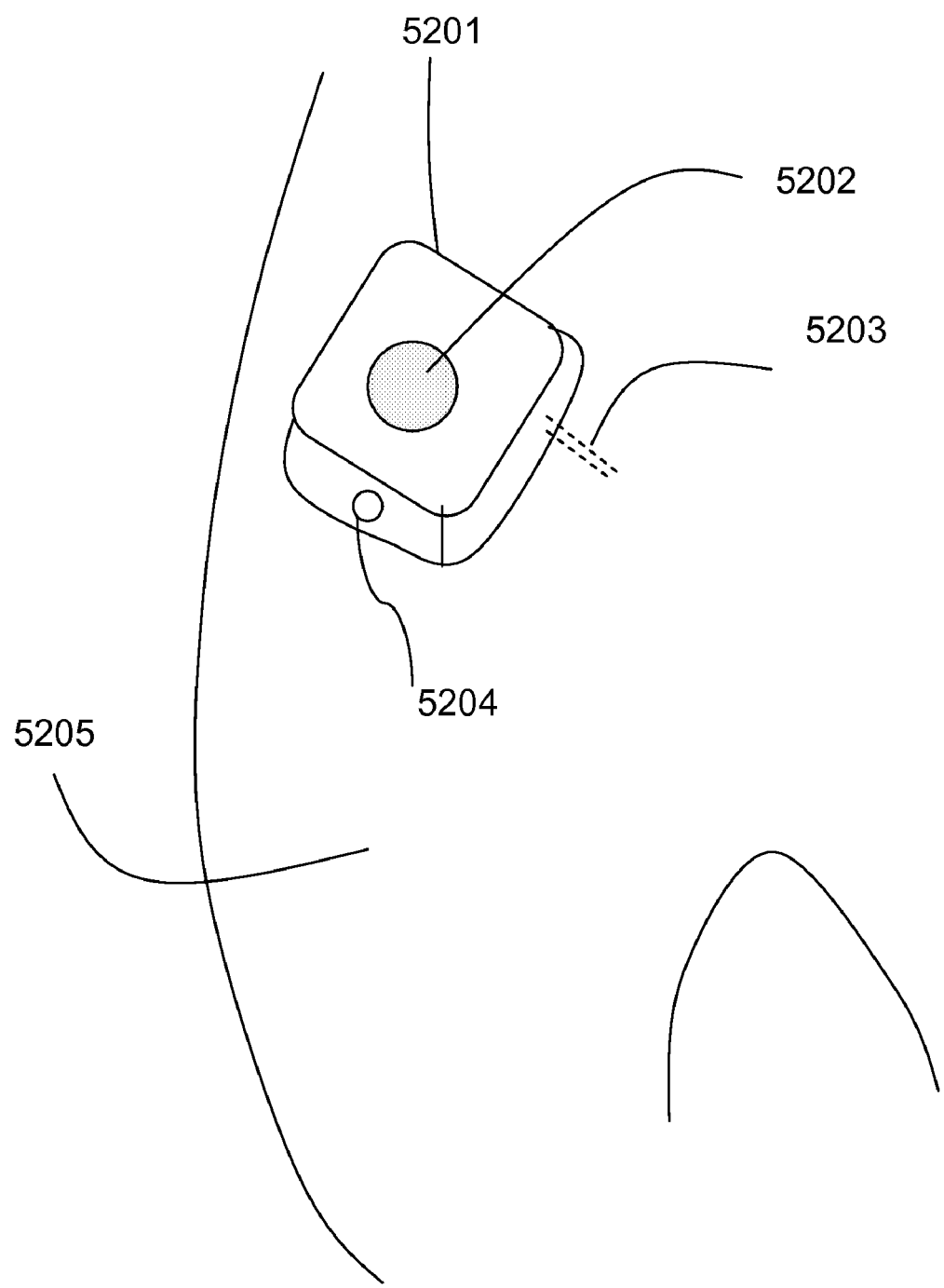
FIG. 52 illustrates a disposable external diuretic infusion pump.

FIG. 52 illustrates another embodiment of the invention. In this embodiment, a disposable external diuretic infusion pump 5201 is attached to the body 5205 of a user. This disposable external diuretic infusion pump includes a reservoir that contains the diuretic. This external diuretic infusion pump 5201 can be a metered dose infusion pump. The external diuretic infusion pump 5201 is set to deliver a predetermined volume of a drug to the user. When the user pushes a button 5202, a predetermined volume of the drug is delivered via a cannula 5203 to the user. The tip of the cannula 5203 is located subcutaneously in a preferred embodiment. In some embodiments, a reservoir may be refilled through a hole 5204. One example of a metered dose diuretic infusion is as follows. If a user is expected to eat food that contains salt, the user may be instructed to use this metered dose diuretic infusion pump before or at the time of eating this food. For example, a pump may deliver 1 mg of furosemide to the user each time button 5202 is pressed. The user can be instructed to press the button 5202 one time when the user plans to eat food with low salt content, twice when the user plans to eat food with moderate salt content, three times when the user plans to eat food with high salt content. The user may be able to urinate and excrete salt shortly after eating using this device system. People with heart failure are instructed to avoid food with high salt content because of body salt and fluid overload. This apparatus and method can allow people to take an extra amount of salt/water and still prevent them from developing salt/body fluid overload. The metered dose diuretic infusion pump can deliver a diuretic based on measured body weight. The user may be instructed to press the button 5202 once when the measured body weight is 1 kg above target weight, twice when the measured body weight is 1-2 kg above target weight, and three times when the measured body weight is more than 2 kg above target weight. The metered dose drug infusion pump can be implanted under skin in some embodiments.

Figure 53:
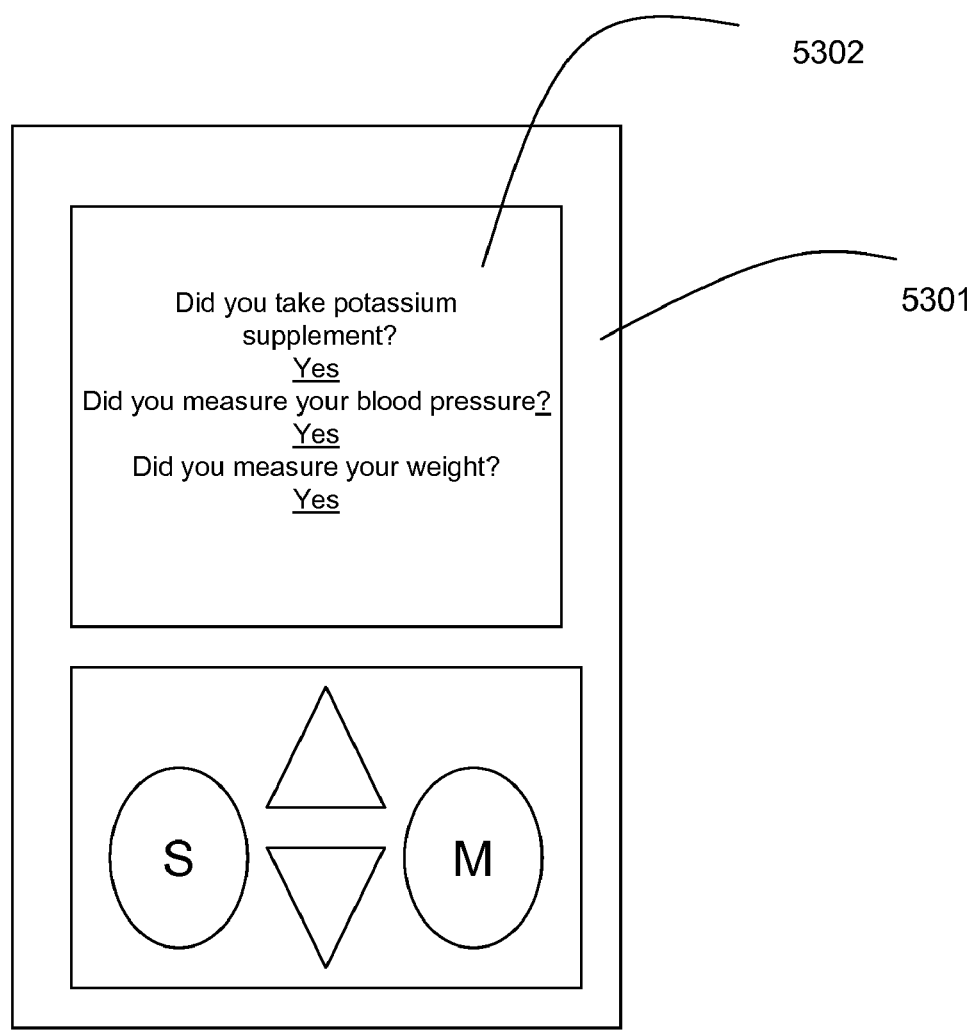
FIG. 53 shows another embodiment of a diuretic infusion pump with a feedback mechanism.

FIG. 53 illustrates another embodiment. It is important to measure body weight regularly, to take electrolyte supplements, such as potassium supplement or magnesium supplement, and to measure blood pressure while a user uses a diuretic infusion pump for safety reasons. As shown in FIG. 53, the user is asked if he took potassium supplement, measured his body weight, and measured his blood pressure. If the user inputs "yes," the diuretic infusion pump is programmed to continue diuretic infusion. If the user inputs "no," the diuretic infusion pump can be programmed to discontinue diuretic infusion until the user inputs "yes." This feedback mechanism is a safety feature of the diuretic infusion system.

FIGS. 54 and 55 show various biological parameters and factors that may be used with various embodiments, such as that of FIG. 42. A remote control device may communicate wirelessly or via other methods with various devices/sensors as shown in FIG. 54. A remote control device may use various biological parameters shown in FIG. 55 to compute the dosage of diuretics.

Figure 56:
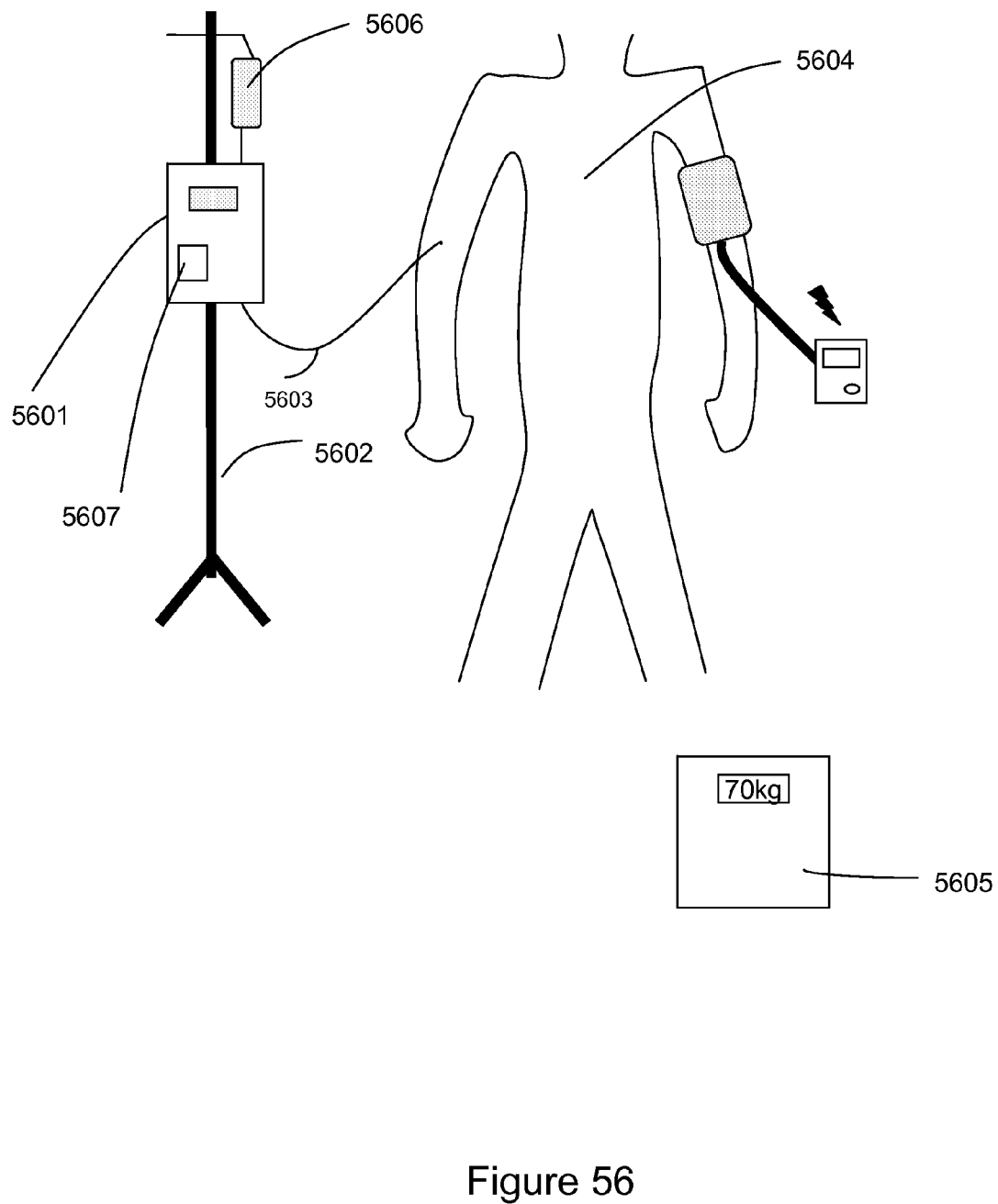
FIG. 56 illustrates another diuretic infusion system using an ambulatory diuretic infusion pump.

FIG. 56 illustrates an ambulatory diuretic infusion pump 5601 mounted at a pole 5602. A diuretic contained in a bag 5606 is infused into a vein of a patient 5604 through intravenous tube system 5603. The diuretic infusion pump 5601 contains a controller which adjusts the rate of diuretic infusion based on weight and/or other biological parameters. A user can input the weight measured by weight measurement scale 5605 into the diuretic infusion pump 5601 using a keypad. 5607 or using a remote control device. The weight measured by the scale 5605 can be transmitted wirelessly to the diuretic infusion pump in another embodiment.

Even though the term "diuretic infusion pump" (or "diuretic infusion system" or similar variants) is used in this application, one of ordinary skill in the art would know that this term is not limited to the use of diuretics, but can also use other types of drugs, as well. Thus, this term is not limited to diuretics. Many different drugs can be used for the diuretic infusion pump. Examples of such drugs are described in other parts of the application.

Diuretic infusion pumps can contain two reservoirs in some embodiments. One reservoir can contain furosemide. The other reservoir can contain buffering solution. Buffering solution includes (but is not limited to) sodium chloride solution, Lactated Ringer's solution, or Dextrose 5% solution. Some furosemide solution may have a high pH of about 9. Mixing a furosemide solution with a sodium chloride solution, Lactated Ringer's solution or Dextrose 5% solution may lower the pH of the furosemide solution.

Furosemide discolors when it is exposed to light. Discolored furosemide is not recommended to be used. A reservoir and cartridge within a diuretic infusion pump may be light resistant to protect furosemide or other drugs from being exposed to the light.

In all of the above embodiments, the diuretic infusion pump was located external to the body. However, alternatively, internal and implantable diuretic infusion pumps may also be made. The diuretic infusion pumps are also shown as portable in the above description. In alternative embodiments, the diuretic infusion pump may not be portable.

In another aspect of the invention, a user of the diuretic infusion pump may choose to use the device for long term or may choose to use it for short term when his body weight changes. The diuretic infusion pump can also be used in various locations: home, outpatient facilities and hospitals, as well as the intensive care unit.

Programs and protocols coupled with the diuretic infusion pump preferably have various safety measures to minimize side effects of diuretics. One example of a safety measure is that the diuretic infusion pump stops infusing diuretics when a user does not measure body weight in a certain period after previous weight measurements. For example, the diuretic infusion pump may be programmed to stop diuretic infusion in two days if the diuretic infusion pump does not receive a new body weight measurement. This safety measure helps to avoid using inappropriately high dose of diuretics when previously measured body weight is higher than actual body weight. Alarms and display on the screen may be programmed to request a user to enter a new body weight measurement into the diuretic infusion pump.

The above description and illustration of preferred embodiments of the invention has been presented to provide illustration and description. It is not intended to limit the invention to the precise forms that are disclosed. Many variations and modifications will be apparent to people skilled in this art.

Depending on the form of the components, "coupling" or "connection" between components may take different forms. Dedicated circuitry can be coupled to each other by hardwiring or by accessing a common register or memory location, for example. Software "coupling" can occur by any number of ways to pass information between software components (or between software and hardware, if that is the case). The term "coupling" is meant to include all of these and is not meant to be limited to a hardwired permanent connection between two components. In addition, there may be intervening elements. For example, when two elements are described as being coupled to each other, this does not imply that the elements are directly coupled to each other nor does it preclude the use of other elements between the two.

What is claimed is:

1. A method of automatically infusing diuretic to an ambulatory human patient at home comprising:
attaching a diuretic infusion device to the body of the ambulatory human patient;
receiving weight information based on body weight measurements performed by the patient to measure his body weight;
adjusting an infusion rate of diuretic into the patient based on the received weight information according to a predetermined protocol wherein:
a program
calculates a difference between a target weight and a measured weight;
determines a rate of an initial diuretic infusion;
adjusts the rate of diuretic infusion using a diuretic infusion protocol chosen among a plurality of diuretic infusion protocols; and
calculates a difference between the target weight and measured weights at different time points within a day; and
a controller controls a pump based on one of the measured weight of the patient thereby controlling a rate of infusion of the diuretic according to the program to maintain the target weight by adjusting the rate of diuretic infusion until one of the measured weights reaches near the target weight; wherein the adjustment of the diuretic infusion rate starts after a measured weight information is put into the diuretic infusion device, adjusting the diuretic infusion rate with each of the weight measurements at the different time points, and continues adjusting the infusion rate until one of the measured weight reaches near the target weight; and
infusing the diuretic subcutaneously in the human body at the infusion rate determined by the program.

2. The method of claim 1 wherein the predetermined protocol specifies an infusion rate to maintain the body weight of the patient at a target weight.

3. The method of claim 1 wherein the predetermined protocol specifies an infusion rate to maintain the body weight of the patient within a target weight range.

4. The method of claim 1 wherein the predetermined protocol specifies an infusion rate that does not exceed an upper limit.

5. The method of claim 1 wherein the predetermined protocol specifies an infusion rate that does not fall below a lower limit.

6. The method of claim 1 wherein the predetermined protocol specifies no infusion of the diuretic if the measured body weight is less than a predetermined weight.

7. The method of claim 1 wherein the set of predetermined protocols includes a low dose protocol, a moderate dose protocol, and a high dose protocol.

8. The method of claim 1 wherein the predetermined protocol specifies an infusion rate that increases monotonically as a function of the difference between the measured body weight and a target body weight.

9. The method of claim 8 wherein the infusion rate is proportional to the weight difference.

10. The method of claim 8 wherein the infusion rate is piecewise constant but monotonically increasing as a function of the weight difference.

11. The method of claim 1 wherein the infusion rate includes a bolus rate.

12. The method of claim 1 wherein the infusion rate includes a basal rate.

13. The method of claim 1 wherein the step of receiving weight information comprises wirelessly receiving the weight information.

14. The method of claim 1 wherein the predetermined protocol is further based on a biological parameter other than body weight.

15. The method of claim 1 wherein the predetermined protocol specifies the infusion rate based on body weight measurements taken at two or more different times.

16. The method of claim 1 wherein the predetermined protocol specifies the infusion rate based on an average of body weight measurements taken at two or more different times.

17. The method of claim 1 wherein the predetermined protocol specifies an alarm if the measured body weight exceeds an upper limit.

18. A method of automatically infusing diuretic to an ambulatory human patient at home comprising:
attaching a diuretic infusion device to the body of the ambulatory human patient;
receiving weight information based on body weight measurements performed by the patient to measure his body weight;
adjusting an infusion rate of diuretic into the patient based on the received weight information according to a predetermined protocol wherein:
a program
calculates a difference between a target weight and a measured weight;
determines a rate of an initial diuretic infusion;
adjusts the rate of diuretic infusion using a diuretic infusion protocol chosen among a plurality of diuretic infusion protocols; and
calculates a difference between the target weight and measured weights at different time points within a day; and
a controller controls a pump based on one of the a measured weight of the patient thereby controlling a rate of infusion of the diuretic according to the program to maintain the target weight by adjusting the infusion rate of the diuretic when the measured weight is different from the target weight; adjusting the rate of diuretic infusion until one of the measured weights reaches near the target weight; wherein the adjustment of the diuretic infusion rate starts when a measured weight information is put into the diuretic infusion device, adjusting the diuretic infusion rate with each of the weight measurements at the different time points, and continues adjusting the infusion rate until one of the measured weight reaches near the target weight; displaying the calculated infusion rate to the patient; and infusing the diuretic subcutaneously into the human body at the infusion rate determined by the program.

19. The method of claim 18 further comprising: transmitting the weight information to the patient's healthcare provider.

20. The method of claim 18 further comprising: recording the weight information.

* * * * *